United States Patent
Gan et al.

(10) Patent No.: US 9,011,965 B2
(45) Date of Patent: Apr. 21, 2015

(54) GRADIENT COATING FOR BIOMEDICAL APPLICATIONS

(75) Inventors: Lu Gan, Memphis, TN (US); Marcus L. Scott, Memphis, TN (US); Shilesh C. Jani, Memphis, TN (US); Laura S. Whitsitt, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 21 days.

(21) Appl. No.: 12/919,927

(22) PCT Filed: Feb. 27, 2009

(86) PCT No.: PCT/US2009/035444
§ 371 (c)(1),
(2), (4) Date: Aug. 27, 2010

(87) PCT Pub. No.: WO2009/111300
PCT Pub. Date: Sep. 11, 2009

(65) Prior Publication Data
US 2011/0014258 A1    Jan. 20, 2011

Related U.S. Application Data

(60) Provisional application No. 61/032,767, filed on Feb. 29, 2008.

(51) Int. Cl.
*A61L 27/30* (2006.01)
*A61L 27/54* (2006.01)

(52) U.S. Cl.
CPC .................. *A61L 27/30* (2013.01); *A61L 27/54* (2013.01); *A61L 2300/102* (2013.01); *A61L 2300/104* (2013.01); *A61L 2300/112* (2013.01); *A61L 2300/402* (2013.01); *A61L 2300/404* (2013.01); *A61L 2300/406* (2013.01); *A61L 2300/408* (2013.01); *A61L 2300/412* (2013.01); *A61L 2300/608* (2013.01); *A61L 2420/08* (2013.01)

(58) Field of Classification Search
USPC ............. 427/2.27, 2.29, 2.26, 309; 433/201.1
See application file for complete search history.

(56) References Cited

U.S. PATENT DOCUMENTS

| | | | |
|---|---|---|---|
| 5,009,898 A * | 4/1991 | Sakuma et al. | 424/618 |
| 5,151,122 A | 9/1992 | Atsumi et al. | |
| 5,266,534 A | 11/1993 | Atsumi et al. | |
| 5,268,174 A | 12/1993 | Sakuma et al. | |
| 5,348,577 A | 9/1994 | Atsumi et al. | |
| 5,723,038 A | 3/1998 | Scharnweber et al. | |
| 6,086,908 A | 7/2000 | Gopferich | |
| 6,127,352 A * | 10/2000 | Uribe | 514/159 |
| 6,129,928 A | 10/2000 | Sarangapani et al. | |
| 6,136,369 A * | 10/2000 | Leitao et al. | 427/2.27 |
| 6,344,061 B1 | 2/2002 | Leitao et al. | |
| 6,419,708 B1 | 7/2002 | Hall et al. | |
| 6,582,715 B1 | 6/2003 | Barry et al. | |
| 6,719,897 B1 | 4/2004 | Maltin | |
| 6,719,987 B2 | 4/2004 | Burrell et al. | |
| 2002/0018798 A1 | 2/2002 | Sewing et al. | |
| 2003/0099762 A1* | 5/2003 | Zhang et al. | 427/2.1 |
| 2004/0074568 A1 | 4/2004 | Jennissen | |
| 2004/0153165 A1 | 8/2004 | Li et al. | |
| 2006/0161256 A1 | 7/2006 | Ziegler et al. | |
| 2006/0210494 A1* | 9/2006 | Rabiei et al. | 424/57 |
| 2006/0286140 A1 | 12/2006 | Wickstrom et al. | |
| 2007/0141112 A1 | 6/2007 | Falotico et al. | |

FOREIGN PATENT DOCUMENTS

| | | |
|---|---|---|
| CA | 2187512 | 8/1996 |
| CN | 1589161 A | 3/2005 |
| DE | 10 2004 011293 A1 | 9/2005 |
| EP | 1 764 119 A1 | 3/2007 |
| JP | H03-161429 | 7/1991 |
| JP | H10-503108 | 3/1998 |
| JP | H10-151187 | 6/1998 |
| JP | 2000-507218 | 6/2000 |
| JP | 2005-329060 | 12/2005 |
| JP | 2005-538809 | 12/2005 |
| JP | 2006-502762 | 1/2006 |
| JP | 2007-190369 | 8/2007 |
| WO | WO 00/23124 A1 | 4/2000 |
| WO | WO 00/76486 A1 | 12/2000 |
| WO | WO 02/18003 A1 | 3/2002 |
| WO | WO 03/070288 A2 | 8/2003 |
| WO | WO 2004/026361 | 4/2004 |
| WO | 2007/022211 A2 | 2/2007 |
| WO | 2007/048812 A1 | 3/2007 |
| WO | WO 2008/011169 | 1/2008 |
| WO | 2009/111307 A2 | 9/2009 |

OTHER PUBLICATIONS

International Search Report cited in PCT/US2009/035444 dated Oct. 19, 2009 (4 pages).

X. Zhang, et al., "Toughening of calcium hydroxyapatite with silver particles," Journal of Materials Science, Publisher Springer Netherlands, Issue vol. 32, No. 1 / Jan. 1997, pp. 235-243 (9 pages).

(Continued)

*Primary Examiner* — Ali Soroush
(74) *Attorney, Agent, or Firm* — Krieg DeVault LLP

(57) ABSTRACT

The present invention provides a coating comprising a bioactive material and an antimicrobial agent, wherein the concentration of said antimicrobial agent varies throughout the thickness of the coating.

38 Claims, 26 Drawing Sheets

(56) References Cited

OTHER PUBLICATIONS

T. K. Chaki, et al., "Densification and strengthening of silver-reinforced hydroxyapatite-matrix composite prepared by sintering," Journal of Materials Science: Materials in Medicine, Issue vol. 5, No. 8 / Aug. 1994, pp. 533-542 (10 pages).

M. Shirkhanzadeh, et al., "Bioactive delivery systems for the slow release of antibiotics: incorporation of Ag+ ions into micro-porous hydroxyapatite coatings," Materials Letters, vol. 24, Issues 1-3, Jun. 1995, pp. 7-12 (6 pages).

Q.L. Feng, et al., "Ag-Substituted Hydroxyapatite Coatings with Both Antimicrobial Effects and Biocompatibility," Journal of Materials Science Letters, Publisher Springer Netherlands, Issue vol. 18, No. 7 / Apr. 1999, pp. 559-561 (3 pages).

Giuseppe Pezzotti, et al., "Study of the toughening mechanisms in bone and biomimetic hydroxyapatite materials using Raman microprobe spectroscopy," Journal of Biomedical Materials Research Part A, vol. 65A, Issue 2, 2003, pp. 229-236 (8 pages).

W. Chen, et al., "In vitro anti-bacterial and biological properties of magnetron co-sputtered silver-containing hydroxyapatite coating," Biomaterials, vol. 27, Issue 32, Nov. 2006, pp. 5512-5517 (6 pages).

T. N. Kim, et al., "Antimicrobial effects of metal ions (Ag+, Cu2+, Zn2+) in hydroxyapatite," Journal of Materials Science: Materials in Medicine, Chapman & Hall, Issue vol. 9, No. 3 / Mar. 1998, pp. 129-134 (6 pages).

W. Chen, et al., "Antibacterial and osteogenic properties of silver-containing hydroxyapatite coatings produced using a sol gel process," J Biomed Mater Res A. Sep. 15, 2007;82(4): pp. 899-906 (8 pages).

N. Rameshbabu et al., "Antibacterial Nanosized Silver Substituted Hydroxyapatite: Synthesis and Characterization," 2006 Wiley Periodicals, Inc., pp. 581-591 (11 pages).

Q. L. Feng, et al., "Antibacterial effects of Ag-HAp thin film on alumina substrates," Thin Solid Films 335 (1998) 214-219 (6 pages).

Decision on Rejection issued in Chinese Application No. 200980115899.9, mailed Nov. 18, 2013, 18 pages.

Japanese First Office Action; Japanese Patent Office; Japanese Application No. 2010-548897, mailed Oct. 8, 2013; 13 pages.

Chinese First Office Action issued in Chinese Application No. 200980115899.9, mailed Jan. 25, 2013, 23 pages.

Chinese Search Report issued in Chinese Application No. 200980115899.9, mailed Jan. 17, 2013, 6 pages.

W. Chen et al., "Antibacterial and Osteogenic Properties of Silver-Containing Hydroxyapatite Coatings Produced Using a Sol Gel Process", Journal of Biomedical Material Research Part A, Sep. 15, 2007, pp. 899-906, vol. 82A Issue 4, Copyright 2007 Wiley Periodicals, Inc.

Roger J. Narayan et al., The Use of Functionally Gradient Materials in Medicine, JOM, Jul. 2006, pp. 52-56.

Patent Examination Report No. 1; Australian Patent Office; Australian Patent Application No. 2009222165; dated Sep. 20, 2013; 6 pages.

First European Office Action; European Patent Office; European Patent Application No. 09718375.0; Jul. 9, 2013; 9 pages.

Japanese Decision of Rejection; Japanese Patent Office; Japanese Application No. 2010-548897; mailed Aug. 11, 2014; 5 pages.

Second European Office Action; European Patent Office; European Patent Application No. 09718375.0; Jan. 8, 2015; 9 pages.

\* cited by examiner (a)

(b)

(a)

(b)

(a)

(b)

(a)

(b)

(a)

(b)

(a)

(b)

(a)

(b)

(a)

(b)

(a)

(b)

(a)

(b)

GRADIENT COATING FOR BIOMEDICAL APPLICATIONS

This is a U.S. National Stage patent application filed under 35 U.S.C. §371 from PCT International Application Number PCT/US2009/035444, International Filing Date 27 Feb. 2009, International Publication Number WO 2009/111300, International Publication Date 11 Sep. 2009, which is incorporated herein by reference in its entirety, which PCT application, and this application, claim priority to U.S. Provisional Patent Application Ser. No. 61/032,767, filed 29 Feb. 2008, which U.S. Provisional patent application is incorporated herein by reference in its entirety.

FIELD OF THE INVENTION

The present invention relates to drug delivery and body treating compositions and more particularly to surgical implants having a body treating composition.

BACKGROUND

Biomaterial-centered infection is a prevalent cause of revision surgery in general and particularly in total joint replacement. Revision surgeries due to infection are risky and invasive. Conventionally, if an infection occurs after a total joint replacement, bone ingrowth is inhibited by bacteria, and the responsible implant must be removed and replaced with a temporary implant composed of anti-infection agents. During this time, a patient has an extensive stay in a hospital or is otherwise rendered immobile because the temporary infection-fighting implant is typically non-load bearing. In some instances, a patient may be confined to a bed or wheelchair for weeks before the infection is stopped. When the infection subsides, the temporary infection-fighting implant is removed and a revision implant is inserted in its place. This procedure is costly to the patient in both time and money. Infections associated with inserting a medical device can be devastating, painful, and cause prolonged disability. Treating the infection may cost tens of thousands of dollars. Moreover, surgeons are presented with greater risks if post-operative infection occurs.

Conventionally, certain precautions are taken to prevent post-surgery infection. For example, antibiotics are provided to a patient before and after surgery to reduce the risk of infection. Antibiotics are typically given within one hour of the start of surgery (usually once in the operating room) and continued for a short period following the procedure. Short operating time and minimal Operating Room (OR) traffic may further reduce the risk of infection during surgery, such as a total joint replacement procedure or an intramedullary nailing procedure. By increasing efficiency in the OR, a surgeon may effectively lower the risk of infection by limiting the time the anatomy is exposed. Limiting the number of operating room personnel entering and leaving the operating room is also thought to decrease risk of infection. Another precaution is the strict adherence to sophisticated sterilization techniques. However, despite the aforementioned precautions being taken, post-surgery infection remains a real and serious threat.

There are generally two types of post-surgery infections. First, early-stage infection occurs in the weeks following surgery and may sometimes be cured with a surgical washout and intravenous antibiotics. The exact period of surgical washout necessary is debatable but is typically between about three to about eight weeks. It is, however, generally accepted that curing an infection without removing the responsible orthopaedic implant becomes harder and harder with each passing day after surgery. Second, late-stage infection usually occurs after months or even years after surgery and almost always requires removal of the orthopaedic implant. An "antibiotic spacer" is placed into the void and intravenous antibiotics are provided to the patient. Patients with late-stage infection may need to undergo at least six weeks of intravenous (IV) antibiotics, possibly more, before the orthopaedic implant can be replaced.

In the area of orthopaedics, the prior art has attempted to coat implants with antimicrobial products to prevent infection (see e.g. "Antibacterial Nanosized Silver Substituted Hydroxyapatite: Synthesis and Characterization," by Rameshbabu et al. (2006); "In Vitro Anti-bacterial and Biological Properties of Magnetron Co-sputtered Silver-containing Hydroxyapatite Coating," by Chen et al. (2006); "Antibacterial Effects of Ag-Hap Thin Films on Alumina Substrates," by Feng et al. (1998)).

U.S. Pat. No. 6,719,987 issued on Apr. 13, 2004 to Nucryst Pharmaceuticals Corp. of Alberta, Canada discusses antimicrobial coatings or powders that provide an effective and sustainable antimicrobial effect. The '987 patent is herein incorporated by reference in its entirety.

U.S. Published Patent Application No. 2004/0074568A1 published on Apr. 22, 2004 discusses an anchor module for covalently bonding a mediator module, such as an antibiotic, to a medical implant. The disclosure of the '568 Publication is herein incorporated by reference in its entirety.

U.S. Published Patent Application 2006/0286140A1 published on Dec. 21, 2006 discusses a medical implant with therapeutic molecules bonded to its surface. The disclosure of the '140 Publication is herein incorporated by reference in its entirety.

In vitro cell culture studies have shown that low concentrations of silver may reduce the risk of infection. Thus, with the onset of multi-drug resistance in many bacterial strains, a new treatment methodology with the powerful antibacterial properties of silver at low concentrations has been sought. For example, U.S. Pat. No. 5,151,122, issued on Sep. 29, 1992, suggests adding any one of copper, silver, or zinc to a hydroxyapatite coating in order to provide antibacterial effectiveness. Similarly, U.S. Pat. No. 5,266,534, issued on Nov. 30, 1993, suggests adding silver and silicon to an HA coating. U.S. Pat. No. 5,348,577, issued on Sep. 20, 1994, further suggests adding silver and zinc for antibacterial purposes. U.S. Pat. No. 5,268,174, issued on Dec. 7, 1993, suggests an antimicrobial hydroxyapatite powder composition having zinc and further including fluoride for its bone-stimulating properties. U.S. Pat. Nos. 5,151,122, 5,266,534, 5,348,577, and 5,268,174, are incorporated by reference as though fully set forth herein.

The present invention discusses an implant which aims to improve at least one of the problems of the prior art.

SUMMARY OF THE INVENTION

In one aspect of the invention, there is provided a sol-gel process for preparing a silver-containing calcium derivative, preferably a crystallized, silver-containing calcium phosphate, the process comprising the steps of: (a) mixing a calcium precursor and a silver precursor to obtain a homogenous sol-gel solution; (b) aging the homogenous sol-gel solution; and (c) calcining the homogenous sol-gel solution.

In one embodiment of the invention, step (a) further comprises mixing at least one phosphorus precursor, fluorine precursor, and/or carbonate precursor to obtain a homogenous sol-gel solution.

In one embodiment of the invention, step (b) further comprises aging the homogenous sol-gel solution at about or above room temperature. The skilled person is well aware of a sufficient time for aging, but it is generally a number of days to a few weeks, for example about 8 days.

In one embodiment of the invention, the calcining step (c) further comprises calcining the homogenous sol-gel solution at a temperature higher than room temperature.

In one embodiment of the invention, there is provided a sol-gel process for preparing a crystallized, silver-containing calcium phosphate, the process comprising the steps of: (a) mixing calcium precursor, silver precursor, phosphorus precursor, fluorine precursor, and/or carbonate precursor to obtain a homogenous sol-gel solution; (b) aging the homogenous sol-gel solution at room temperature for about 8 days; and (c) calcining the homogenous sol-gel solution at a temperature higher than room temperature.

In one embodiment of the invention, the calcium phosphate comprises hydroxyapatite. In another embodiment of the invention, the calcium phosphate comprises tricalcium phosphate.

In one embodiment of the invention, the calcium precursor comprises calcium nitrate, the silver precursor comprises silver nitrate, the phosphorus precursor comprises ammonium dihydrogen phosphate, the fluorine precursor comprises ammonium fluoride, and/or the carbonate precursor comprises ammonium carbonate.

In another embodiment of the invention, the homogenous sol-gel solution comprises a silver precursor concentration from about 0.1 wt % to about 10 wt %, from about 0.1 wt % and to 7 wt %, from about 0.1 wt % to about 5 wt %, from about 0.5 wt % to about 3 wt %, or from about 0.5 wt % to about 2 wt %. In yet another embodiment of the invention, the homogenous sol-gel solution comprises a fluorine precursor concentration of about 0.001 to 0.1M, preferably about 0.01M. In one other embodiment of the invention, the homogenous sol-gel solution comprises a carbonate precursor concentration of about 0.004 to 0.4M, preferably about 0.042M.

In another aspect of the invention, there is provided a sol-gel thin film process for applying a silver-containing calcium phosphate thin film coating to a medical implant, the process comprising the steps of: (a) coating the implant with a homogeneous sol-gel solution comprising one or more of a calcium precursor, silver precursor, phosphorus precursor, fluorine precursor, and/or carbonate precursor; and (b) calcining the thin film.

In one embodiment, the coating step comprises a dipping step, and before the film is calcined the implant is withdrawn from the solution.

In embodiments of this aspect, the implant can be dipped for any suitable amount of time to allow for a suitable coating on the implant, e.g. 30 seconds, the withdrawal of the implant can be carried out in such a manner that a uniform coating is achieved, for example withdrawing the implant from the sol-gel solution vertically at a control rate of approximately 30 cm/min, and/or calcining the thin film can be carried out at an elevated temperature.

In one embodiment of the invention, the step of coating the implant comprises dipping the implant at least twice to form at least two layers of the sol-gel solution on the implant, and wherein the step of calcining the thin film comprises a heat treatment of from about 50° C. to about 1000° C., from about 100° C. to about 400° C., from about 150° C. to about 250° C., approximately 210 degrees C. for from about 2 minutes to 1 hour, from about 10 minutes to about 30 minutes, about 15 minutes in air between coats.

In some embodiments, the step of calcining the thin film comprises a final heat treatment at a temperature of approximately 400 degrees C. in air for approximately 30 minutes.

In another embodiment of the invention, the silver-containing calcium phosphate thin film coating has a concentration gradient of silver in the coating, with the coating having a higher silver concentration at an outer coating surface and the coating having a lower silver concentration at an inner surface, wherein the higher silver concentration is achieved by coating the implant with a sol-gel solution having a higher concentration of silver, and wherein the lower silver concentration is achieved by coating the implant into a sol-gel solution having a lower silver concentration.

In some embodiments, the silver concentration at an outermost surface of the thin film coating is from about 2 wt % to about 10 wt %, from about 2 wt % to about 7 wt %, from about 2 wt % to about 5 wt %, approximately about 2 wt %, and wherein the silver concentration at an innermost surface is from about 0.1 wt % to less than about 2 wt %, from about 0.1 wt % to about 1 wt %, approximately 0.4 wt %.

In some embodiments, the step of coating comprises dipping the implant into a sol-gel solution at least twice in order to obtain a two-layer thin film coating having a single homogeneous silver concentration, wherein the single homogeneous silver concentration may be either about 0.4 wt % or about 2 wt %.

In some embodiments, a reduced silver ion release at the inner surface of the silver-containing calcium phosphate thin film coating is achieved by first using a sol-gel dip coating method, and an increased silver ion release at the outer coating surface is achieved by subsequently immersing the implant in silver fluoride or silver nitrate (10-3-10-4M) solution at room temperature for a time, e.g. for about 24 hours.

In one particular embodiment, the silver concentration profile has at least two different silver concentrations, each at different coating depths.

In yet another aspect of the invention, there is provided a process for preparing an analgesic-eluting coating, the process comprising: (a) dissolving at least one analgesic in a liquid to form a homogenous solution; (b) coating (e.g. dipping) a silver-containing calcium phosphate-coated implant with the homogeneous solution to form an analgesic antimicrobial implant; (c) withdrawing the analgesic antimicrobial implant, for example at a control rate of about 20-30 cm/min; and (d) drying the analgesic antimicrobial implant in air.

In one embodiment of the invention, the homogenous solution comprises a polymer selected from the group consisting of: Polylactic acid (PLA), poly(lactic-co-glycolic acid) (PLGA), polyglycolic acid (PGA), Polycaprolactone (PCL), equivalents thereof, and/or combinations thereof.

In yet another embodiment of the invention, the homogenous solution comprises a calcium phosphate solution, wherein the solution contains any one or more of the following: simulated body fluid (SBF), modified simulated body fluid, a calcium phosphate solution which is able to form an apatite coating at room temperature, and a silver salt such as silver nitrate or silver fluoride.

In another embodiment of the invention, the silver-containing calcium phosphate-coated implant is immersed into the homogeneous solution for about 24-48 hours before drying e.g. in air.

In yet another embodiment of the invention, the analgesic is selected from one or more of the following local anesthetics (e.g. bupivacaine), narcotic or non-narcotic analgesics: opioids, morphine, codeine, oxycodone (Percodan), levorphanol (levodromoran), propoxyphene (Darvon), and pentazocine (Talwin); or non-narcotic analgesics, such as, acetylsalicylic acid (aspirin), phenylbutazone (Butazolidine), indomethacin (Indocin), acetaminophen, and phenacetin.

In another embodiment of the invention, the analgesic antimicrobial implant has a gradient distribution of analgesic concentration within its coating, the analgesic concentration being higher adjacent an outer coating surface than at an inner surface, where the analgesic concentration is lower.

In another embodiment of the invention, the analgesic antimicrobial implant comprises a narcotic analgesic adjacent an outer coating surface and a non-narcotic analgesic adjacent an inner surface.

In another embodiment of the invention, the analgesic concentration profile has at least two different analgesic concentrations, each at different coating depths.

In yet another aspect of the invention, there is provided a process for preparing an analgesic-eluting coating, the process comprising: (a) dissolving at least one analgesic in a liquid to form a homogenous solution, the homogeneous solution further comprising a polymer selected from the group consisting of: PLA, PLGA, PGA, PCL, equivalents thereof, and/or combinations thereof and the homogeneous solution optionally further comprising silver salt(s) such as silver nitrate, silver fluoride, silver chloride and/or combinations thereof; (b) dipping a silver-containing calcium phosphate-coated implant (optionally being devoid of an analgesic) into the homogeneous solution to form an analgesic antimicrobial implant; (c) withdrawing the analgesic antimicrobial implant, e.g. at a controlled rate of about 20-30 cm/min; and (d) drying the analgesic antimicrobial implant e.g. in air.

In yet another aspect of the invention, there is provided a process for preparing an analgesic-eluting coating, the process comprising: (a) dissolving at least one analgesic in a liquid to form a homogenous solution, the homogenous solution further comprising a calcium phosphate solution, wherein the solution contains any one or more of the following: simulated body fluid (SBF), modified simulated body fluid, a calcium phosphate solution which is able to form an apatite coating at room temperature, and a silver salt such as silver nitrate, silver fluoride, silver chloride and combinations thereof; (b) dipping a silver-containing calcium phosphate-coated implant (optionally being devoid of an analgesic) into the homogeneous solution to form an analgesic antimicrobial implant; (c) withdrawing the analgesic antimicrobial implant e.g. at a control rate of about 20-30 cm/min; and (d) drying the analgesic antimicrobial implant e.g. in air.

There is provided a biologically active surface for an implant, the active surface comprising a silver-substituted calcium phosphate (Ag—CaP) thin film coating which substantially reduces the risk of periprosthetic infection in a first instance and/or is able to substantially eradicate a developing infection in a second instance.

According to some embodiments, in addition to the antimicrobial effect of the silver in the biologically active surface, controlled dissolution of the Ag—CaP coating simultaneously provides an osteostimulation surface for faster bone ingrowth an/or ongrowth depending upon the design of the implant (e.g. ingrowth structure). Therefore, the present invention may benefit the patient by both reducing the potential for infection and promoting osseointegration.

There is provided a formula and/or composition of an antimicrobial/antibacterial thin film coating and an application process thereof. The composition of this coating (i.e., the bulk material) comprises biphasic calcium phosphate (e.g., 70% HA and 30% β-TCP). Silver, fluoride, and/or carbonate may further be incorporated into the 70% HA structure alone or in any combination to form a silver, fluoride, and/or carbonate-substituted apatite material. It is to be understood that other materials, such as bone morphogenic proteins (BMPs), proteins, bioactives, antibacterials, or analgesics, may also be advantageously employed within or adjacent the coating without limitation.

Such an antimicrobial bioceramic may be prepared using a sol-gel process. While the thin film coating is preferably applied to an implant using a dip-coating method to allow penetration deep into porous ingrowth structures, it may alternatively be applied as one or more layers using subsequent processes including, but not limited to, electro-deposition, plasma-spraying, magnetron sputtering, sol-gel, electrostatic spraying, and other biomimetic techniques.

According to some embodiments, there is provided a method of applying an antimicrobial/antibacterial coating to a porous ingrowth structure.

According to some embodiments, there is provided a hydroxyapatite coating comprising a gradient, the gradient comprising varying concentrations of a bone-stimulating agent at different distances from an implant-coating interface.

According to some embodiments, there is provided a hydroxyapatite coating comprising a gradient, the gradient comprising varying concentrations of an antimicrobial/antibacterial agent at different distances from an implant-coating interface.

According to some embodiments, there is provided a hydroxyapatite layer comprising a gradient, the gradient comprising varying concentrations of any one or more of an antimicrobial/antibacterial agent, a bone-stimulating agent, a dissolution-controlling element, a bonding strength increasing element, a protein, a BMP, a bioactive, or an analgesic.

According to some embodiments, there is provided an antimicrobial coating for an implant comprising at least one gradient of varying composition.

Thus, in one embodiment of the present invention there is provided a functionally graded antimicrobial coating for application to the surface or plurality of surfaces of a medical implant comprising:
 a. more than one coating layer comprising or consisting essentially of a bone conducting material, and
 b. an antimicrobial agent in at least one of said more than one coating layer, wherein the concentration of the antimicrobial agent is different in at least two coating layers.

Optionally the bone conducting material is a calcium phosphate material, such as hydroxyapatite and/or β tricalcium phosphate.

As with other embodiments of the present inventions the concentration of the antimicrobial agent is preferably greater in the outer coating layer than in the inner coating layer.

Optionally, the inner coating layer does not contain an antimicrobial agent.

In one embodiment, the antimicrobial agent is or comprises silver, copper, zinc, or any combination thereof. If silver is present, then the maximum silver concentration within the functionally graded coating ranges from about 0.1 to about 10 weight percent, such as from about 0.5 to about 3 weight percent.

In one embodiment, the antimicrobial agent is or comprises an antibiotic including vancomycin, gentamycin, penicillins, cephalosporins, aminoglycoside, macrolides, clindamycin, tetracyclines, chloramphenicol, spectinomycin, polypeptide antibiotics, fluoroquinolones, or any combination thereof. Alternatively, or in addition, the antimicrobial agent is or comprises an anti-fungal including amphotericin B, nystatin, liposomal amphotericin B, flucytosine, or any combination thereof. Alternatively, or in addition, the antimicrobial agent is or comprises an anti-viral including acyclovir, ganciclovir, idoxuridine, amantadin, interferons, azidothymidine, or any combination thereof.

In some embodiments of the present invention, in addition to an antimicrobial agent, at least one of the bone conducting coating layers contains a bone stimulating agent. Such a bone stimulating agent can be carbonate, fluoride, silicon, magnesium, strontium, vanadium, lithium, a growth factor (BMP, etc), a biomimetic peptide, or any combination thereof.

As in other embodiments, the concentration of the bone stimulating agent is different for at least two coating layers.

In some embodiments, the coating further comprising an analgesic agent in at least one layer. Analgesics can be or comprise either local anesthetics, such as bupivacaine (e.g. Marcain, Marcaine, Sensorcaine and Vivacaine), a narcotic analgesic, such as opioids, morphine, codeine, oxycodone (Percodan), levorphanol (levodromoran), propoxyphene (Darvon), and pentazocine (Talwin); and/or is or comprises normarcotic analgesics, such as, acetylsalicylic acid (aspirin), phenylbutazone (Butazolidine), indomethacin (Indocin), acetaminophen, and phenacetin, etc, or any combination thereof.

As with other embodiments, the concentration of the analgesic agent can be different in at least two coating layers.

Optionally, where both types of analgesics are used, a narcotic analgesic is in the outer surface and a normarcotic analgesic is in the inner surface.

In one embodiment of the present invention, the analgesic is contained within a layer further comprising a polymer selected from the group consisting of: PLA, PLGA, PGA, PCL, equivalents thereof, and/or combinations thereof.

According to some embodiments, there is provided an implant having a customized biologically active surface. For example, the implant may be covered with a gradient coating adapted to provide less metal ion release for patients having a metal sensitivity. In another example, the gradient coating may be further optimized to be quickly absorbed at a constant rate or absorbed at different rates over time, depending on the needs of the patient.

In one embodiment, there is provided a medical implant comprising at least one surface, wherein said implant has a coating positioned on at least a part of said at least one surface, said coating comprising a bioactive material and an antimicrobial agent, wherein the concentration of said antimicrobial agent varies with distance from an implant-coating interface.

Optionally, the medical implant has a coating which comprises a number of layers, and wherein the concentration of antimicrobial agent is different in at least two coating layers.

Further, in some embodiments the concentration of antimicrobial agent is greater further from the surface of the implant than nearer to the surface.

In one embodiment, where there are a number of layers of coating, the layer of the coating that is adjacent to the at least one surface of the implant does not contain an antimicrobial agent.

Optionally, the antimicrobial agent is or comprises silver, copper, zinc, or any combination thereof.

In one embodiment, the maximum silver concentration within the coating ranges from about 0.1 to about 10 weight percent, or from about 0.5 to about 3 weight percent. As disclosed herein, the term "weight percent" (wt %) refers to the weight % of the coating, or to a layer of the coating, rather than to the entire weight of the implant+coating.

In other embodiments, the antimicrobial agent is or comprises an antibiotic selected from a group comprising vancomycin, gentamycin, penicillins, cephalosporins, aminoglycoside, macrolides, clindamycin, tetracyclines, chloramphenicol, spectinomycin, polypeptide antibiotics, fluoroquinolones, or any combination thereof.

Alternatively, or as well as, the antimicrobial agent is or comprises an anti-fungal including amphotericin B, nystatin, liposomal amphotericin B, flucytosine, or any combination thereof.

Alternatively, or as well as, the antimicrobial agent is or comprises an anti-viral including acyclovir, ganciclovir, idoxuridine, amantadin, interferons, azidothymidine, or any combination thereof.

In some embodiments, the bioactive material in the coating is a bone stimulating material, such as calcium phosphate, hydroxyapatite, β tricalcium phosphate, a mixture of hydroxyapatite and β tricalcium phosphate, resorbable polymers, bioglass, derivatised phosphate-based compound, orthophosphates, monocalcium phosphates, octacalcium phosphates, dicalcium phosphate hydrate (brushite), dicalcium phosphate anhydrous (monetite), anhydrous tricalcium phosphates, whitlocktite, tetracalcium phosphate, amorphous calcium phosphates, fluoroapatiete, chloroapatite, non-stoichiometric apatites, carbonate apatites, biologically-derived apatite, calcium hydrogen phosphate, calcium hydrogen apatite, water insoluble ceramics, phosphates, polyphosphates, carbonates, silicates, aluminates, borates, zeolites, bentonite, kaolin, and combinations thereof.

Optionally, the bone stimulating material contains calcium, phosphate, carbonate, fluoride, silicon, magnesium, strontium, vanadium, lithium, a growth factor (BMP, etc), a biomimetic peptide, or any combination thereof.

In an embodiment of the present invention, the concentration of the bone stimulating material varies with distance from an implant-coating interface.

In various embodiments of the present invention, the bone stimulating material can be hydroxyapatite and/or β tricalcium phosphate.

In a further embodiment of the present invention, the coating can further comprises an analgesic agent. Optionally, the analgesic agent comprises one or more local anesthetics, such as bupivacaine (e.g. Marcain, Marcaine, Sensorcaine and Vivacaine), narcotic analgesic, such as opioids, morphine, codeine, oxycodone (Percodan), levorphanol (levodromoran), propoxyphene (Darvon), and pentazocine (Talwin); and/or one or more non-narcotic analgesic, such as, acetylsalicylic acid (aspirin), phenylbutazone (Butazolidine), indomethacin (Indocin), acetaminophen, and phenacetin, etc, or any combination thereof.

As with other embodiments, the concentration of the analgesic agent can vary with distance from an implant-coating interface.

Further, if both types of analgesics are used then the narcotic analgesic is preferably in the outer surface of the coating and the normarcotic analgesic is in the inner surface of the coating.

The biologically active implant surface of the present invention may provide significant advantages over the prior art. First, the implant surface may generally inhibit a broad-spectrum of bacterial activity. Second, the implant surface may be adapted to substantially eradicate bacterial activity when an infection develops. Third, in some embodiments, the implant surface may further promote faster bone ingrowth and accelerated osseointegration.

The biologically active implant surface, in some embodiments, may at least partially safeguard against partial exposure of the implant due to shear-off. This is a significant improvement over the prior art because previously portions of the antimicrobial/antibacterial/infection-reducing agent could be sheared off during implantation, thereby leading to uncovered areas that may render the implant open to bacterial attack. The present invention aims to solve this problem by incorporating a gradient HA coating that possesses improved bonding characteristics adjacent an implant-coating interface, while still delivering improved infection resistance and, in some embodiments, promoting osseointegration.

There is also provided a sol-gel dip coating method. The sol-gel dip coating method provides the advantage of being cost efficient as compared to most line-of-sight processes, such as plasma spraying, PVD, and IBAD, etc. The sol-gel dip coating is also preferable for use with ingrowth structures due to its pore-filling capability.

In one embodiment of the present invention there is provided a medical implant having at least one surface and a coating thereon, wherein said coating comprises one or more layers and wherein the bonding strength at each layer interface decreases with distance from an implant-coating interface.

In a further embodiment, there is provided a medical device having at least one surface and a coating at least partly covering said at least one surface, wherein the coating is configured such that it allows the elution rate of each of the agents within the coating to be controlled.

In yet a further embodiment of the present invention, there is provided a method of reducing the risk or preventing infection after a surgical procedure, said method comprising utilizing a medical implant as disclosed herein during the surgical procedure such that on completion of the surgical procedure the implant is retained in situ at the site of the procedure.

Also disclosed is the use of an implant as discussed herein for the reduction or prevention of infection after a surgical procedure.

In one embodiment of the present invention, the implant is one than can be used during dentistry, orthodontic, orthopaedic work etc., and on a larger scale for e.g. joint replacements.

Further areas of applicability of the invention will become apparent from the detailed description provided hereinafter. It should be understood that the detailed description and specific examples, while indicating the particular embodiment of the invention, are intended for purposes of illustration only and are not intended to limit the scope of the invention.

BRIEF DESCRIPTION OF THE DRAWINGS

The accompanying drawings, which are incorporated in and form a part of the specification, illustrate some embodiments of the present invention and together with the written description serve to explain some of the principles, characteristics, and features of the invention. In the drawings.

DETAILED DESCRIPTION OF THE EMBODIMENTS

The following description of the depicted embodiment(s) is merely exemplary in nature and is in no way intended to limit the invention, its application, or uses.

Figure 1:
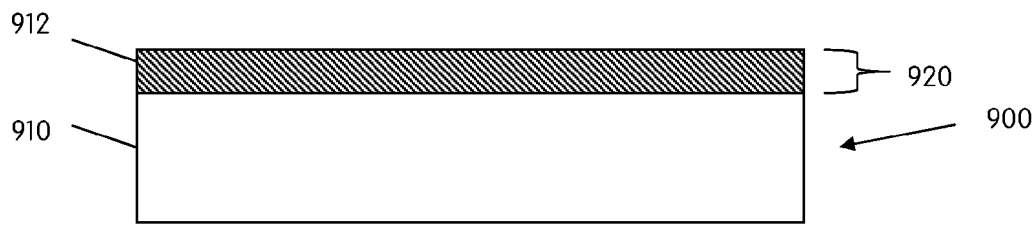
FIG. 1 is a schematic of a conventional implant of the prior art having antimicrobial properties.

Referring to the accompanying drawings, FIG. 1 represents a coated implant (900) of the prior art. A hydroxyapatite coating (920) is normally applied to an implant substrate (910) and sintered thereto in a conventional manner. Such a coating may comprise a mixture layer (912) of hydroxyapatite and a silver additive for an antimicrobial effect. The silver additive is not homogeneously incorporated into the HA lattice crystal structure.

Figure 2:
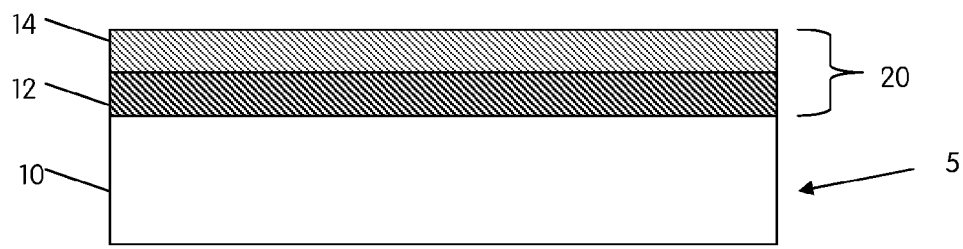
FIG. 2 is a schematic of an implant having improved antimicrobial and fixation properties.
Figure 3:
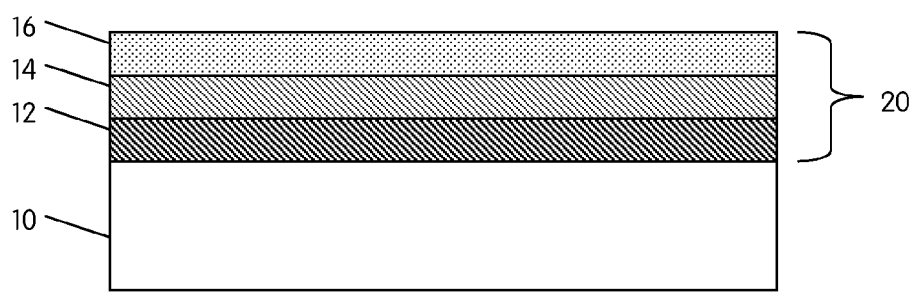
FIG. 3 is another embodiment of an implant of the present invention.
Figure 4:
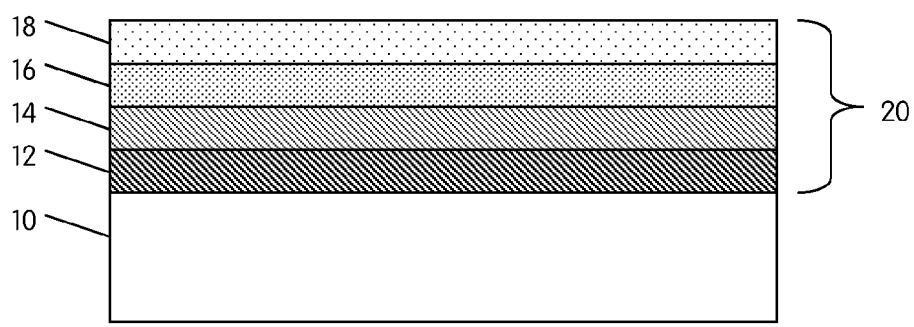
FIG. 4 is yet another embodiment of an implant of the present invention.

Referring to FIGS. 2-4, there is provided an implant (5) having an implant substrate (10) having a coating (20) with a composition gradient. The gradient is generally composed of at least two portions having a different chemical/material composition. The gradient may be configured to increase the bond strength of the coating nearest an implant-coating interface, or the gradient may be configured such that an infection-reducing agent in the coating (20) is more prevalent on an outer surface (18) than an inner surface (12, 14). As an example, the coating (20) may be an antimicrobial hydroxyapatite coating. The implant substrate (10) may be comprised of any number of biocompatible materials. As examples, the implant substrate (10) may be selected from a biocompatible material known in the art such as cobalt chromium, zirconium, titanium, stainless steel, ceramic, PEEK, polyurethane, etc. The skilled person will realize that other suitable substrate materials may be utilized without limitation.

The coating (20) comprises a first layer (12) having a first composition and at least one other second layer (14) having a second composition. In some embodiments, the first layer (12) may be formed with a composition more compatible with the material of the implant substrate (10) for improved bonding characteristics and resistance to shear-off/delamination during press fit. For example, the first layer (12) may be comprised of substantially pure HA. Alternatively, in other embodiments, the first layer (12) may be formed with a composition having a higher content of bone-stimulating agents than the second layer (14). Such bone-stimulating agents may be any one or more of, but not limited to, fluoride, calcium, BMPs, proteins, bone void fillers, absorbable materials, and bioactives.

In other embodiments, it may be desirable to provide the second layer (14) with a composition having more infection-reducing agents than the first layer (12) because the greatest risk of infection generally occurs within the first few weeks after surgery. In doing so, the coating (20) provides a strategic "time-release" of an antibacterial agent to provide the greatest anti-infection effect during initial bone remodeling. Such infection-reducing agents may be selected from any one or more of the following: copper, zinc, silver, gold, other metals having antimicrobial effects, or antibacterials, such as vancomycin. It should be understood that other materials may also be used.

Additions of carbonates or other dissolution-controlling materials may be added to each layer in predetermined quantities to control the sequential decomposition rate of the HA coating (20) over time. For instance, it may be desired to allow outer layer (14) to absorb and deteriorate quickly, thereby allowing a burst release of silver ions adjacent the bone interface to fight off and inhibit infection during the most critical days after surgery. Inner layer (12) may be provided with a low carbonate content to achieve a slower, less dramatic release of silver ions in vivo for maintenance and infection-preventative purposes during the less critical period after early post-operative recovery. Moreover, inner layer (12) may be provided with more additives for encouraging bone growth than an outer layer (14) because there may be some delay in bone reformation soon after surgery.

In some embodiments, the coating (20) provides both a way to selectively control the release of ions over time to combat infection. The coating (20) also may selectively control the exposure and release of bone-stimulating agents over time to improve biologic fixation and ingrowth. Further, the coating (20) may provide a sacrificial layer of an antimicrobial coating so as to ensure that the entire implant remains coated, even if some of the coating shears off during implantation. Hence, the coating (20) may provide full bone ingrowth/ongrowth/biologic fixation to occur without the threat of infection.

Referring now to FIGS. 3 and 4, there is provided an implant (15) having the substrate (10) provided with the antimicrobial coating (20) comprised of at least three layers (12, 14, 16, 18). Each layer (12, 14, 16, 18) may be composed of different compositions, or the layers may be formed with alternating compositions. In some embodiments, each layer (12, 14, 16, 18) has an amount of an antimicrobial and/or antibacterial agent that is effective at guarding against infection or otherwise killing bacteria which have formed during or after surgical implantation. Moreover, each layer (12, 14, 16, 18) may be provided with an optimum content level of bone-stimulating agents.

Each layer (12, 14, 16, 18) of the antimicrobial coating (20) may be applied to any portion of the implant substrate (10). The substrate (10) may be a core material, or the substrate (10) may be a separate ingrowth structure of similar or dissimilar material bonded to a core material. Such an ingrowth structure may be any one or more of, but not limited to, a porous structure, sintered beads, sintered particles of nonspherical shape, metal reticulated foam structures, fiber metal mesh, porous plasma spray, etc.

The manner in which the layers (12, 14, 16, 18) are applied to the substrate may vary. Some examples of acceptable application methods are hot-dipping, electro-deposition, plasma-spraying, magnetron sputtering, sol-gel, electrostatic spraying, and low temperature solution precipitation biomimetic techniques. It will be appreciated that application methods may be alternated between layers of the gradient coating of the present invention. For instance, a sol-gel dip process may be used to apply the first inner layer (12), electro-deposition may be used to apply the second layer (14), and plasma-spraying may be used to apply the third layer (16). It will also be appreciated that any number of layers (12, 14, 16, 18) may be incorporated into the coating (20) in order to provide the optimum release of antimicrobial and bone-stimulating agents.

The concentration gradient of coating (20) may be achieved by sequentially applying different solutions to the substrate (10) to form individual layers (12, 14, 16, 18), each layer corresponding to a single application of solution, at least two of the layers (12, 14, 16, 18) having dissimilar concentrations of any one or more of a bone stimulating agent, an infection-reducing agent, a catalyst for controlled release of the agents, or other material such as a protein, BMP, bioactive, antibiotic, or analgesic. For example, the silver or zinc content may be higher in an outer layer (18) than in an inner layer (12), wherein the average silver or zinc content gradually changes in concentration over any intermediate layers (14, 16) therebetween. Likewise, the protein or carbonate content in an outer layer (18) may be greater than or less than an inner layer (12). Additionally, if desired, fluoride content may gradually increase from an outer layer (18) to an inner layer (12).

Figure 5:
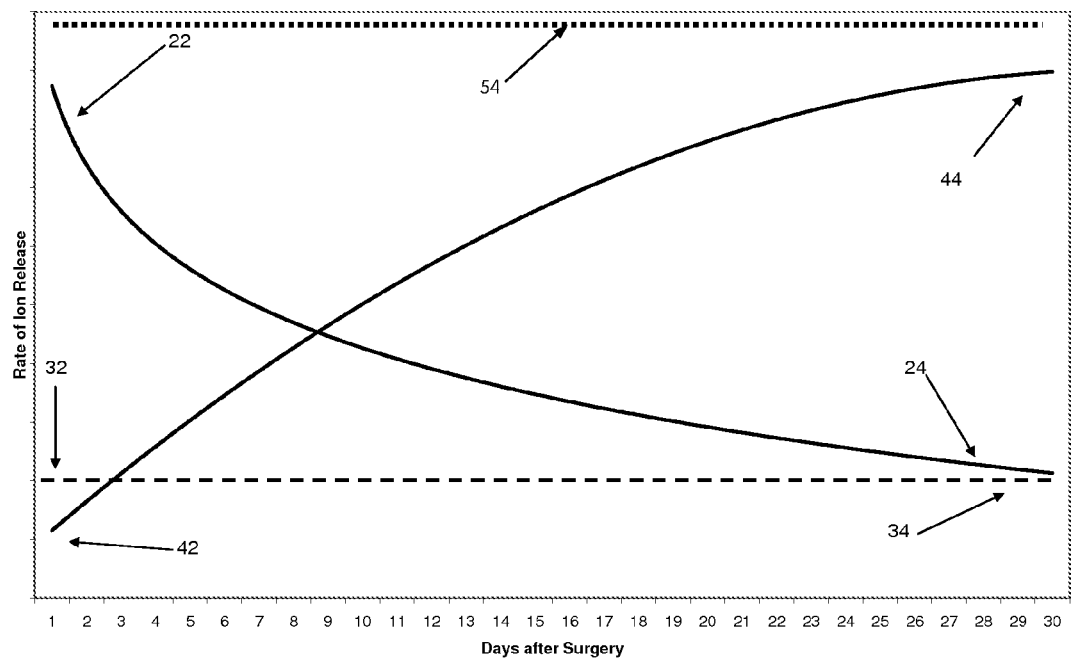
FIG. 5 is a graph of controlled ion and agent release rates over time.
Figure 6:
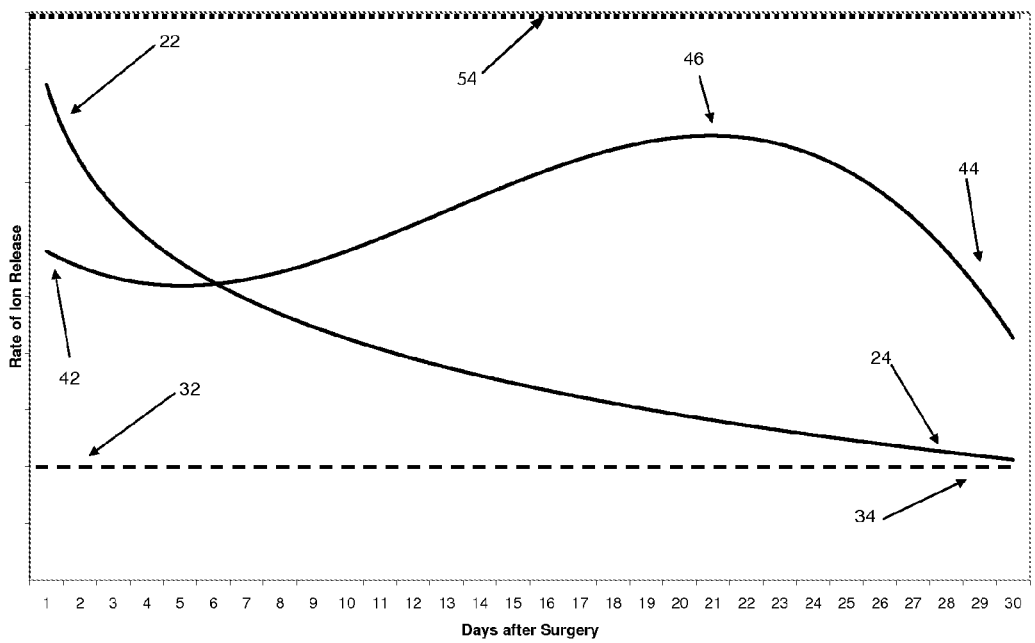
FIG. 6 is another graph showing alternative ion and agent release rates over time.
Figure 7:
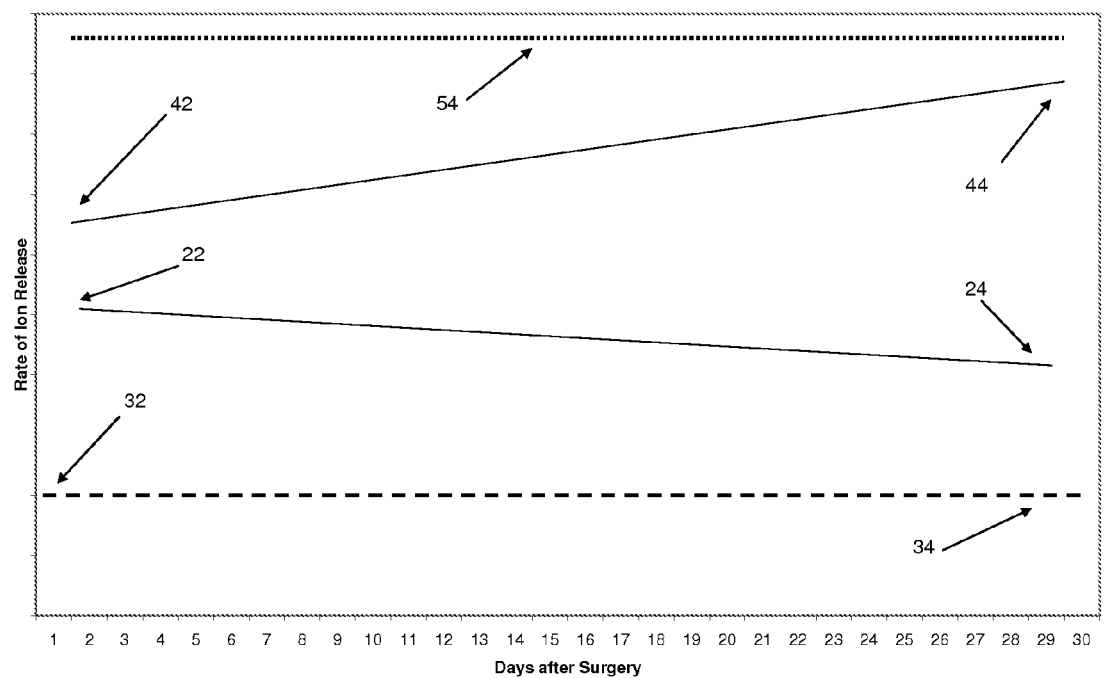
FIG. 7 is yet another graph showing alternative ion and agent release rates over time.

Referring now to FIGS. 5-7, the predetermined release rate of infection-reducing ions over time may be advantageously controlled so as to avoid over-exposure of the ions to a patient, while still providing maximum protection against infection. Such a predetermined release rate may be optimized using simple experimentation so as to provide the most effectiveness in preventing infection without compromising ingrowth and long term ion release. The predetermined release rate of osseoinductive agents may further be designed so as to ramp up several days after surgery, when the risk of infection may be reduced relative to the immediate post-operative period.

Turning to FIG. 5, it can be seen that the initial ion release rate for the antimicrobial agent (22) is greater than a minimum initial ion release rate (32) necessary to provide sufficient anti-infection properties. For example, numeral identifier (22) may represent the silver ion release rate of the outer layer (18) of the HA coating (20), and numeral identifier (32) may represent the minimum initial silver ion release rate necessary to effectively kill bacteria, reduce infection, and/or prevent future infection. The initial ion release rate for the antimicrobial agent (22) may be high as shown so as to provide a "burst release" to kill any existing bacteria during and immediately after surgery. The initial ion release rate for the antimicrobial agent (22) may then decrease over time to a lower, safer ion release rate (24) for infection-prevention maintenance and to prevent new bacteria from forming. It is preferred that the lowest ion release rate (24) of the coating (20) remains greater than or equal to the minimum ion release rate (32, 34) necessary to maintain a reduced risk of infection, at least for a time period following surgery. This minimum ion release rate (32, 34) may be determined by finding the greatest minimally inhibitory concentration (MIC) value for a bacteria group of which the patient is at risk for exposure during a particular surgery. MIC is generally defined herein as the lowest concentration of an antimicrobial agent that will inhibit the visible growth of a particular microorganism after incubation overnight. The concentration of an antimicrobial agent which may be present in one or more layers (12, 14, 16, 18) of the gradient coating (20, 80, 120, 2000) of the present invention is preferably greater than the largest MIC for its bacterial counterpart. It is also preferred that the release rate (22, 24) stay below human toxicity levels (54) to ensure that a patient is not overexposed to the heavy metal ions or other antibacterial agents. Surgeries take place in different geographical locations of the world have different postoperative infection-causing bacteria groups, and, therefore, the types and levels of antimicrobial agents within the gradient coating (20) may vary accordingly.

It should be understood that all release rates may generally be controlled by altering the concentration gradient in the HA coating (20). The ion release period may be shortened by: (1) accelerating HA degradation using a carbonate or other dissolution catalyst; (2) decreasing the thicknesses of the layers (12, 14, 16, 18) in the coating (20); (3) decreasing the number of layers (12, 14, 16, 18) within the coating (20); and/or (4) increasing the change in concentration of agents between layers in such a way that agent release diminishes soon after the initial burst release (22).

In addition to antimicrobials, bone-promoting agents, such as fluoride and calcium, may be provided. Reference numeral (42) indicates an initial release rate of a bone stimulating agent that promotes osseointegration. This initial release rate (42) may be high or low, depending on the individual patient's needs. In the embodiment illustrated in FIG. 5, the release rate of a bone stimulating agent increases from initial rate (42) to a maintenance rate (44), at which point it levels off to promote osseointegration at a constant level.

FIGS. 6 and 7 show alternative release rates for the most-preferred coating additives over time. FIG. 6 shows one embodiment where bone-promoting agents are initially released at a high rate (42), which increases to higher rate (46), and then decreases and levels off at maintenance rate (44). FIG. 7 shows another embodiment in which the rate of release of a bone-promoting agent (42, 44) is always greater than the release rate of antimicrobial agents (22, 24). For instance, an outer layer (18) of a gradient coating (20) may initially provide a burst release rate of fluoride bone-stimulating agents (42) that is greater than the initial release rate of silver ion antimicrobial agents (22). As mentioned above, it is preferred that the lowest release rate of anti-infection agents (22, 24) remains greater than or equal to the minimum release rate (32, 34) sufficient for reducing the risk of infection. It is to be understood that substances other than bone-promoting agents, antimicrobial, and/or antibacterial agents may be present in any one of layers (12, 14, 16, 18) of the HA coating (20). It is therefore anticipated that additional controllable release rates (not shown) may be utilized.

Figure 8:
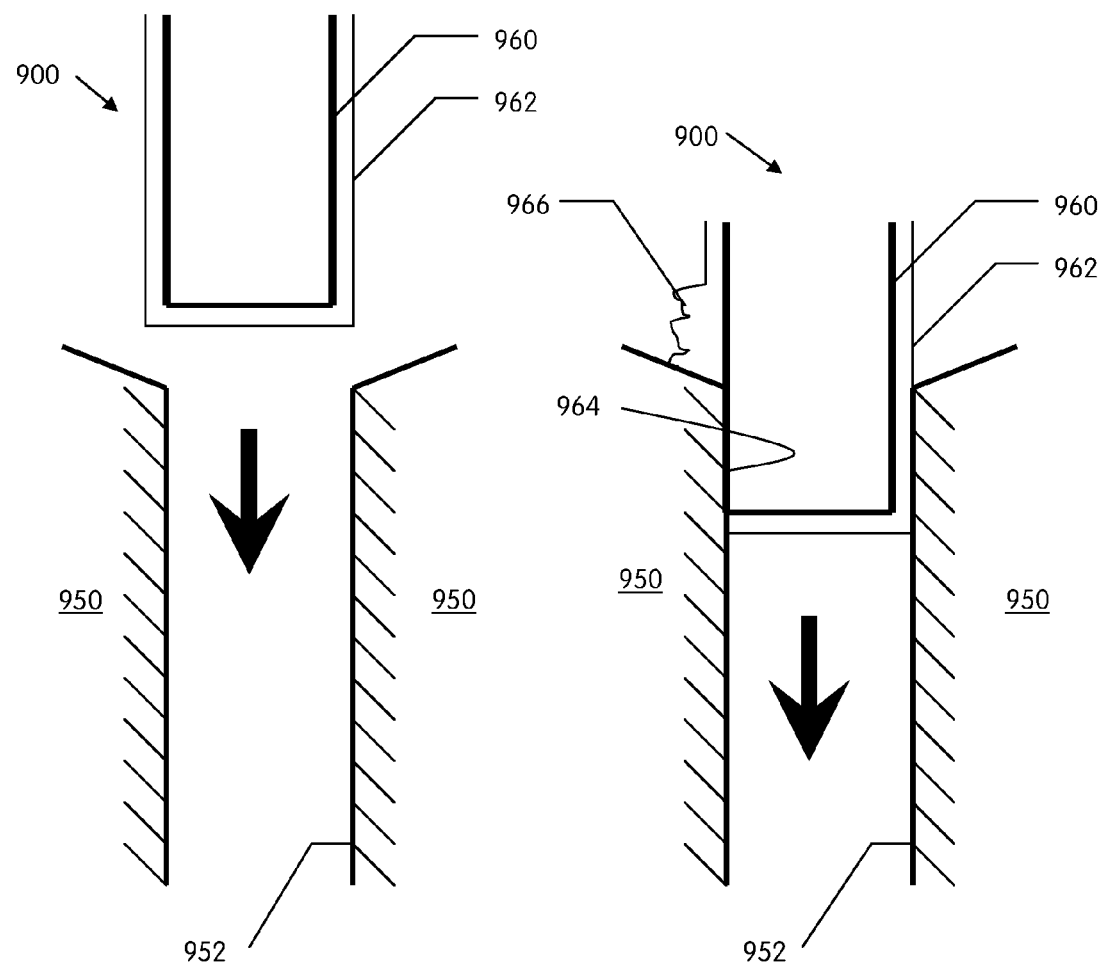
FIG. 8 demonstrates a drawback of using a conventional implant of the prior art having antimicrobial properties.

Referring to FIG. 8, prior art coatings such as that shown in FIG. 1, may be vulnerable to shearing off of an implant substrate when implanted into a bony structure (e.g., a femoral stem implanted into a prepared femoral canal) because the silver additive may lessen the bonding strength of the layer (912). A bone (950) is prepared to form a bony surface (952) suitable for scratch fit with the implant (900). Normally, for cementless fixation, the bony surface (952) is dimensioned so as to provide an interference press fit with the implant (100) to provide initial stabilization. The implant (900) generally consists of a core substrate (960) and a single composition coating (962), such as a hydroxyapatite coating with a silver additive. When the implant (900) is inserted into the bone (950), the coating (962) of the implant is susceptible to shearing. Shearing is disadvantageous because if any material (966) from the coating (962) is removed from the core substrate (960), it may leave a portion (964) of the core substrate (960) exposed and more susceptible to infection. Furthermore, any portion (964) of the core substrate (960) that is left without a coating (962) may exhibit reduced bone ingrowth due to a lack of hydroxyapatite in the portion (964).

Figure 9:
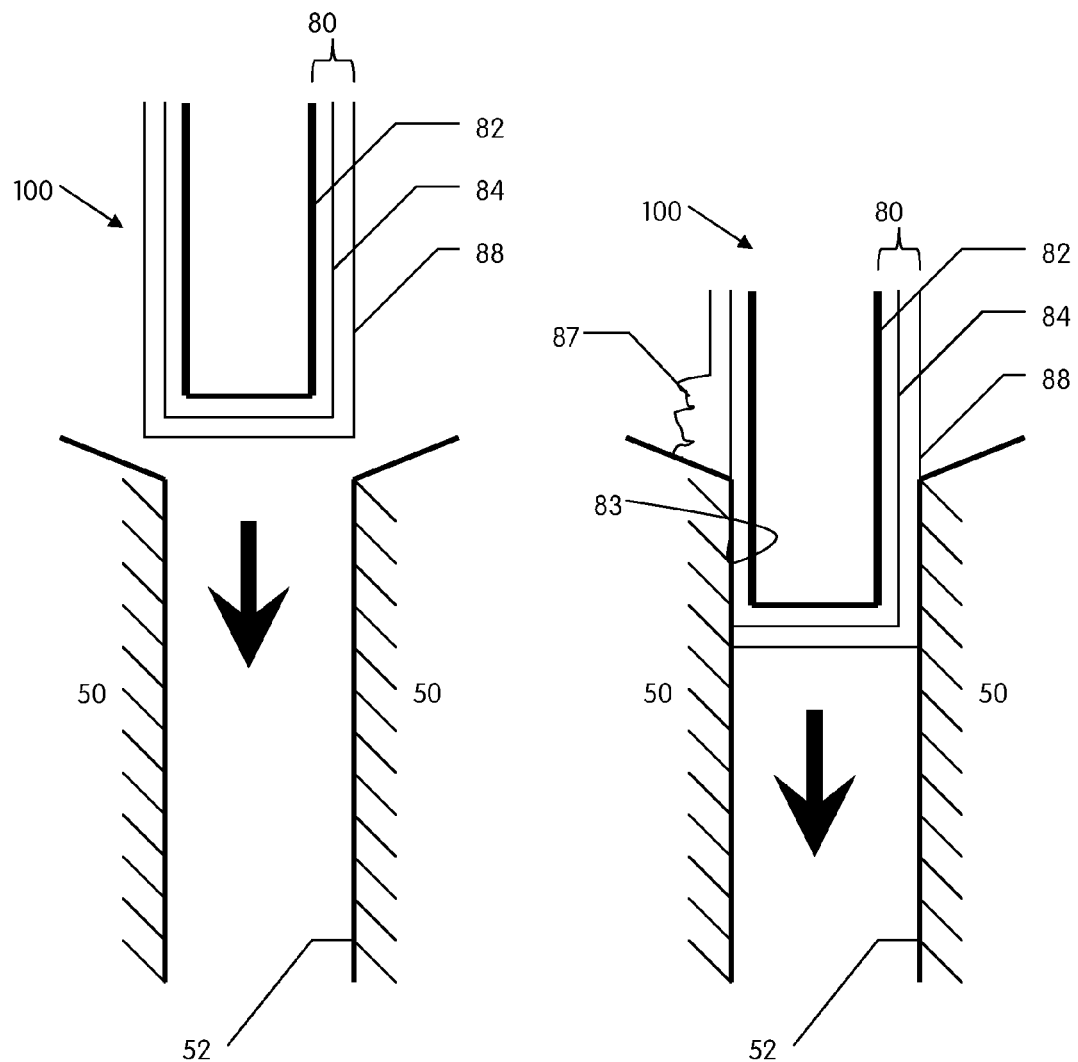
FIG. 9 demonstrates one possible advantage of using an implant of the present invention.

Turning to FIG. 9, a coated implant (100) having a gradient coating (80) is shown to have improved antimicrobial and osseointegration characteristics over prior art implants using conventional coatings. The gradient coating (80) shown in FIG. 9 is applied to an implant substrate (82) of the implant (100) and comprises at least two layers (84, 88) that are generally formed of different compositions. In some embodiments, an outer layer (88) has a higher metal content than at least one inner layer (84). In other embodiments, however, the at least one inner layer (84) may exhibit an equal or greater amount of metal than the outer layer (88). The metal may be selected from one or more of silver, zinc, copper, or other known metals having antimicrobial effects. Moreover, antibiotics, such as vancomycin and/or penicillin, may be utilized.

The at least one inner layer (84) may be free of metal or may comprise a metal different than the outer layer (88). For example, the at least one inner layer (84) may comprise a low concentration of zinc, whereas the outer layer (88) may comprise a lower, equal, or greater concentration of another metal, such as silver. Alternatively, the outer layer (88) may comprise a first zinc and silver concentration, whereas the at least one inner layer (84) may exhibit a second silver and/or copper concentration. Different gradient coating (80) configurations are possible and one of ordinary skill in the art is able to readily modify the additives and compositions of each layer (12, 14, 16, 18, 84, 88) of the gradient coating (20, 80) to satisfy the needs of a patient on an individual basis. It also should be understood that at least one inner layer (84) may comprise any number of layers, each of which may have similar or different compositions and/or additives.

The at least one inner layer (84) and/or outer layer (88) may further comprise at least one bone-stimulating agent, such as fluoride or calcium. The concentration of the bone-stimulating agent in the at least one inner layer (84) may be greater than, equal to, or less than that of the outer layer (88). However, it is preferred that the at least one inner layer (84) has a greater concentration of bone-stimulating agent than the outer layer (88).

The outer layer (88) may be advantageously utilized as a protective layer so as to allow at least one or more inner infection-reducing layers (84) to remain bonded to the implant substrate (82) after implantation. For instance, a coated implant (100) may be press-fitted into a prepared bony surface (52) of a bone (50) to provide initial stabilization. Press-fitting is normally achieved by impacting the implant (100) so as to form an interference fit with the prepared bony surface (52). Often, because the prepared bony surface (52) is dimensioned so closely to the implant, or slightly smaller than the implant, there is a possibility that at least some coating material (87) may shear off of or be displaced from the outer layer (88) thereby forming an outer layer deficient zone (83) of very thin or no outer layer (88). One unique aspect of the present invention is that because the coating is formed as a gradient coating (80), the at least one outer layer deficient zone (83) is still protected by an underlying at least one inner layer (84) having infection-resistant properties and/or higher bonding strength characteristics. Any displaced material (87) may serve as a "barrier" to prevent bacteria from entering the bone-implant interface (52) and/or promote local fixation.

Another unique aspect of the present invention is that inner layer (84) may be formulated with a composition that possesses improved bonding characteristics with an implant substrate (82). Using the outermost layer (88) as a "first defense" protective antimicrobial layer and the at least one inner layer (84) as a backup antimicrobial layer allows for some margin for shear during implantation, while still maintaining one-hundred percent coverage of the implant substrate (82) with the antimicrobial properties necessary to kill and prevent formation of bacteria. In this respect, the gradient coating (80) may comprise a bonding strength gradient, such that the coating composition gradually increases in bonding strength from the outermost surface (88) to the implant substrate (82), wherein the greatest bond strength is preferably achieved at the coating-substrate interface (117, FIG. 10). This bonding strength gradient may be achieved by adding substrates to the at least one inner layer (84) which are most compatible with the material of the implant substrate (110). The addition of such substrates may be controlled independently of the antimicrobial agents, bone-stimulating agents, and/or dissolution catalysts discussed herein. Alternatively, materials known to have good bonding characteristics with implants, such as pure HA, may be utilized in the layer (112) most adjacent to the implant substrate (110).

Figure 10:
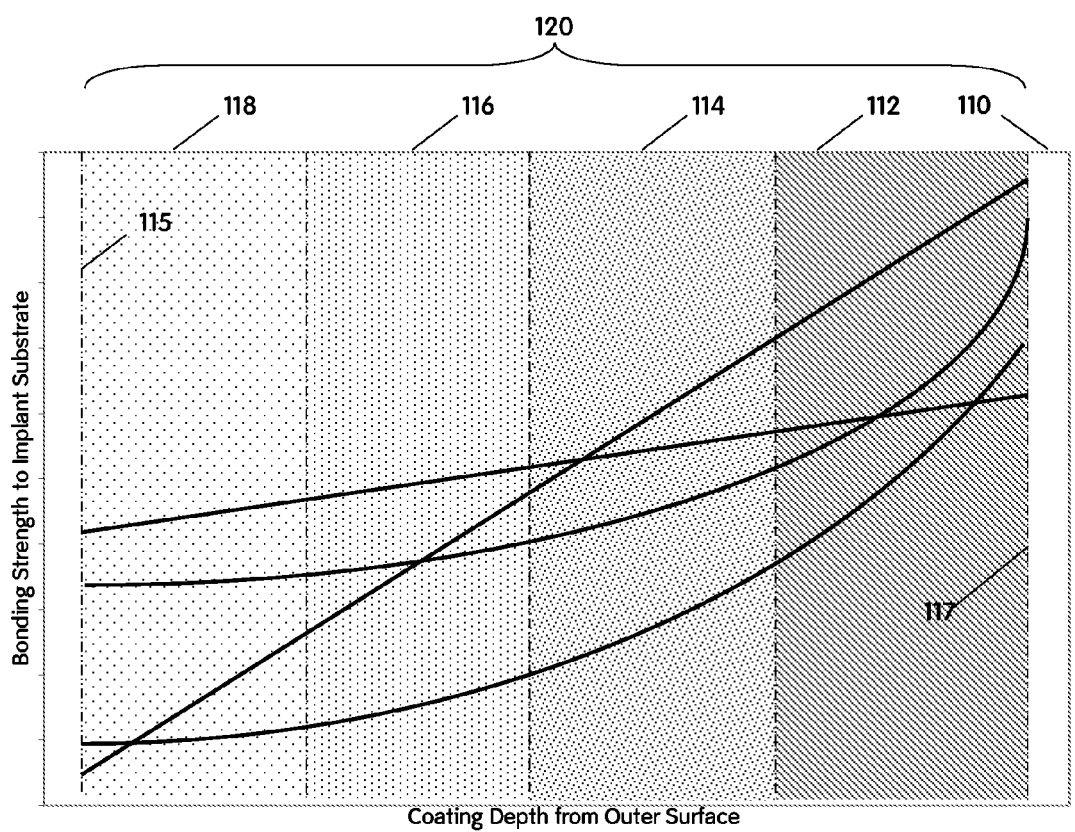
FIG. 10 shows bonding strength gradients in a coating of the implant.

FIG. 10 illustrates four possible examples of bonding strength gradients. As shown, the average bonding strength of the gradient coating (20, 80, 120) may generally increase with coating depth. This allows for some external coating shear to take place without exposing the implant substrate (110). For instance, the bonding strength of the coating composition near an outside surface (115) of a gradient coating (120) may be less than at the implant-coating interface (117) of a substrate or ingrowth structure (110). In other words, layers (112) and (114) may comprise a composition having greater bonding characteristics with the material of the substrate (110) than layers (116) and (118), in order to optimize bonding at the implant-coating interface (117). As discussed in detail above, the inner layers (112, 114) may be configured with a higher concentration of bone-stimulating agents than layers (116, 118) for improved osseointegration with the implant substrate or ingrowth structure (110). The outer layers (116, 118) may be provided with a higher concentration of ion-producing antimicrobials such as silver, zinc, or copper-based elements.

Figure 11:
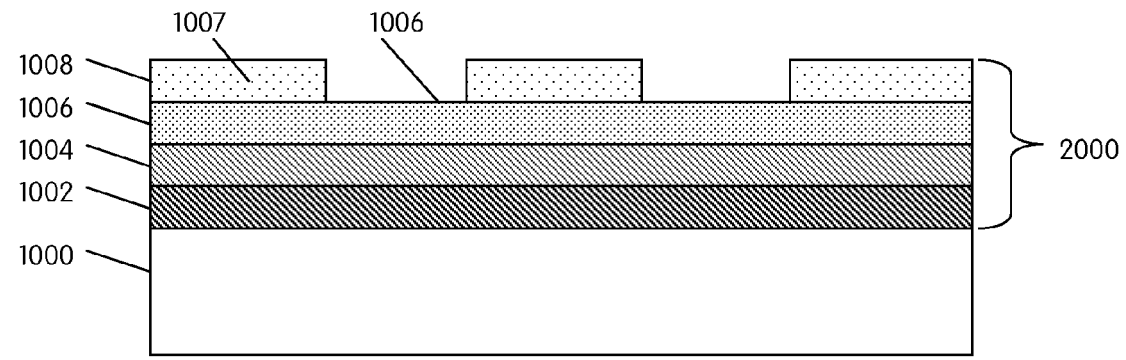
FIG. 11 is a schematic of an embodiment of the implant having at least one discontinuous layer.
Figure 12:
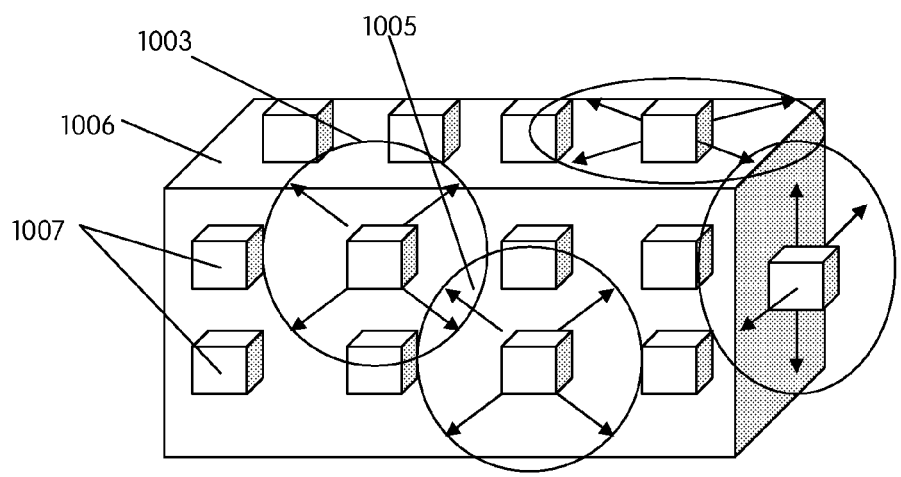
FIG. 12 is another schematic view of FIG. 11, showing an embodiment having at least one discontinuous layer.

Referring now to FIGS. 11 and 12, any layer (1002, 1004, 1006, 1008) within a multi-layer gradient antimicrobial coating (2000) may include discontinuous layer portions (1007). For example, an outer layer (1008) of coating (2000) may comprise a discontinuous "speckled" coating formed from layer portions (1007). These layer portions (1007) may be strategically placed within the coating (2000) such that the inhibitory zones (1003) for each of the layer portions (1007) overlap (1005). In doing so, the amount of antimicrobial and/or antibacterial agents used in the coating (2000) may be decreased, thereby minimizing patient exposure, while still maintaining adequate protection against infection. Providing layer portions (1007) may further serve to increase the surface texture/roughness of the coating (2000).

Synthesis

The antimicrobial bioceramic gradient coating may be prepared using a sol-gel process. At least three silver concentrations have been prepared and evaluated for use, in order to determine the minimum preferred silver content for any one layer (12, 14, 16, 18). Each silver concentration was calculated based on the Ag/Ca ratio, which may be 0.1, 0.01, or 0.001. Other silver contents were chosen to cover a broad range of silver concentrations in order to determine the minimum silver content in the coating to have a sufficient antibacterial effect but not so high as to inhibit or kill tissue cells, such as osteoblasts. The optimum range of silver concentration has been determined based on both in vitro and in vivo results. To test the antimicrobial effectiveness for a given silver concentration, an equivalent weight (0.05 g) of five powders, each powder having a different silver concentration were tested in a minimum bactericidal concentration (MBC) test against Staphylococcus aureus bacteria. Results showed that all powders containing silver were at least somewhat active in killing and preventing bacteria. Powders having an equivalent silver concentration achieved similar MBC.

Referring to Table 1, the silver concentration of samples 2 and 4 was approximately twenty times greater than the silver concentration of samples 1 and 3. This resulted in an MBC approximately four times greater for samples 2 and 4 than the MBC of samples 1 and 3. In all instances, powders having a silver concentration greater than or equal to about 0.1% were deemed to be capable of killing S. aureus at 105 cfu/ml.

TABLE 1

| Sample | Amount of powder | Silver concentration | MBC (µg/ml) |
| --- | --- | --- | --- |
| 1 | 0.05 g | 0.1% Ag | 6250 |
| 2 | 0.05 g | 2.2% Ag | 1563 |
| 3 | 0.05 g | <0.1% Ag | 6250 |
| 4 | 0.05 g | 1.9% Ag | 1563 |
| 5 | 0.05 g | 0% Ag (HA alone) | N/A |

Figure 13:
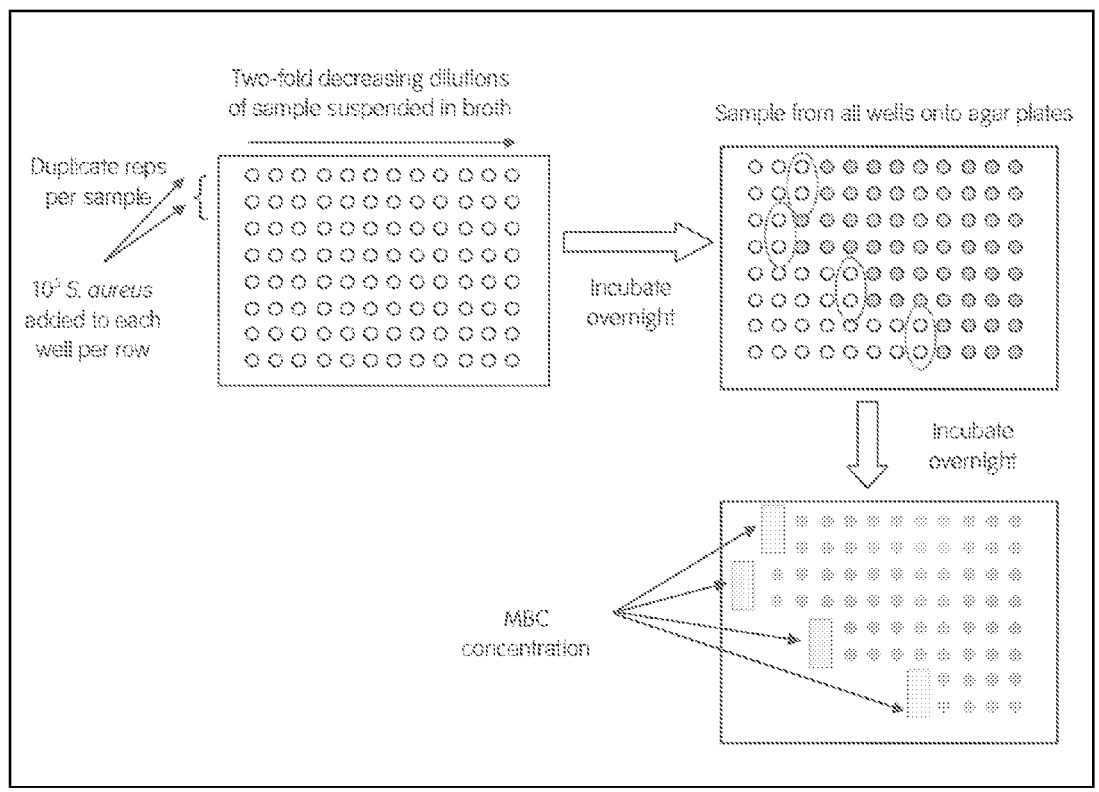
FIG. 13 shows a process of determining the antimicrobial effect of an agent.

FIG. 13 illustrates the process used in testing the sample powders. The bacteria is added to each well per row. A two-fold decreasing dilutions of sample is suspended in broth. The tray is incubated overnight. Samples from each well are placed on agar plates. The samples are again incubated overnight. The MBC is identified for each sample.

Preferably, the Ca/P ratio is kept at 1.60 to prepare 70% HA and 30% β-TCP biphasic calcium phosphate (BCP). It is to be understood; however, that this ratio may be varied to obtain different biphasic HA/β-TCP compositions. β-TCP is generally desirable during the initial bone healing process, because it provides calcium ions that accelerate bone ingrowth.

In addition to silver, fluoride also may be incorporated in the HA composition in order to create fluoride ions/fluorine, which are known to favorably promote mineralization and faster osseointegration. The fluoride may be introduced into a coating alone such that the coating has a concentration gradient of only fluoride, or the fluoride may be introduced into a coating in combination with other elements and agents disclosed herein. A suitable fluoride concentration may be calculated based on $F^-/PO_4^{3-}$ ratio, which is 0.2. Moreover, a carbonate function group may be added to the HA structure, the carbonate function group preferably being designed to strategically destabilize and degrade the HA structure in such a way as to optimally release Ag, Ca, and F ions. In this respect, the carbonate function group generally serves as a mechanism for controlling the rate of Ag, Ca, and F ion release in vivo. The carbonate content may be calculated based on the ratio of $CO_3^{2-}/PO_4^{3-}$, which is 1; however, this content may vary.

In one particular embodiment, the method steps involved with synthesizing the antimicrobial thin film coating generally include first dissolving calcium nitrate and silver nitrate into de-ionized distilled water to form a first solution ($DDH_2O$). Next, ammonium dihydrogen phosphate is dissolved into the first solution ($DDH_2O$) to form a second solution. The appropriate amount of ammonium fluoride and ammonium carbonate is then subsequently dissolved into another ammonium dihydrogen phosphate solution to form a third solution. Concentrated ammonium hydroxide is used to increase the pH levels of both the second and third solutions to about 11. The second calcium nitrate-based solution is slowly added to the third ammonium dihydrogen phosphate-based solution under vigorous stifling. The sol-gel solution is stirred for 24 hours and then allowed to age at room temperature for 2 days. This aged solution may then be applied to an implant via a thin film dip coating or be prepared for use in an antimicrobial powder.

Dip Coating

Preferably, implants utilizing the antimicrobial coating are dipped into the sol-gel solution and then gradually withdrawn vertically at a controlled rate. In one embodiment, the withdrawal rate is about 30 cm/min; however, it should be noted that this rate may be increased or decreased to provide the desired thickness. In addition to adjusting the withdrawal rate, the thickness of the coating may also be controlled by varying the overall viscosity of the sol-gel solution. While any number of dips may be required, a total of 3-4 dips has been shown to produce a preferred coating thickness about 1-2 µm.

Heat Treatment

The thin film coating may be sintered to an implant using a vacuum furnace, an in-air muffle furnace, or any other equivalent devices for sintering known in the art. Preferably, a temperature of about 400-800 degrees C. is held for about 10-30 minutes, although other temperatures and times may be required depending on the composition of the coating and its thickness. After sintering, the furnace is cooled to room temperature. Crystallinity and/or the composition of the coating, which affects resorption rate, may be controlled by varying the sintering temperature. For example, a lower sintering temperature generally results in a more degradable coating, and biphasic calcium phosphate can only be developed at temperatures above about 750 degrees C.

There are many different embodiments which may be practiced with the present invention.

In one embodiment, there is provided an antibacterial thin film coating applied to an implant by way of an antimicrobial bioceramic powder. To produce such an antimicrobial bioceramic powder, an aged sol-gel solution is dried at about 90 degrees C. for about 48 hours and then sintered between about 400-800 degrees C. for about 1-2 hours. The resulting substance after sintering may then be ground into powder and sieved and sorted by size for different applications. In some instances, coarser powders may be used to make dense bulk antibacterial bioceramics or porous scaffolds. In other instances, finer powders may advantageously be used as feeding powders for plasma-sprayed HA coatings. The antimicrobial bioceramic powder may have many valuable uses and may come in many forms.

In another embodiment, there is provided a coating for a medical implant configured for reducing infection and promoting biologic fixation, the antimicrobial coating comprising a gradient. Such a gradient may comprise, for example, a change in composition or a variation in content of at least one substance with respect to coating depth. In one particular instance, the antimicrobial coating may provide an initial burst release of the antimicrobial agent at a bone-coating interface by having a higher concentration of silver additive at an exterior portion of the coating.

In another instance, the antimicrobial coating may provide a predetermined controlled release of fluoride over time in order to optimally promote bone ingrowth and biologic fixation.

In yet another instance, the antimicrobial coating may provide a sustained preventative level of ion release that is greater than or equal to the minimum level required to have an effective antibacterial effect.

In still another embodiment, there is provided a coating for an implant having a concentration gradient of pain reducers or analgesics. The gradient may be configured for an initial burst release of a pain reducer or analgesic, followed by a slow release of the pain reducers or analgesics, although actual release rate may vary to address the needs of an individual patient or patient population subset. Such a pain-reducing element gradient within a coating may be present alone or in combination with other gradients, elements, or agents discussed herein. The pain reducers or analgesics may be any known in the art, such as opioids and/or non-steroidal anti-inflammatory drugs (NTHES).

The following list of embodiments of the invention are to be considered as disclosing various features of the invention, which features can be considered to be specific to the particular embodiment under which they are discussed, or which are combinable with the various other features as listed in other embodiments. Thus, simply because a feature is discussed under one particular embodiment does not necessarily limit the use of that feature to that embodiment.

Embodiment 1

In one embodiment of the present invention, there is provided an antimicrobial coating having calcium phosphate and a gradient distribution of at least one metal content, such as silver, zinc, copper, in the coating. The at least one metal content may be high in the outer surface of the coating and low in the inner surface. This metal gradient-CaP coating may be achieved by dipping the implant in sequence into different sol-gel solutions, each solution having a different gradient metal concentration. The metal gradient calcium phosphate coating may include single phase calcium phosphate, such as HA, and/or may also include multiple calcium phosphate phases, such as biphasic calcium phosphates. The advantage of using a sol-gel process is that the coating may be applied to a porous ingrowth structure without leaving any portions left uncoated. While at least one sol-gel process is preferred, other primary or subsequent processes known in the art may be used.

Embodiment 2

In another embodiment of the present invention, a metallic substrate, such as silver, zinc, copper, etc., and calcium phosphate, such as HA, TCP, Ag—CaP, etc., is combined to form a composite antimicrobial coating comprised of several layers. The composite coating may be applied to an implant through the use of a plasma-spraying process, although other processes discussed herein may be used. The metallic substrate may be in the form of a powder that may be mixed together with calcium phosphate powders and co-sprayed onto an implant surface simultaneously. Alternatively, the metallic substrate and calcium phosphate powders may be applied individually, layer by layer, to an implant surface. The order in which each layer is applied may be predetermined to provide the best solution for an individual patient's needs. The gradient in the plasma-sprayed coating may be accomplished by feeding the metallic substrate powders and calcium phosphate powders into a hopper at different rates to obtain a gradient metal content in the final coating. Alternatively, the implants may undergo several separate plasma-spraying processes, each process using a different composition of pre-mixed metal and calcium phosphate powders.

Embodiment 3

In yet another embodiment of the present invention, an antimicrobial calcium phosphate coating is provided, the coating having at least one metal, such as copper, silver, zinc, etc. The antimicrobial coating further comprises a gradient degradation profile. In other words, an outer layer of the coating may have a faster dissolution rate than an inner layer of the coating. Such a dissolution rate profile may be employed to force an outer portion of the coating to dissolve quicker, thereby creating a burst release of an antimicrobial agent. To accomplish a gradient degradation profile, an outer layer might utilize a more degradable calcium phosphate, whereas the inner surface layer might utilize a more stable calcium phosphate. Because multiple phases (or layers) of calcium phosphates may be used in the coating, some calcium phosphates used may or may not have a metal in their compositions. Likewise, some calcium phosphates used in the coating layers may or may not have osseoinductive elements. However, it is preferred that at least one calcium phosphate phase has a metal such as silver, in order to provide the antibacterial function necessary to fight infection. It is even more preferred that at least one bone-stimulating agent is included within at least one of the coating layers to promote biologic fixation. While it is preferred that an outer portion of the coating resorbs quickly, the coating may alternatively be configured to initially resorb slowly and then quickly. This may be achieved by providing an inner layer with more carbonate than an outer layer.

Embodiment 4

In still another embodiment of the present invention, there is provided a coated implant having a metal or metal-ion adsorbed outer surface. The outer surface is configured to increase metal ion release at the bone-implant interface immediately after implantation to ward off infection and kill any residing bacteria. The metal ion-enriched outer coating on the implant may be formed by first immersing the implant into calcium phosphate to form one or more layers. The one or more layers may or may not comprise a metal, such as silver, zinc, or copper, as previously discussed and also may or may not comprise a bone-stimulating agent or dissolution catalyst. The coated implant is then finally immersed into a metal-soluble solution, such as silver nitrate or silver fluoride, to adsorb metal ions onto the outer surface of the coated implant and increase the metal concentration at the outer surface of the coated implant. In one particular embodiment, a silver-soluble solution may be advantageously utilized to form an outer surface layer having an increased concentration of silver ions at the outer surface of the coating. Alternatively, an insoluble metal solution may be used to provide a metal outer surface to the coating. In this latter instance, a calcium phosphate-coated implant is first submersed into the insoluble metal solution. Once the insoluble metal solution is absorbed onto the outer surface of the coated implant, the implant may then be removed from the insoluble metal solution and exposed to light. Exposure to light reduces the absorbed metal ions at the outer surface to metal.

Embodiment 5

In yet another embodiment, the multi-layer gradient antimicrobial coating of the present invention may include one or more discontinuous layer portions. For example, an outer layer of the multi-layer gradient antimicrobial coating may comprise a discontinuous "speckled" coating formed from layer portions. These layer portions may be strategically placed within the multi-layer gradient antimicrobial coating such that the inhibitory zones for each of the layer portions overlap. In doing so, the amount of antimicrobial and/or antibacterial agents used in the multi-layer gradient antimicrobial coating may be decreased, thereby minimizing patient exposure, while still maintaining adequate protection against infection. Providing layer portions may further serve to increase the surface texture/roughness of the multi-layer gradient antimicrobial coating.

Embodiment 6

In another embodiment of the present invention, there is provided a coating having a gradient analgesic concentration. The coating preferably comprises calcium phosphate (CaP); however, other base coating materials known in the art may be equally employed. The analgesic concentration is preferably higher in an outer surface portion of the coating than in an inner portion of the coating, in order to: (1) provide the maximum amount of relief to a patient immediately after surgery; and then (2) maintain a lower, safe dosage to provide long-term relief.

Such an analgesic gradient CaP coating may be formed using several coating techniques. However, for porous-surfaced implants, a non-line-of-sight coating process is preferred. Examples of such non-line-of-sight coating processes include, but are not limited to sol-gel dip coating, electrodeposition, electrophorosis, biomimetic methods, and/or combinations thereof. For example, the gradient analgesic concentration may be formed by first applying a pure thin film calcium phosphate layer to an implant surface to form a coated implant. This layer may be applied using a sol-gel dip coating method and then hardened by sintering at an elevated temperature to achieve a sufficient bonding strength at the coating/implant interface. The coated implant may then be immersed into a first solution containing both calcium phosphate and a first concentration of at least one analgesic agent.

The first solution may be simulated body fluid (SBF) solution, modified SBF solution, or any solution which may be able to form an apatite coating onto an implant surface. In order to accelerate the coating deposition process of the first solution, an elevated temperature is preferred (e.g., sintering); however, it is important that the elevated temperature is not so high as to denature the at least one analgesic agent. If desirable, this process may be repeated for additional second, third, and fourth solutions having other concentrations of the at least one analgesic agent to form a coating having a gradient concentration of the at least one analgesic agent, the gradient extending in a direction perpendicular to the implant surface. It is to be understood that other additives may be present within the coating, the additives being in uniform or gradient concentrations throughout the coating depth. The additives may include antimicrobial agents, bone-promoting agents, antibiotics, steroids, anti-inflammatories, antispasmodics, bioactives (e.g., BMP, bisphosphonates), hemostats, or any other agent discussed herein.

The analgesics described herein may be either local anesthetics, narcotic or non-narcotic in nature. An example of a local anesthetic is local anesthetics is bupivacaine (e.g. Marcain, Marcaine, Sensorcaine and Vivacaine). Some examples of narcotic analgesics that may be advantageously utilized are opioids, morphine, codeine, oxycodone (Percodan), levorphanol (levodromoran), propoxyphene (Darvon), hydrocodone (Vicodin), pentazocine (Talwin) and/or combinations thereof. Some examples of non-narcotic analgesics that may be advantageously utilized are acetylsalicylic acid (aspirin), ibuprofen, phenylbutazone (Butazolidine), indomethacin (Indocin), acetaminophen, phenacetin, and combinations thereof. The analgesics may be topical and may include ibuprofen- or diclofenac-containing gels, capsaicin, Lidocaine, anti-inflammatories, and steroids without limitation.

It will be appreciated that other analgesics may be advantageously utilized either alone or in combination, so long as adverse reactions from combining are avoided. Examples of suitable analgesics may include, but are not limited to, natural opium alkaloids, such as morphine, opium, hydromorphone, nicomorphine, oxycodone, dihydrocodeine, diamorphine, papaveretum, morphine combinations, dihydrocodeine combinations, codeine combinations excluding psycholeptics, and codeine combinations with psycholeptics; phenylpiperidine derivatives including ketobemidone, pethidine, fentanyl, pethidine, combinations excluding psycholeptics, pethidine, and combinations with psycholeptics; diphenylpropylamine derivatives such as dextromoramide, piritramide, dextropropoxyphene, bezitramide, methadone combinations excluding psycholeptics, dextropropoxyphene combinations excluding psycholeptics; dextropropoxyphene combinations with psycholeptics; benzomorphan derivatives such as pentazocine and phenazocine and combinations thereof; oripavine derivatives such as buprenorphine; morphinan derivatives such as butorphanol and nalbufine; opioids in combination with antispasmodics such as morphine and antispasmodics, ketobemidone and antispasmodics, pethidine and antispasmodics, hydromorphone and antispasmodics, and combinations thereof; other opioids such as tilidine, tramadol, dezocine, tramadol combinations, and combinations thereof; other analgesics and antipyretics including salicylic acid and derivatives such as acetylsalicylic acid, aloxiprin, choline salicylate, sodium salicylate, salicylamide, salsalate, ethenzamide, morpholine salicylate, dipyrocetyl, benorilate, diflunisal, potassium salicylate, guacetisal, carbasalate calcium, imidazole salicylate, and combinations thereof; pyrazolones such as phenazone, metamizole, aminophenazone, propyphenazone, nifenazone, and combinations thereof; anilides such as paracetamol, phenacetin, bucetin, propacetamol, and combinations thereof; other analgesics and antipyretics such as rimazolium, glafenine, floctafenine, viminol, nefopam, flupirtine, ziconotide; and corticosteroid derivatives such as flumedroxone and combinations thereof.

Any one or more of the above mentioned analgesics could be used in the gradient coating. The analgesics may vary in concentration in a direction extending perpendicular to the implant surface. If narcotic analgesics and non-narcotic analgesics are to be used together, it is preferred that the narcotic analgesics are used at outer coating portions and the non-narcotic analgesics are used at inner coating portions. While non-narcotic analgesics are generally recognized to be effective in relieving skeletal pain due to inflammation (such as arthritis), their analgesic properties are not nearly as strong as those of narcotic analgesics, such as morphine and synthetic opioids. Because the pain experienced by a patient is most severe right after a total joint replacement or other surgery involving an implanted device, a stronger analgesic, such as morphine, may be provided at an outer surface of the coating, the stronger analgesic preferably reducing in concentration from an outer surface of the coating as it approaches the coating/implant interface. In doing so, a patient may be less-susceptible to addiction, and is essentially "weaned" from the high initial dosage that is required after surgery but is not necessary during long-term recovery.

As the healing process continues, the pain experienced by a patient becomes less acute and/or noticeable. Therefore, the gradient coating may employ weaker analgesics at the inner portions of the gradient coating. These weaker analgesics may be provided in the form of a gradient—generally increasing in concentration from an outer portion of the coating towards the coating/implant interface.

Another reason to provide narcotic analgesics mainly at outer portions of the gradient coating, is because narcotic drugs might prevent platelet agglutination, which may inhibit or delay the normal bone healing process and osseointegration. Because the inner coating portions are more proximate to the implant surface and/or the ingrowth structure, it is therefore, desirable to provide these coating portions with either non-narcotic analgesics or very low doses of narcotic analgesics to avoid interference with platelet agglutination.

It is possible to have some overlap between gradients of analgesic agents. The gradients may be staggered and may vary in dosage so as to provide smooth, controlled transitions in a pre-defined pain management plan designed for an individual patient or a population subset. The pre-defined pain management plan could be, for instance, included as part of a prescription for an implant.

If narcotic and non-narcotic analgesics are to be used together in the coating, the implant may be first coated with a pure calcium phosphate (CaP) in a manner discussed above to obtain good implant bonding strength, cohesion, and ingrowth characteristics. The coated implant may then be immersed into a first solution containing calcium phosphate, a first concentration of a non-narcotic analgesic, and a first concentration of a narcotic analgesic. The first solution may be applied in any manner described herein. The twice-coated implant may then be immersed into a second solution containing calcium phosphate, a second concentration of a non-narcotic analgesic, and a second concentration of a narcotic analgesic.

As stated above, it is preferred that the second concentration of a narcotic analgesic be higher than the first concentration of a narcotic analgesic. Conversely, it is preferred that the second concentration of a non-narcotic analgesic be lower than the first concentration of a non-narcotic analgesic. This process may be done iteratively to produce finer and finer graduations within the coating.

It is to be understood that other additives may be present within the coating, the additives being in the form of a uniform or gradient concentration throughout the coating depth. The additives may include antimicrobial agents, bone-promoting agents, antibiotics, steroids, anti-inflammatories, antispasmodics, bioactives (e.g., BMP, bisphosphonates), hemostats, or any other agent discussed herein.

Embodiment 7

In another embodiment of the present invention, a gradient coating is provided by first coating an implant or ingrowth structure with calcium phosphate using any one of the aforementioned techniques. As previously stated herein, a pure thin-film calcium phosphate layer is preferred at the coating/implant interface to improve the bonding strength of the gradient coating. The once-coated implant is then dipped into a first biodegradable polymer solution which contains a first concentration of at least one analgesic agent.

The polymer solution is prepared by first dissolving at least one biodegradable and/or biocompatible polymer, such as PCL, PLGA, PLLA, PGA, etc. or combinations thereof, into a solvent and then adding a pre-measured amount of the at least one analgesic agent. After the implant is dipped into the first biodegradable polymer solution, it is allowed to dry out in air. In order to expedite and facilitate solvent evaporation of the first biodegradable polymer solution, a vacuum treatment at room temperature may be advantageously utilized. The polymer(s) within the coating serve as a carrier for the at least one analgesic in the formed coating. If desired, additional second, third, and fourth, etc. polymer solutions may be subsequently provided, each polymer solution having a different concentration of the at least one analgesic agent and forming another layer within the gradient coating. It is to be understood that multiple analgesic agents and suitable carriers other than polymers may be present within each solution without departing from the scope of the invention.

U.S. Pat. No. 5,567,431, issued on Oct. 22, 1996, discloses an antibiotic uniformly dispersed in an amorphous poly-lactic acid matrix. The disclosure of the '431 patent is incorporated by reference herein in its entirety.

As mentioned above, multiple additives may also be present within the coating, the additives being provided in a uniform or gradient concentration throughout the coating depth. The additives may include antimicrobial agents, bone-promoting agents, antibiotics, steroids, anti-inflammatories, antispasmodics, bioactives (e.g., BMP, bisphosphonates), hemostats, or any other agent discussed herein.

Embodiment 8

In yet another embodiment of the present invention, there is provided a coating for an implant, the coating having a first layer adjacent the implant surface. The first layer includes a thin film calcium phosphate (CaP) having a first low concentration of an antimicrobial agent. While this first layer may also contain additional additives such as analgesics, bioactives, or bone-stimulating agents, it is preferred that only a small amount of an antimicrobial be present in order to provide optimal cohesion and bonding strength with the substrate material of the implant without sintering. A second layer is then provided over the first layer, the second layer preferably comprising a biomimetic calcium phosphate, a second slightly higher concentration of an antimicrobial agent than the first layer, a bioactive (e.g., BMP), and a non-narcotic agent for long-term pain relief and/or reducing inflammation. Lastly, a third outer layer is provided over the second layer, the third outer layer comprising a biomimetic calcium phosphate, an even higher concentration of an antimicrobial agent than the first and second layers (for immediate post-op infection resistance), a similar or lower concentration of a bioactive (e.g., BMP) than the second layer, and a narcotic agent (e.g., opioid) for immediate, highly-effective pain relief.

Embodiment 9

Figure 14:
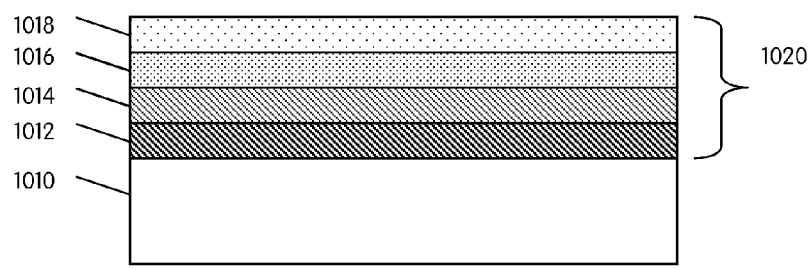
FIG. 14 is a schematic of an exemplary embodiment of the present invention utilizing at least one analgesic.

Turning to FIG. 14, there is provided still yet another embodiment of the present invention. Numeral identifier (1010) represents an implant or ingrowth structure formed from a substrate material, such as titanium, titanium alloy, cobalt-chromium, zirconium, stainless steel, or any other biocompatible metal known in the art. A gradient coating (1020) is applied to the implant (1010), the gradient coating (1020) has a first thin film inner layer (1012) of pure hydroxyapatite. Because this layer (1012) is generally free from additives that may reduce the bonding strength characteristics with respect to the material of the implant (1010), it may be thought of as a "primer" for the gradient coating (1020). The first layer (1012) may be sintered to the implant (1010) by conventional ceramic firing methods. A second layer (1014) is also provided, the layer preferably containing a substantial concentration of a bone-stimulating agent, such as fluoride, a non-narcotic analgesic, such as aspirin, and a low dose of a bioactive (e.g., BMP or bisphosphonate). The second layer may be fired or not fired to the first layer, but is preferably not fired in order to maintain the virgin properties of the additives.

A third layer (1016) may further be provided, the third layer (1016) has, for example, a moderate concentration of an antimicrobial, such as silver, zinc, or copper, a lower dose of a non-narcotic analgesic than the second layer (1014), a higher concentration of a bone stimulating agent than the second layer (1014), and a low dose of a narcotic analgesic. Like the second layer (1014), the third layer (1016) may be applied by methods other than ceramic firing. A fourth layer (1018) may be for example, a polymer-based carrier coating and may comprise a higher level of an antimicrobial than the third layer (1016), a higher dose or concentration of a narcotic analgesic than the third layer (1016), and a lower dose of a bone-stimulating agent than both the second (1014) and third (1016) layers.

Functionally-Graded Antimicrobial Coatings

Embodiment 10

According to a tenth embodiment of the present invention, there is provided, a medical implant having one or more surfaces comprising a functionally-graded coating disposed thereon, wherein said functionally-graded coating comprises multiple coating layers and an antimicrobial agent, and wherein a concentration of said antimicrobial agent in is different in at least two of said multiple coating layers.

Embodiment 11

According to an eleventh embodiment of the present invention, there is provided, a medical implant having one or more surfaces comprising a functionally-graded coating disposed thereon, wherein said functionally-graded coating comprises multiple coating layers and an antimicrobial agent, and wherein an outer of said multiple coating layers has a higher concentration of said antimicrobial agent than an inner of said multiple coating layers.

Embodiment 12

According to a twelfth embodiment of the present invention, there is provided, a medical implant having one or more surfaces comprising a functionally-graded coating disposed thereon, wherein said functionally-graded coating comprises multiple coating layers and an antimicrobial agent disposed within an outer of said multiple coating layers, wherein an inner of said multiple coating layers does not contain an antimicrobial agent.

Embodiment 13

According to a thirteenth embodiment of the present invention, there is provided, a medical implant having one or more surfaces comprising a functionally-graded coating disposed thereon, wherein said functionally-graded coating comprises multiple coating layers and an antimicrobial agent, wherein a concentration of said antimicrobial agent is different in at least two of said multiple coating layers, and wherein the antimicrobial agent may be selected from any one of silver, copper, zinc, manganese, gold, iron, nickel, cobalt, cadmium, platinum, and combinations thereof.

Embodiment 14

According to a fourteenth embodiment of the present invention, there is provided, a medical implant having one or more surfaces comprising a functionally-graded coating disposed thereon, wherein said functionally-graded coating comprises multiple coating layers and an antimicrobial agent, wherein a concentration of said antimicrobial agent is different in at least two of said multiple coating layers, wherein the antimicrobial agent may be selected from silver, copper, zinc, manganese, gold, iron, nickel, cobalt, cadmium, platinum, and combinations thereof, and wherein the maximum silver concentration within the functionally-graded coating is generally between about 0.1 to about 10 weight percent, and more preferably between about 0.5 to about 3 weight percent.

Embodiment 15

According to a fifteenth embodiment of the present invention, there is provided, a medical implant having one or more surfaces comprising a functionally-graded coating disposed thereon, wherein said functionally-graded coating comprises multiple coating layers and an antimicrobial agent, wherein a concentration of said antimicrobial agent is different in at least two of said multiple coating layers, and wherein the antimicrobial agent is an antibiotic such as vancomycin, gentamycin, penicillins, cephalosporins, aminoglycoside, macrolides, clindamycin, tetracyclines, chloramphenicol, spectinomycin, polypeptide antibiotics, fluoroquinolones, and combinations thereof.

Embodiment 16

According to a sixteenth embodiment of the present invention, there is provided, a medical implant having one or more surfaces comprising a functionally-graded coating disposed thereon, wherein said functionally-graded coating comprises multiple coating layers and an antimicrobial agent, wherein a concentration of said antimicrobial agent is different in at least two of said multiple coating layers, and wherein the antimicrobial agent is an anti-fungal such as amphotericin B, nystatin, liposomal amphotericin B, flucytosine, and combinations thereof.

Embodiment 17

According to a seventeenth embodiment of the present invention, there is provided, a medical implant having one or more surfaces comprising a functionally-graded coating disposed thereon, wherein said functionally-graded coating comprises multiple coating layers and an antimicrobial agent, wherein at a concentration of said antimicrobial agent is different in at least two of said multiple coating layers, and wherein the antimicrobial agent is an anti-viral such as acyclovir, ganciclovir, idoxuridine, amantadin, interferons, azidothymidine, and combinations thereof.

Embodiment 18

According to an eighteenth embodiment of the present invention, there is provided, a medical implant having one or more surfaces comprising a functionally-graded coating disposed thereon, wherein said functionally-graded coating comprises multiple coating layers and an antimicrobial agent, wherein a concentration of said antimicrobial agent is different in at least two of said multiple coating layers, wherein at least one of said multiple coating layers contains a bone stimulating material, wherein said bone stimulating material may be selected from any of calcium, phosphate, carbonate, fluoride, silicon, magnesium, strontium, vanadium, lithium, a growth factor (BMP, etc), a biomimetic peptide, hydroxyapatite, β tricalcium phosphate, mixtures of hydroxyapatite and β tricalcium phosphate, and combinations thereof, and wherein a concentration of said bone stimulating material may be different in at least two of said multiple coating layers.

Embodiment 19

According to a nineteenth embodiment of the present invention, there is provided, a medical implant having one or more surfaces comprising a functionally-graded coating disposed thereon, wherein said functionally-graded coating comprises multiple coating layers and an antimicrobial agent, wherein a concentration of said antimicrobial agent is different in at least two of said multiple coating layers, wherein at least one of said multiple coating layers contains an analgesic agent such as a local anesthetics, such as bupivacaine (e.g. Marcain, Marcaine, Sensorcaine and Vivacaine), narcotic, an opioid, morphine, codeine, oxycodone (Percodan), levorphanol (levodromoran), propoxyphene (Darvon), pentazocine (Talwin), a non-narcotic agent, acetylsalicylic acid (aspirin), phenylbutazone (Butazolidine), indomethacin (Indocin), acetaminophen, phenacetin, and combinations thereof.

Embodiment 20

According to a twentieth embodiment of the present invention, there is provided, a medical implant having one or more surfaces comprising a functionally-graded coating disposed thereon, wherein said functionally-graded coating comprises multiple coating layers and an antimicrobial agent, wherein the concentration of said antimicrobial agent is different in at least two of said multiple coating layers, wherein at least one of said multiple coating layers contains an analgesic agent, and wherein a concentration of said analgesic agent is different in at least two of said multiple coating layers.

Embodiment 21

According to a twenty-first embodiment of the present invention, there is provided, a medical implant having one or more surfaces comprising a functionally-graded coating disposed thereon, wherein said functionally-graded coating comprises multiple coating layers and an antimicrobial agent, wherein the concentration of said antimicrobial agent is different in at least two of said multiple coating layers, and wherein an outer of said multiple coating layers comprises a narcotic analgesic agent and an inner of said multiple coating layers comprises a non-narcotic analgesic agent.

Embodiment 22

According to a twenty-second embodiment of the present invention, there is provided, a medical implant having one or more surfaces comprising a functionally-graded coating disposed thereon, wherein said functionally-graded coating comprises multiple coating layers and an antimicrobial agent, wherein at the concentration of said antimicrobial agent is different in at least two of said multiple layers, and wherein said antimicrobial agent comprises a silver specie including, but not limited to: a silver salt, silver nitrate, silver perchlorate, silver acetate, silver tetrafluoroborate, silver trifoliate, silver fluoride, silver oxide, silver hydroxide, other silver-"oxo" species, silver sulfadiazine, mixtures of silver with other stabilizing ligands other than sulfadiazine, and combinations thereof.

Embodiment 23

According to a twenty-third embodiment of the present invention, there is provided, a functionally-graded antimicrobial coating applied to one or more surfaces of a medical implant, wherein said functionally-graded coating comprises multiple layers of a bone conducting material and an antimicrobial agent disposed within at least one of said multiple layers, wherein a concentration of said antimicrobial agent is different in at least two of said multiple layers, and wherein the bone conducting material may be selected from calcium phosphate, hydroxyapatite, β tricalcium phosphate, a mixture of hydroxyapatite and β tricalcium phosphate, resorbable polymers, bioglass, derivatised phosphate-based compound, orthophosphates, monocalcium phosphates, octacalcium phosphates, dicalcium phosphate hydrate (brushite), dicalcium phosphate anhydrous (monetite), anhydrous tricalcium phosphates, whitlocktite, tetracalcium phosphate, amorphous calcium phosphates, fluoroapatiete, chloroapatite, non-stoichiometric apatites, carbonate apatites, biologically-derived apatite, calcium hydrogen phosphate, calcium hydrogen apatite, water insoluble ceramics, phosphates, polyphosphates, carbonates, silicates, aluminates, borates, zeolites, bentonite, kaolin, and combinations thereof.

Embodiment 24

According to a twenty-fourth embodiment of the present invention, there is provided, a functionally-graded antimicrobial coating applied to one or more surfaces of a medical implant, wherein said functionally-graded coating comprises multiple layers of a bone conducting material and an antimicrobial agent disposed within at least one of said multiple layers, wherein a concentration of the antimicrobial agent is greater in an outer of said multiple layers than a concentration of the antimicrobial agent in an inner of said multiple layers.

Embodiment 25

According to a twenty-fifth embodiment of the present invention, there is provided, a functionally-graded antimicrobial coating applied to one or more surfaces of a medical implant, wherein said functionally-graded coating comprises multiple layers of a bone conducting material and an antimicrobial agent disposed within an outer of said multiple layers, wherein the bone conducting material may be selected from calcium phosphate, hydroxyapatite, β tricalcium phosphate, a mixture of hydroxyapatite and β tricalcium phosphate, resorbable polymers, bioglass, derivatised phosphate-based compound, orthophosphates, monocalcium phosphates, octacalcium phosphates, dicalcium phosphate hydrate (brushite), dicalcium phosphate anhydrous (monetite), anhydrous tricalcium phosphates, whitlocktite, tetracalcium phosphate, amorphous calcium phosphates, fluoroapatiete, chloroapatite, non-stoichiometric apatites, carbonate apatites, biologically-derived apatite, calcium hydrogen phosphate, calcium hydrogen apatite, water insoluble ceramics, phosphates, polyphosphates, carbonates, silicates, aluminates, borates, zeolites, bentonite, kaolin, and combinations thereof; and wherein an inner of said multiple layers does not contain an antimicrobial agent.

Embodiment 26

According to a twenty-sixth embodiment of the present invention, there is provided, a functionally-graded antimicrobial coating applied to one or more surfaces of a medical implant, wherein said functionally-graded coating comprises multiple layers of a bone conducting material and an antimicrobial agent disposed within at least one of said multiple layers, wherein a concentration of said antimicrobial agent is different in at least two of said multiple layers, wherein the bone conducting material may be selected from calcium phosphate, hydroxyapatite, β tricalcium phosphate, a mixture of hydroxyapatite and β tricalcium phosphate, resorbable polymers, bioglass, derivatised phosphate-based compound, orthophosphates, monocalcium phosphates, octacalcium phosphates, dicalcium phosphate hydrate (brushite), dicalcium phosphate anhydrous (monetite), anhydrous tricalcium phosphates, whitlocktite, tetracalcium phosphate, amorphous calcium phosphates, fluoroapatiete, chloroapatite, non-stoichiometric apatites, carbonate apatites, biologically-derived apatite, calcium hydrogen phosphate, calcium hydrogen apatite, water insoluble ceramics, phosphates, polyphosphates, carbonates, silicates, aluminates, borates, zeolites, bentonite, kaolin, and combinations thereof; wherein a concentration of the antimicrobial agent is greater in an outer of said multiple layers than a concentration of the antimicrobial agent in an inner of said multiple coating layers, and wherein the antimicrobial agent is preferably selected from silver, copper, zinc, manganese, gold, iron, nickel, cobalt, cadmium, platinum, and combination thereof.

Embodiment 27

According to a twenty-seventh embodiment of the present invention, there is provided, a functionally-graded antimicrobial coating applied to one or more surfaces of a medical implant, wherein said functionally-graded coating comprises multiple layers of a bone conducting material and an antimicrobial agent disposed within at least one of said multiple layers, wherein a concentration of said antimicrobial agent is different in at least two of said multiple layers, wherein the bone conducting material may be selected from calcium phosphate, hydroxyapatite, β tricalcium phosphate, a mixture of hydroxyapatite and β tricalcium phosphate, resorbable polymers, bioglass, derivatised phosphate-based compound, orthophosphates, monocalcium phosphates, octacalcium phosphates, dicalcium phosphate hydrate (brushite), dicalcium phosphate anhydrous (monetite), anhydrous tricalcium phosphates, whitlocktite, tetracalcium phosphate, amorphous calcium phosphates, fluoroapatiete, chloroapatite, non-stoichiometric apatites, carbonate apatites, biologically-derived apatite, calcium hydrogen phosphate, calcium hydrogen apatite, water insoluble ceramics, phosphates, polyphosphates, carbonates, silicates, aluminates, borates, zeolites, bentonite, kaolin, and combinations thereof; wherein a concentration of the antimicrobial agent is greater in an outer of said multiple coating layers than in an inner of said multiple layers, wherein the antimicrobial agent may be selected from silver, copper, zinc, manganese, gold, iron, nickel, cobalt, cadmium, platinum, and combinations thereof, and wherein a maximum silver concentration within the functionally graded coating ranges from about 0.1 to about 10 weight percent, and more preferably ranges between about 0.5 to about 3 weight percent.

Embodiment 28

According to a twenty-eighth embodiment of the present invention, there is provided, a functionally-graded antimicrobial coating applied to one or more surfaces of a medical implant, wherein said functionally-graded coating comprises multiple layers of a bone conducting material and an antimicrobial agent disposed within at least one of said multiple layers, wherein a concentration of said antimicrobial agent is different in at least two of said multiple layers, and wherein the antimicrobial agent is an antibiotic such as vancomycin, gentamycin, penicillins, cephalosporins, aminoglycoside, macrolides, clindamycin, tetracyclines, chloramphenicol, spectinomycin, polypeptide antibiotics, fluoroquinolones, and combinations thereof.

Embodiment 29

According to a twenty-ninth embodiment of the present invention, there is provided, a functionally-graded antimicrobial coating applied to one or more surfaces of a medical implant, wherein said functionally-graded coating comprises multiple layers of a bone conducting material and an antimicrobial agent disposed within at least one of said multiple layers, wherein a concentration of said antimicrobial agent is different in at least two of said multiple layers, and wherein the antimicrobial agent is an anti-fungal selected from amphotericin B, nystatin, liposomal amphotericin B, flucytosine, and combinations thereof.

Embodiment 30

According to a thirtieth embodiment of the present invention, there is provided, a functionally-graded antimicrobial coating applied to one or more surfaces of a medical implant, wherein said functionally-graded coating comprises multiple layers of a bone conducting material and an antimicrobial agent disposed within at least one of said multiple layers, wherein a concentration of said antimicrobial agent is different in at least two of said multiple layers, and wherein the antimicrobial agent is an anti-viral such as acyclovir, ganciclovir, idoxuridine, amantadin, interferons, azidothymidine, and combinations thereof.

Embodiment 31

According to a thirty-first embodiment of the present invention, there is provided, a functionally-graded antimicrobial coating applied to one or more surfaces of a medical implant, wherein said functionally-graded coating comprises multiple layers of a bone conducting material and an antimicrobial agent disposed within at least one of said multiple layers, wherein a concentration of said antimicrobial agent is different in at least two of said multiple layers, and wherein at least one of said multiple layers contains a bone stimulating agent such as carbonate, fluoride, silicon, magnesium, strontium, vanadium, lithium, a growth factor (e.g., BMP), a biomimetic peptide, and combinations thereof.

Embodiment 32

According to a thirty-second embodiment of the present invention, there is provided, a functionally-graded antimicrobial coating applied to one or more surfaces of a medical implant, wherein said functionally-graded coating comprises multiple layers of a bone conducting material, an antimicrobial agent disposed within at least one of said multiple layers, and a bone stimulating agent disposed within at least one of said multiple layers; wherein a concentration of said antimicrobial agent is different in at least two of said multiple layers, and wherein a concentration of the bone stimulating agent is different in at least two of said multiple layers.

Embodiment 33

According to a thirty-third embodiment of the present invention, there is provided, a functionally-graded antimicrobial coating applied to one or more surfaces of a medical implant, wherein said functionally-graded coating comprises multiple layers of a bone conducting material and an antimicrobial agent disposed within at least one of said multiple layers, wherein a concentration of said antimicrobial agent is different in at least two of said multiple coating layers, wherein at least one of the multiple layers contains an analgesic agent such as a narcotic an opioid, morphine, codeine, oxycodone (Percodan), levorphanol (levodromoran), propoxyphene (Darvon), pentazocine (Talwin), a normarcotic analgesic, acetylsalicylic acid (aspirin), phenylbutazone (Butazolidine), indomethacin (Indocin), acetaminophen, phenacetin, etc, and combinations thereof.

Embodiment 34

According to a thirty-fourth embodiment of the present invention, there is provided, a functionally-graded antimicrobial coating applied to one or more surfaces of a medical implant, wherein said functionally-graded coating comprises multiple layers of a bone conducting material and an antimicrobial agent disposed within at least one of said multiple layers, wherein a concentration of said antimicrobial agent is different in at least two of said multiple coating layers, wherein at least one of the multiple layers contains an analgesic agent, and wherein a concentration of the analgesic agent is different in at least two of said multiple layers.

Embodiment 35

According to a thirty-fifth embodiment of the present invention, there is provided, a functionally-graded antimicrobial coating applied to one or more surfaces of a medical implant, wherein said functionally-graded coating comprises multiple layers of a bone conducting material and an antimicrobial agent disposed within at least one of said multiple layers, wherein a concentration of said antimicrobial agent is different in at least two of said multiple coating layers, wherein an outer of said multiple layers comprises a narcotic analgesic agent, and wherein an inner of said multiple layers comprises a non-narcotic analgesic agent.

Embodiment 36

According to a thirty-sixth embodiment of the present invention, there is provided, a functionally-graded antimicrobial coating applied to one or more surfaces of a medical implant, wherein said functionally-graded coating comprises multiple layers of a bone conducting material and an antimicrobial agent disposed within at least one of said multiple layers, wherein a concentration of said antimicrobial agent is different in at least two of said multiple coating layers, and wherein said antimicrobial agent comprises a silver specie including, but not limited to a silver salt, silver nitrate, silver perchlorate, silver acetate, silver tetrafluoroborate, silver trifoliate, silver fluoride, silver oxide, silver hydroxide, other silver-"oxo" species, silver sulfadiazine, mixtures of silver with other stabilizing ligands, and combinations thereof.

Functionally-Graded Bone-Stimulating Coatings

Embodiment 37

According to a thirty-seventh embodiment of the present invention, there is provided, a medical implant having one or more surfaces comprising a functionally-graded coating disposed thereon, wherein said functionally-graded coating comprises multiple coating layers and a bone stimulating agent, and wherein a concentration of said bone stimulating agent is different in at least two of said multiple coating layers.

Embodiment 38

According to an thirty-eighth embodiment of the present invention, there is provided, a medical implant having one or more surfaces comprising a functionally-graded coating disposed thereon, wherein said functionally-graded coating comprises multiple coating layers and a bone stimulating agent, and wherein an outer of said multiple coating layers has a higher concentration of said bone stimulating agent than an inner of said multiple coating layers.

Embodiment 39

According to a thirty-ninth embodiment of the present invention, there is provided, a medical implant having one or more surfaces comprising a functionally-graded coating disposed thereon, wherein said functionally-graded coating comprises multiple coating layers and a bone stimulating agent disposed within an outer of said multiple coating layers, wherein an inner of said multiple coating layers does not contain a bone stimulating agent.

Embodiment 40

According to a fortieth embodiment of the present invention, there is provided, a medical implant having one or more surfaces comprising a functionally-graded coating disposed thereon, wherein said functionally-graded coating comprises multiple coating layers and an bone stimulating agent, wherein a concentration of said bone stimulating agent is different in at least two of said multiple coating layers, and wherein the bone stimulating agent may be selected from a carbonate, fluoride, silicon, magnesium, strontium, vanadium, lithium, a growth factor (e.g., BMP), a biomimetic peptide, a bioactive, and combinations thereof.

Embodiment 41

According to a forty-first embodiment of the present invention, there is provided, a medical implant having one or more surfaces comprising a functionally-graded coating disposed thereon, wherein said functionally-graded coating comprises multiple coating layers and a bone stimulating agent, wherein a concentration of said bone stimulating agent is different in at least two of said multiple coating layers, wherein the bone stimulating agent may be selected from carbonate, fluoride, silicon, magnesium, strontium, vanadium, lithium, a growth factor (e.g., BMP), a biomimetic peptide, a bioactive, and combinations thereof; wherein the functionally-graded coating further comprises an antimicrobial agent such as silver, copper, zinc, manganese, gold, iron, nickel, cobalt, cadmium, and platinum, and combinations thereof; and, wherein a maximum concentration of the antimicrobial agent within the functionally-graded coating may generally be between about 0.1 to about 10 weight percent, and more preferably between about 0.5 to about 3 weight percent.

Embodiment 42

According to a forty-second embodiment of the present invention, there is provided, a medical implant having one or more surfaces comprising a functionally-graded coating disposed thereon, wherein said functionally-graded coating comprises multiple coating layers and a bone stimulating agent, wherein a concentration of said bone stimulating agent is different in at least two of said multiple coating layers, and wherein the functionally-graded coating further comprises an antibiotic such as vancomycin, gentamycin, penicillins, cephalosporins, aminoglycoside, macrolides, clindamycin, tetracyclines, chloramphenicol, spectinomycin, polypeptide antibiotics, fluoroquinolones, and combinations thereof.

Embodiment 43

According to a forty-third embodiment of the present invention, there is provided, a medical implant having one or more surfaces comprising a functionally-graded coating disposed thereon, wherein said functionally-graded coating comprises multiple coating layers and a bone stimulating agent, wherein a concentration of said bone stimulating agent is different in at least two of said multiple coating layers, and wherein the functionally-graded coating further comprises an anti-fungal such as amphotericin B, nystatin, liposomal amphotericin B, flucytosine, and combinations thereof.

Embodiment 44

According to a forty-forth embodiment of the present invention, there is provided, a medical implant having one or more surfaces comprising a functionally-graded coating disposed thereon, wherein said functionally-graded coating comprises multiple coating layers and a bone stimulating agent, wherein a concentration of said bone stimulating agent is different in at least two of said multiple coating layers, and wherein the functionally-graded coating further comprises an anti-viral such as acyclovir, ganciclovir, idoxuridine, amantadin, interferons, azidothymidine, and combinations thereof.

Embodiment 45

According to a forty-fifth embodiment of the present invention, there is provided, a medical implant having one or more surfaces comprising a functionally-graded coating disposed thereon, wherein said functionally-graded coating comprises multiple coating layers and a bone stimulating agent, wherein a concentration of said bone stimulating agent is different in at least two of said multiple coating layers, wherein the functionally-graded coating further comprises an antimicrobial agent such as silver, copper, zinc, manganese, gold, iron, nickel, cobalt, cadmium, and platinum, or combinations thereof; and, wherein a concentration of said antimicrobial agent is different in at least two of said multiple coating layers.

Embodiment 46

According to a forty-sixth embodiment of the present invention, there is provided, a medical implant having one or more surfaces comprising a functionally-graded coating disposed thereon, wherein said functionally-graded coating comprises multiple coating layers and a bone stimulating agent, wherein a concentration of said bone stimulating agent is different in at least two of said multiple coating layers, and wherein at least one of said multiple coating layers contains an analgesic agent which may be a local anesthetic, such as bupivacaine (e.g. Marcain, Marcaine, Sensorcaine and Vivacaine), a narcotic, such as an opioid, morphine, codeine, oxycodone (Percodan), levorphanol (levodromoran), propoxyphene (Darvon), pentazocine (Talwin); or non-narcotic, such as acetylsalicylic acid (aspirin), phenylbutazone (Butazolidine), indomethacin (Indocin), acetaminophen, phenacetin, and combinations thereof.

Embodiment 47

According to a forty-seventh embodiment of the present invention, there is provided, a medical implant having one or more surfaces comprising a functionally-graded coating disposed thereon, wherein said functionally-graded coating comprises multiple coating layers and a bone stimulating agent, wherein the concentration of said bone stimulating agent in is different in at least two of said multiple coating layers, wherein at least one of said multiple coating layers contains an analgesic agent, and wherein a concentration of said analgesic agent is different in at least two of said multiple coating layers.

Embodiment 48

According to a forty-eighth embodiment of the present invention, there is provided, a medical implant having one or more surfaces comprising a functionally-graded coating disposed thereon, wherein said functionally-graded coating comprises multiple coating layers and a bone stimulating agent, wherein the concentration of said bone stimulating agent is different in at least two of said multiple coating layers; and, wherein an outer of said multiple coating layers comprises a narcotic analgesic agent and an inner of said multiple coating layers comprises a non-narcotic analgesic agent.

Embodiment 49

According to a forty-ninth embodiment of the present invention, there is provided, a medical implant having one or more surfaces comprising a functionally-graded coating disposed thereon, wherein said functionally-graded coating comprises multiple coating layers and a bone stimulating agent, wherein the concentration of said bone stimulating agent is different in at least two of said multiple coating layers; and, wherein said functionally-graded coating further comprises a silver specie including, but not limited to: silver salts, silver nitrate, silver perchlorate, silver acetate, silver tetrafluoroborate, silver trifoliate, silver fluoride, silver oxide, silver hydroxide, other silver-"oxo" species, silver sulfadiazine, mixtures of silver with other stabilizing ligands other than sulfadiazine, and combinations thereof.

Embodiment 50

According to a fiftieth embodiment of the present invention, there is provided, a functionally-graded coating applied to one or more surfaces of a medical implant, wherein said functionally-graded coating comprises multiple layers of a bone conducting material and a bone stimulating agent disposed within at least one of said multiple layers, wherein a concentration of said bone stimulating agent is different in at least two of said multiple layers, and wherein the bone conducting material may optionally be selected from any one or more of calcium phosphate, hydroxyapatite, β tricalcium phosphate, a mixture of hydroxyapatite and β tricalcium phosphate, resorbable polymers, bioglass, derivatised phosphate-based compound, orthophosphates, monocalcium phosphates, octacalcium phosphates, dicalcium phosphate hydrate (brushite), dicalcium phosphate anhydrous (monetite), anhydrous tricalcium phosphates, whitlocktite, tetracalcium phosphate, amorphous calcium phosphates, fluoroapatiete, chloroapatite, non-stoichiometric apatites, carbonate apatites, biologically-derived apatite, calcium hydrogen phosphate, calcium hydrogen apatite, water insoluble ceramics, phosphates, polyphosphates, carbonates, silicates, aluminates, borates, zeolites, bentonite, kaolin, and combinations thereof.

Embodiment 51

According to a fifty-first embodiment of the present invention, there is provided, a functionally-graded coating applied to one or more surfaces of a medical implant, wherein said functionally-graded coating comprises multiple layers of a bone conducting material and a bone stimulating agent disposed within at least one of said multiple layers, wherein a concentration of the bone stimulating agent is greater in an outer of said multiple layers than a concentration of the bone stimulating agent in an inner of said multiple coating layers.

Embodiment 52

According to a fifty-second embodiment of the present invention, there is provided, a functionally-graded coating applied to one or more surfaces of a medical implant, wherein said functionally-graded coating comprises multiple layers of a bone conducting material and a bone stimulating agent disposed within an outer of said multiple layers, wherein the bone conducting material may be selected from the group of calcium phosphate, hydroxyapatite, β tricalcium phosphate, a mixture of hydroxyapatite and β tricalcium phosphate, resorbable polymers, bioglass, derivatised phosphate-based compound, orthophosphates, monocalcium phosphates, octacalcium phosphates, dicalcium phosphate hydrate (brushite), dicalcium phosphate anhydrous (monetite), anhydrous tricalcium phosphates, whitlocktite, tetracalcium phosphate, amorphous calcium phosphates, fluoroapatiete, chloroapatite, non-stoichiometric apatites, carbonate apatites, biologically-derived apatite, calcium hydrogen phosphate, calcium hydrogen apatite, water insoluble ceramics, phosphates, polyphosphates, carbonates, silicates, aluminates, borates, zeolites, bentonite, kaolin, and combinations thereof; and, wherein an inner of said multiple layers does not contain a bone stimulating agent.

Embodiment 53

According to a fifty-third embodiment of the present invention, there is provided, a functionally-graded coating applied to one or more surfaces of a medical implant, wherein said functionally-graded coating comprises multiple layers of a bone conducting material and a bone stimulating agent disposed within at least one of said multiple layers, wherein a concentration of said bone stimulating agent is different in at least two of said multiple layers, wherein the bone conducting material may be selected from the group of calcium phosphate, hydroxyapatite, β tricalcium phosphate, a mixture of hydroxyapatite and β tricalcium phosphate, resorbable polymers, bioglass, derivatised phosphate-based compounds, orthophosphates, monocalcium phosphates, octacalcium phosphates, dicalcium phosphate hydrate (brushite), dicalcium phosphate anhydrous (monetite), anhydrous tricalcium phosphates, whitlocktite, tetracalcium phosphate, amorphous calcium phosphates, fluoroapatiete, chloroapatite, non-stoichiometric apatites, carbonate apatites, biologically-derived apatite, calcium hydrogen phosphate, calcium hydrogen apatite, water insoluble ceramics, phosphates, polyphosphates, carbonates, silicates, aluminates, borates, zeolites, bentonite, kaolin, and combinations thereof; wherein the functionally-graded coating further comprises a concentration of an antimicrobial agent such as a silver salt, silver nitrate, silver perchlorate, silver acetate, silver tetrafluoroborate, silver trifoliate, silver fluoride, silver oxide, silver hydroxide, other silver-"oxo" species, silver sulfadiazine, mixtures of silver with other stabilizing ligands, silver, copper, zinc, manganese, gold, iron, nickel, cobalt, cadmium, platinum, and combinations thereof; and, wherein a concentration of said antimicrobial agent is greater in an outer of said multiple layers than a concentration of the antimicrobial agent in an inner of said multiple layers.

Embodiment 54

According to an fifty-fourth embodiment of the present invention, there is provided, a functionally-graded coating applied to one or more surfaces of a medical implant, wherein said functionally-graded coating comprises multiple layers of a bone conducting material and a bone stimulating agent disposed within at least one of said multiple layers, wherein a concentration of said bone stimulating agent is different in at least two of said multiple layers, wherein the bone conducting material may be selected from the group of calcium phosphate, hydroxyapatite, β tricalcium phosphate, a mixture of hydroxyapatite and β tricalcium phosphate, resorbable polymers, bioglass, derivatised phosphate-based compound, orthophosphates, monocalcium phosphates, octacalcium phosphates, dicalcium phosphate hydrate (brushite), dicalcium phosphate anhydrous (monetite), anhydrous tricalcium phosphates, whitlocktite, tetracalcium phosphate, amorphous calcium phosphates, fluoroapatiete, chloroapatite, non-stoichiometric apatites, carbonate apatites, biologically-derived apatite, calcium hydrogen phosphate, calcium hydrogen apatite, water insoluble ceramics, phosphates, polyphosphates, carbonates, silicates, aluminated, borates, zeolites, bentonite, kaolin, and combinations thereof; wherein a concentration of the bone stimulating agent is greater in an outer of said multiple layers than in an inner of said multiple layers, wherein the functionally-graded coating further comprises an antimicrobial agent such as a silver salt, silver nitrate, silver perchlorate, silver acetate, silver tetrafluoroborate, silver trifoliate, silver fluoride, silver oxide, silver hydroxide, other silver-"oxo" species, silver sulfadiazine, mixtures of silver with other stabilizing ligands, silver, copper, zinc, manganese, gold, iron, nickel, cobalt, cadmium, platinum, and combinations thereof; and, wherein a maximum concentration of the antimicrobial agent within any of said multiple layers of the functionally-graded coating generally ranges between about 0.1 to about 10 weight percent, and more preferably between about 0.5 to about 3 weight percent.

Embodiment 55

According to a fifty-fifth embodiment of the present invention, there is provided, a functionally-graded coating applied to one or more surfaces of a medical implant, wherein said functionally-graded coating comprises multiple layers of a bone conducting material and a bone stimulating agent disposed within at least one of said multiple layers, wherein a concentration of said bone stimulating agent is different in at least two of said multiple layers, and wherein the functionally-graded coating further comprises an antibiotic such as vancomycin, gentamycin, penicillins, cephalosporins, aminoglycoside, macrolides, clindamycin, tetracyclines, chloramphenicol, spectinomycin, polypeptide antibiotics, fluoroquinolones, and combinations thereof.

Embodiment 56

According to a fifty-sixth embodiment of the present invention, there is provided, a functionally-graded coating applied to one or more surfaces of a medical implant, wherein said functionally-graded coating comprises multiple layers of a bone conducting material and a bone stimulating agent disposed within at least one of said multiple layers, wherein a concentration of said bone stimulating agent is different in at least two of said multiple layers, and wherein the functionally-graded coating further comprises an anti-fungal such as amphotericin B, nystatin, liposomal amphotericin B, flucytosine, and combinations thereof.

Embodiment 57

According to a fifty-seventh embodiment of the present invention, there is provided, a functionally-graded coating applied to one or more surfaces of a medical implant, wherein said functionally-graded coating comprises multiple layers of a bone conducting material and a bone stimulating agent disposed within at least one of said multiple layers, wherein a concentration of said bone stimulating agent is different in at least two of said multiple coating layers, and wherein the functionally-graded coating further comprises an anti-viral such as acyclovir, ganciclovir, idoxuridine, amantadin, interferons, azidothymidine, and combinations thereof.

Embodiment 58

According to a fifty-eighth embodiment of the present invention, there is provided, a functionally-graded coating applied to one or more surfaces of a medical implant, wherein said functionally-graded coating comprises multiple layers of a bone conducting material and a bone stimulating agent disposed within at least one of said multiple layers, wherein a concentration of said bone stimulating agent is different in at least two of said multiple layers; and, wherein the bone stimulating agent is selected from carbonate, fluoride, silicon, magnesium, strontium, vanadium, lithium, a growth factor (e.g., BMP), a biomimetic peptide, a bioactive, and combinations thereof.

Embodiment 59

According to a fifty-ninth embodiment of the present invention, there is provided, a functionally-graded coating applied to one or more surfaces of a medical implant, wherein said functionally-graded coating comprises multiple layers of a bone conducting material and a bone stimulating agent disposed within at least one of said multiple layers, wherein a concentration of said bone stimulating agent is different in at least two of said multiple layers, wherein at least one of said multiple layers contains an antimicrobial agent, and wherein a concentration of the antimicrobial agent is different for at least two of said multiple layers.

Embodiment 60

According to a sixtieth embodiment of the present invention, there is provided, a functionally-graded coating applied to one or more surfaces of a medical implant, wherein said functionally-graded coating comprises multiple layers of a bone conducting material and a bone stimulating agent disposed within at least one of said multiple layers, wherein a concentration of said bone stimulating agent is different in at least two of said multiple layers; and, wherein at least one of the multiple layers contains an analgesic agent which may be selected from local anesthetics, such as bupivacaine (e.g. Marcain, Marcaine, Sensorcaine and Vivacaine), narcotic analgesics, opioids, morphine, codeine, oxycodone (Percodan), levorphanol (levodromoran), propoxyphene (Darvon), and pentazocine (Talwin), non-narcotic analgesics, acetylsalicylic acid (aspirin), phenylbutazone (Butazolidine), indomethacin (Indocin), acetaminophen, phenacetin, etc, and combinations thereof.

Embodiment 61

According to a sixty-first embodiment of the present invention, there is provided, a functionally-graded coating applied to one or more surfaces of a medical implant, wherein said functionally-graded coating comprises multiple layers of a bone conducting material and a bone stimulating agent disposed within at least one of said multiple layers, wherein a concentration of said bone stimulating agent is different in at least two of said multiple layers; wherein at least one of the multiple layers contains an analgesic agent; and, wherein a concentration of the analgesic agent is different in at least two of said multiple layers.

Embodiment 62

According to a sixty-second embodiment of the present invention, there is provided, a functionally-graded coating applied to one or more surfaces of a medical implant, wherein said functionally-graded coating comprises multiple layers of a bone conducting material and a bone stimulating agent disposed within at least one of said multiple layers, wherein a concentration of said bone stimulating agent is different in at least two of said multiple layers; and, wherein an outer of said at multiple layers comprises a narcotic analgesic agent, and an inner of said at multiple layers comprises a non-narcotic analgesic agent.

Embodiment 63

According to a sixty-third embodiment of the present invention, there is provided, a functionally-graded coating applied to one or more surfaces of a medical implant, wherein said functionally-graded coating comprises multiple layers of a bone conducting material and a bone stimulating agent disposed within at least one of said multiple layers, wherein a concentration of said bone stimulating agent is different in at least two of said multiple layers; and, wherein said functionally-graded coating further comprises a silver specie in at least one of said multiple layers, said silver specie including, but not limited to a silver salt, silver nitrate, silver perchlorate, silver acetate, silver tetrafluoroborate, silver trifoliate, silver fluoride, silver oxide, silver hydroxide, other silver-"oxo"

species, silver sulfadiazine, mixtures of silver with other stabilizing ligands, and combinations thereof.

Functionally-Graded Analgesic Coatings

Embodiment 64

According to a sixty-forth embodiment of the present invention, there is provided, a medical implant having one or more surfaces comprising a functionally-graded coating disposed thereon, wherein said functionally-graded coating comprises multiple coating layers and an analgesic agent, and wherein a concentration of said analgesic agent is different in at least two of said multiple coating layers.

Embodiment 65

According to an sixty-fifth embodiment of the present invention, there is provided, a medical implant having one or more surfaces comprising a functionally-graded coating disposed thereon, wherein said functionally-graded coating comprises multiple coating layers and an analgesic agent, and wherein an outer of said multiple coating layers has a higher concentration of said analgesic agent than an inner of said multiple coating layers.

Embodiment 66

According to a sixty-sixth embodiment of the present invention, there is provided, a medical implant having one or more surfaces comprising a functionally-graded coating disposed thereon, wherein said functionally-graded coating comprises multiple coating layers and an analgesic agent disposed within an outer of said multiple coating layers, wherein an inner of said multiple coating layers does not contain an analgesic agent.

Embodiment 67

According to a sixty-seventh embodiment of the present invention, there is provided, a medical implant having one or more surfaces comprising a functionally-graded coating disposed thereon, wherein said functionally-graded coating comprises multiple coating layers and an analgesic agent, wherein a concentration of said analgesic agent is different in at least two of said multiple coating layers, and wherein the analgesic agent may be selected from a local anesthetic, such as bupivacaine (e.g. Marcain, Marcaine, Sensorcaine and Vivacaine), a narcotic analgesic such as an opioid, morphine, codeine, oxycodone (Percodan), levorphanol (levodromoran), propoxyphene (Darvon), and pentazocine (Talwin), a non-narcotic analgesic such as acetylsalicylic acid (aspirin), phenylbutazone (Butazolidine), indomethacin (Indocin), acetaminophen, phenacetin, etc, and combinations thereof.

Embodiment 68

According to a sixty-eighth embodiment of the present invention, there is provided, a medical implant having one or more surfaces comprising a functionally-graded coating disposed thereon, wherein said functionally-graded coating comprises multiple coating layers and an analgesic agent, wherein a concentration of said analgesic agent is different in at least two of said multiple coating layers, wherein the analgesic agent may be selected from a narcotic analgesic such as an opioid, morphine, codeine, oxycodone (Percodan), levorphanol (levodromoran), propoxyphene (Darvon), and pentazocine (Talwin), a non-narcotic analgesic such as acetylsalicylic acid (aspirin), phenylbutazone (Butazolidine), indomethacin (Indocin), acetaminophen, phenacetin, etc, and combinations thereof; wherein the functionally-graded coating further comprises an antimicrobial agent such as silver, copper, zinc, manganese, gold, iron, nickel, cobalt, cadmium, and platinum, and combinations thereof; and, wherein a maximum concentration of the antimicrobial agent within the functionally-graded coating may generally be between about 0.1 to about 10 weight percent, and more preferably between about 0.5 to about 3 weight percent.

Embodiment 69

According to a sixty-ninth embodiment of the present invention, there is provided, a medical implant having one or more surfaces comprising a functionally-graded coating disposed thereon, wherein said functionally-graded coating comprises multiple coating layers and an analgesic agent, wherein a concentration of said analgesic agent is different in at least two of said multiple coating layers, and wherein the functionally-graded coating further comprises an antibiotic such as vancomycin, gentamycin, penicillins, cephalosporins, aminoglycoside, macrolides, clindamycin, tetracyclines, chloramphenicol, spectinomycin, polypeptide antibiotics, fluoroquinolones, and combinations thereof.

Embodiment 70

According to a seventieth embodiment of the present invention, there is provided, a medical implant having one or more surfaces comprising a functionally-graded coating disposed thereon, wherein said functionally-graded coating comprises multiple coating layers and an analgesic agent, wherein a concentration of said analgesic agent is different in at least two of said multiple coating layers, and wherein the functionally-graded coating further comprises an anti-fungal such as amphotericin B, nystatin, liposomal amphotericin B, flucytosine, and combinations thereof.

Embodiment 71

According to a seventy-first embodiment of the present invention, there is provided, a medical implant having one or more surfaces comprising a functionally-graded coating disposed thereon, wherein said functionally-graded coating comprises multiple coating layers and an analgesic agent, wherein a concentration of said analgesic agent is different in at least two of said multiple coating layers, and wherein the functionally-graded coating further comprises an anti-viral such as acyclovir, ganciclovir, idoxuridine, amantadin, interferons, azidothymidine, and combinations thereof.

Embodiment 72

According to a seventy-second embodiment of the present invention, there is provided, a medical implant having one or more surfaces comprising a functionally-graded coating disposed thereon, wherein said functionally-graded coating comprises multiple coating layers and an analgesic agent, wherein a concentration of said analgesic agent is different in at least two of said multiple coating layers, wherein the functionally-graded coating further comprises an antimicrobial agent such as a silver salt, silver nitrate, silver perchlorate, silver acetate, silver tetrafluoroborate, silver trifoliate, silver fluoride, silver oxide, silver hydroxide, other silver-"oxo" species, silver sulfadiazine, mixtures of silver with other stabilizing ligands other than sulfadiazine, and combinations thereof, silver, copper, zinc, manganese, gold, iron, nickel, cobalt, cadmium, and platinum, or combinations thereof; and, wherein a concentration of said antimicrobial agent is different in at least two of said multiple coating layers.

Embodiment 73

According to a seventy-third embodiment of the present invention, there is provided, a medical implant having one or more surfaces comprising a functionally-graded coating disposed thereon, wherein said functionally-graded coating comprises multiple coating layers and an analgesic agent, wherein a concentration of said analgesic agent is different in at least two of said multiple coating layers, and wherein at least one of said multiple coating layers contains an bone stimulating agent selected from a carbonate, fluoride, silicon, magnesium, strontium, vanadium, lithium, a growth factor (e.g., BMP), a biomimetic peptide, a bioactive, and combinations thereof.

Embodiment 74

According to a seventy-fourth embodiment of the present invention, there is provided, a medical implant having one or more surfaces comprising a functionally-graded coating disposed thereon, wherein said functionally-graded coating comprises multiple coating layers and an analgesic agent, wherein the concentration of said analgesic agent in is different in at least two of said multiple coating layers, wherein at least one of said multiple coating layers contains a bone stimulating agent, and wherein a concentration of said bone stimulating agent is different in at least two of said multiple coating layers.

Embodiment 75

According to a seventy-fifth embodiment of the present invention, there is provided, a medical implant having one or more surfaces comprising a functionally-graded coating disposed thereon, wherein said functionally-graded coating comprises multiple coating layers and an analgesic agent, wherein the concentration of said analgesic agent is different in at least two of said multiple coating layers; and, wherein an outer of said multiple coating layers comprises a higher concentration of a bone stimulating agent than an inner of said multiple coating layers.

Embodiment 76

According to a seventy-sixth embodiment of the present invention, there is provided, a medical implant having one or more surfaces comprising a functionally-graded coating disposed thereon, wherein said functionally-graded coating comprises multiple coating layers and an analgesic agent, wherein the concentration of said analgesic agent is different in at least two of said multiple coating layers; and, wherein said functionally-graded coating further comprises a silver specie including, but not limited to: silver salts, silver nitrate, silver perchlorate, silver acetate, silver tetrafluoroborate, silver trifoliate, silver fluoride, silver oxide, silver hydroxide, other silver-"oxo" species, silver sulfadiazine, mixtures of silver with other stabilizing ligands other than sulfadiazine, and combinations thereof.

Embodiment 77

According to a seventy-seventh embodiment of the present invention, there is provided, a functionally-graded coating applied to one or more surfaces of a medical implant, wherein said functionally-graded coating comprises multiple layers of a bone conducting material and an analgesic agent disposed within at least one of said multiple layers, wherein a concentration of said analgesic agent is different in at least two of said multiple layers, and wherein the bone conducting material may optionally be selected from any one or more of calcium phosphate, hydroxyapatite, β tricalcium phosphate, a mixture of hydroxyapatite and β tricalcium phosphate, resorbable polymers, bioglass, derivatised phosphate-based compound, orthophosphates, monocalcium phosphates, octacalcium phosphates, dicalcium phosphate hydrate (brushite), dicalcium phosphate anhydrous (monetite), anhydrous tricalcium phosphates, whitlocktite, tetracalcium phosphate, amorphous calcium phosphates, fluoroapatiete, chloroapatite, non-stoichiometric apatites, carbonate apatites, biologically-derived apatite, calcium hydrogen phosphate, calcium hydrogen apatite, water insoluble ceramics, phosphates, polyphosphates, carbonates, silicates, aluminates, borates, zeolites, bentonite, kaolin, and combinations thereof.

Embodiment 78

According to a seventy-eighth embodiment of the present invention, there is provided, a functionally-graded coating applied to one or more surfaces of a medical implant, wherein said functionally-graded coating comprises multiple layers of a bone conducting material and an analgesic agent disposed within at least one of said multiple layers, wherein a concentration of the analgesic agent is greater in an outer of said multiple layers than a concentration of the analgesic agent in an inner of said multiple coating layers.

Embodiment 79

According to a seventy-ninth embodiment of the present invention, there is provided, a functionally-graded coating applied to one or more surfaces of a medical implant, wherein said functionally-graded coating comprises multiple layers of a bone conducting material and an analgesic agent disposed within an outer of said multiple layers, wherein the bone conducting material may be selected from the group of calcium phosphate, hydroxyapatite, β tricalcium phosphate, a mixture of hydroxyapatite and β tricalcium phosphate, resorbable polymers, bioglass, derivatised phosphate-based compound, orthophosphates, monocalcium phosphates, octacalcium phosphates, dicalcium phosphate hydrate (brushite), dicalcium phosphate anhydrous (monetite), anhydrous tricalcium phosphates, whitlocktite, tetracalcium phosphate, amorphous calcium phosphates, fluoroapatiete, chloroapatite, non-stoichiometric apatites, carbonate apatites, biologically-derived apatite, calcium hydrogen phosphate, calcium hydrogen apatite, water insoluble ceramics, phosphates, polyphosphates, carbonates, silicates, aluminates, borates, zeolites, bentonite, kaolin, and combinations thereof; and, wherein an inner of said multiple layers does not contain an analgesic agent.

Embodiment 80

According to an eightieth embodiment of the present invention, there is provided, a functionally-graded coating applied to one or more surfaces of a medical implant, wherein said functionally-graded coating comprises multiple layers of a bone conducting material and an analgesic agent disposed within at least one of said multiple layers, wherein a concentration of said analgesic agent is different in at least two of said multiple layers, wherein the bone conducting material may be selected from the group of calcium phosphate, hydroxyapatite, β tricalcium phosphate, a mixture of hydroxyapatite and β tricalcium phosphate, resorbable polymers, bioglass, derivatised phosphate-based compounds, orthophosphates, monocalcium phosphates, octacalcium phosphates, dicalcium phosphate hydrate (brushite), dicalcium phosphate anhydrous (monetite), anhydrous tricalcium phosphates, whitlocktite, tetracalcium phosphate, amorphous calcium phosphates, fluoroapatiete, chloroapatite, non-stoichiometric apatites, carbonate apatites, biologically-derived apatite, calcium hydrogen phosphate, calcium hydrogen apatite, water insoluble ceramics, phosphates, polyphosphates, carbonates, silicates, aluminates, borates, zeolites, bentonite, kaolin, and combinations thereof; wherein the functionally-graded coating further comprises a concentration of an antimicrobial agent such as a silver salt, silver nitrate, silver perchlorate, silver acetate, silver tetrafluoroborate, silver trifoliate, silver fluoride, silver oxide, silver hydroxide, other silver-"oxo" species, silver sulfadiazine, mixtures of silver with other stabilizing ligands, silver, copper, zinc, manganese, gold, iron, nickel, cobalt, cadmium, platinum, and combinations thereof; and, wherein a concentration of said antimicrobial agent is greater in an outer of said multiple layers than a concentration of the antimicrobial agent in an inner of said multiple layers.

Embodiment 81

According to an eighty-first embodiment of the present invention, there is provided, a functionally-graded coating applied to one or more surfaces of a medical implant, wherein said functionally-graded coating comprises multiple layers of a bone conducting material and an analgesic agent disposed within at least one of said multiple layers, wherein a concentration of said analgesic agent is different in at least two of said multiple layers, wherein the bone conducting material may be selected from the group of calcium phosphate, hydroxyapatite, β tricalcium phosphate, a mixture of hydroxyapatite and β tricalcium phosphate, resorbable polymers, bioglass, derivatised phosphate-based compound, orthophosphates, monocalcium phosphates, octacalcium phosphates, dicalcium phosphate hydrate (brushite), dicalcium phosphate anhydrous (monetite), anhydrous tricalcium phosphates, whitlocktite, tetracalcium phosphate, amorphous calcium phosphates, fluoroapatiete, chloroapatite, non-stoichiometric apatites, carbonate apatites, biologically-derived apatite, calcium hydrogen phosphate, calcium hydrogen apatite, water insoluble ceramics, phosphates, polyphosphates, carbonates, silicates, aluminated, borates, zeolites, bentonite, kaolin, and combinations thereof; wherein a concentration of the analgesic agent is greater in an outer of said multiple layers than in an inner of said multiple layers, wherein the functionally-graded coating further comprises an antimicrobial agent such as a silver salt, silver nitrate, silver perchlorate, silver acetate, silver tetrafluoroborate, silver trifoliate, silver fluoride, silver oxide, silver hydroxide, other silver-"oxo" species, silver sulfadiazine, mixtures of silver with other stabilizing ligands, silver, copper, zinc, manganese, gold, iron, nickel, cobalt, cadmium, platinum, and combinations thereof; and, wherein a maximum concentration of the antimicrobial agent within any of said multiple layers of the functionally-graded coating generally ranges between about 0.1 to about 10 weight percent, and more preferably between about 0.5 to about 3 weight percent.

Embodiment 82

According to an eighty-second embodiment of the present invention, there is provided, a functionally-graded coating applied to one or more surfaces of a medical implant, wherein said functionally-graded coating comprises multiple layers of a bone conducting material and an analgesic agent disposed within at least one of said multiple layers, wherein a concentration of said analgesic agent is different in at least two of said multiple layers, and wherein the functionally-graded coating further comprises an antibiotic such as vancomycin, gentamycin, penicillins, cephalosporins, aminoglycoside, macrolides, clindamycin, tetracyclines, chloramphenicol, spectinomycin, polypeptide antibiotics, fluoroquinolones, and combinations thereof.

Embodiment 83

According to an eighty-third embodiment of the present invention, there is provided, a functionally-graded coating applied to one or more surfaces of a medical implant, wherein said functionally-graded coating comprises multiple layers of a bone conducting material and an analgesic agent disposed within at least one of said multiple layers, wherein a concentration of said analgesic agent is different in at least two of said multiple layers, and wherein the functionally-graded coating further comprises an anti-fungal such as amphotericin B, nystatin, liposomal amphotericin B, flucytosine, and combinations thereof.

Embodiment 84

According to an eighty-fourth embodiment of the present invention, there is provided, a functionally-graded coating applied to one or more surfaces of a medical implant, wherein said functionally-graded coating comprises multiple layers of a bone conducting material and an analgesic agent disposed within at least one of said multiple layers, wherein a concentration of said analgesic agent is different in at least two of said multiple coating layers, and wherein the functionally-graded coating further comprises an anti-viral such as acyclovir, ganciclovir, idoxuridine, amantadin, interferons, azidothymidine, and combinations thereof.

Embodiment 85

According to an eighty-fifth embodiment of the present invention, there is provided, a functionally-graded coating applied to one or more surfaces of a medical implant, wherein said functionally-graded coating comprises multiple layers of a bone conducting material and an analgesic agent disposed within at least one of said multiple layers, wherein a concentration of said analgesic agent is different in at least two of said multiple layers; wherein the functionally-graded coating further comprises a bone stimulating agent selected from carbonate, fluoride, silicon, magnesium, strontium, vanadium, lithium, a growth factor (e.g., BMP), a biomimetic peptide, a bioactive, and combinations thereof; wherein a concentration of said bone stimulating agent is different in at least two of said multiple layers; and, wherein the concentration of either or both of the analgesic agent and bone stimulating agent may be greater within an outer of said multiple layers than in an inner of said multiple layers.

Embodiment 86

According to an eighty-sixth embodiment of the present invention, there is provided, a functionally-graded coating applied to one or more surfaces of a medical implant, wherein said functionally-graded coating comprises multiple layers of a bone conducting material and an analgesic agent disposed within at least one of said multiple layers, wherein a concentration of said analgesic agent is different in at least two of said multiple layers, wherein at least one of said multiple layers contains an antimicrobial agent, wherein a concentration of the antimicrobial agent is different for at least two of said multiple layers; and, wherein the concentration of the antimicrobial agent may be greater within an outer of said multiple layers than a concentration of the antimicrobial agent in an inner of said multiple layers.

Embodiment 87

According to an eighty-seventh embodiment of the present invention, there is provided, a functionally-graded coating applied to one or more surfaces of a medical implant, wherein said functionally-graded coating comprises multiple layers of a bone conducting material and an analgesic agent disposed within at least one of said multiple layers, wherein a concentration of said analgesic agent is different in at least two of said multiple layers; wherein the analgesic agent may be selected from local anesthetics, such as bupivacaine (e.g. Marcain, Marcaine, Sensorcaine and Vivacaine), narcotic analgesics, opioids, morphine, codeine, oxycodone (Percodan), levorphanol (levodromoran), propoxyphene (Darvon), and pentazocine (Talwin), non-narcotic analgesics, acetylsalicylic acid (aspirin), phenylbutazone (Butazolidine), indomethacin (Indocin), acetaminophen, phenacetin, etc, and combinations thereof; wherein at least one of the multiple layers contains a bone stimulating agent which may be selected from a carbonate, fluoride, silicon, magnesium, strontium, vanadium, lithium, a growth factor (e.g., BMP), a biomimetic peptide, a bioactive, and combinations thereof; wherein the functionally-graded coating further comprises an antimicrobial agent such as a silver salt, silver nitrate, silver perchlorate, silver acetate, silver tetrafluoroborate, silver trifoliate, silver fluoride, silver oxide, silver hydroxide, other silver-"oxo" species, silver sulfadiazine, mixtures of silver with other stabilizing ligands, silver, copper, zinc, manganese, gold, iron, nickel, cobalt, cadmium, platinum, and combinations thereof; and, wherein a maximum concentration of the antimicrobial agent within any of said multiple layers of the functionally-graded coating may generally range between about 0.1 to about 10 weight percent, and more preferably between about 0.5 to about 3 weight percent.

Embodiment 88

According to an eighty-eighth embodiment of the present invention, there is provided, a functionally-graded coating applied to one or more surfaces of a medical implant, wherein said functionally-graded coating comprises multiple layers of a bone conducting material and an analgesic agent disposed within at least one of said multiple layers, wherein a concentration of said analgesic agent is different in at least two of said multiple layers; wherein at least one of the multiple layers contains a bone stimulating agent; and, wherein a concentration of either the bone stimulating agent is different in at least two of said multiple layers.

Embodiment 89

According to an eighty-ninth embodiment of the present invention, there is provided, a functionally-graded coating applied to one or more surfaces of a medical implant, wherein said functionally-graded coating comprises multiple layers of a bone conducting material and an analgesic agent disposed within at least one of said multiple layers, wherein a concentration of said analgesic agent is different in at least two of said multiple layers; and, wherein an outer of said at multiple layers comprises a narcotic analgesic agent, and an inner of said at multiple layers comprises a non-narcotic analgesic agent.

Embodiment 90

According to a ninetieth embodiment of the present invention, there is provided, a functionally-graded coating applied to one or more surfaces of a medical implant, wherein said functionally-graded coating comprises multiple layers of a bone conducting material and an analgesic agent disposed within at least one of said multiple layers, wherein a concentration of said analgesic agent is different in at least two of said multiple layers; and, wherein said functionally-graded coating further comprises a silver specie in at least one of said multiple layers, said silver specie including, but not limited to a silver salt, silver nitrate, silver perchlorate, silver acetate, silver tetrafluoroborate, silver trifoliate, silver fluoride, silver oxide, silver hydroxide, other silver-"oxo" species, silver sulfadiazine, mixtures of silver with other stabilizing ligands, and combinations thereof.

While only a few examples of carriers have been illustrated and discussed herein, it is appreciated that other carriers could be advantageously utilized. There are numerous combinations which may become obvious from the disclosure provided herein, each of which may provide a particular solution to address patient-specific needs on an individual basis. As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. For example, the gradient coating (20, 80, 120, 2000) of the present invention may further comprise a gradient of any substances including, but not limited to: analgesics, anesthetics, antimicrobial agents, antibodies, anticoagulants, antifibrinolytic agents, anti-inflammatory agents, antiparasitic agents, antiviral agents, cytokines, cytotoxins or cell proliferation inhibiting agents, chemotherapeutic agents, hormones, interferons, and combinations thereof, BMPs), angiogenesis promoters, antibiotics, and combinations thereof. Alternatively, the methods for providing the gradient coating may vary. Examples include but are not limited to: first firing a ceramic to a metal implant, then subsequently applying another non-fired ceramic, and then applying a polymer layer; or, first firing a ceramic to a metal implant, then subsequently applying two different polymer layers; or, first firing a ceramic to a metal implant, then subsequently applying a first non-fired ceramic layer, and then applying a second non-fired ceramic layer; or, first firing a ceramic to a metal implant, then subsequently applying a polymer layer, and then applying a non-fired ceramic; and obvious variant combinations thereof. It is further to be understood that the term "concentration" where used herein embodies weight percentages that include zero percent and one-hundred percent, as well as all weight percentages therebetween.

EXAMPLES

Example I

Gradient Coatings for Biomedical Applications

Figure 15:
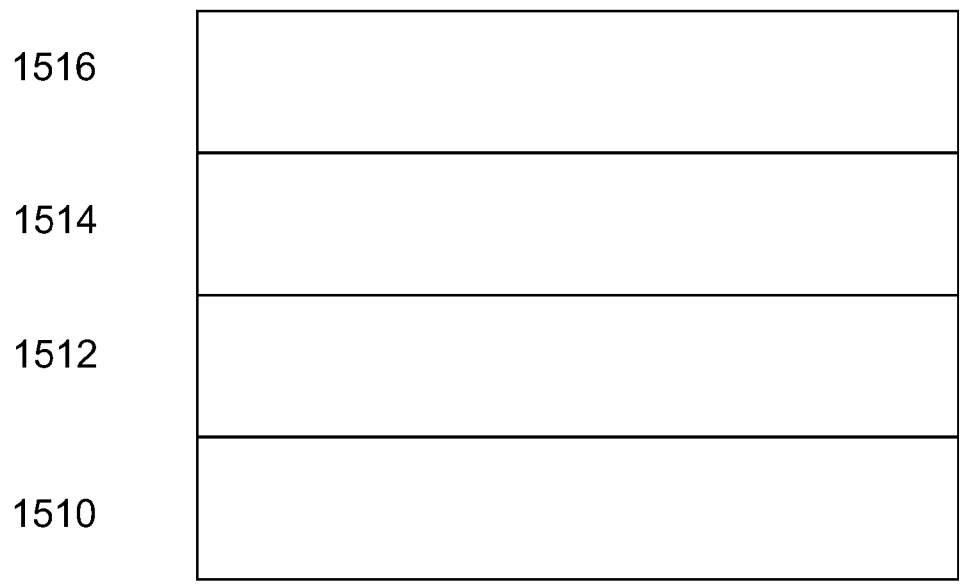
FIG. 15 is a schematic of a further embodiment of the gradient coating of the present invention.

FIG. 15 shows an example of an embodiment of the present invention (an implant substrate (1510) [e.g. Ti6Al4V] with a gradient coating containing VPS HA (1512) and VPS AgHA (1514), and a top layer of PLGA coating contains β-TCP, Ag, and Bupivacaine (1516)) prepared by the following method:

1. HA/Ag-HA coating preparation: The Ag-HA powders (45-125 μm) were modified using an ion exchange reaction. The coating process parameters were the same as the standard vacuum plasma sprayed HA coatings produced at our manufacturing facility for medical implants. VPS HA coating was first applied and then followed by the VPS Ag-HA coating. The coated sample was ready for the PLGA coating.

2. Silver modified β-TCP powder preparation:
   1). 0.5 g β-TCP powder ($D_{50}$~3 μm) and 145.8 mg silver nitrate were dissolved into 55 mL de-ionized and distilled water and stirred for 1 hour at 60° C.
   2). The water was evaporated overnight at 60° C.
   3). The dry powder was then ground. Alternatively, the silver modified β-TCP can also be freeze dried to remove the water and the grinding step is not necessary.
   4). The silver modified powder was subsequently sintered at 400° C. for 2 hours.

3. PLGA solution preparation:
   1). 0.75 g PLGA pellets (85:15) were dissolved in 15 mL of dichloromethane and stirred overnight.
   2). The 0.25 g silver modified β-TCP and 100 mg Bupivacaine powder were dissolved into the PLGA solution and stirred overnight. Asdasd 4. PLGA coating application: The VPS HA/VPS Ag-HA coated Ti6Al4V substrate was dipped into the PLGA solution and withdrawn vertically and then dry in air overnight.

Figure 16:
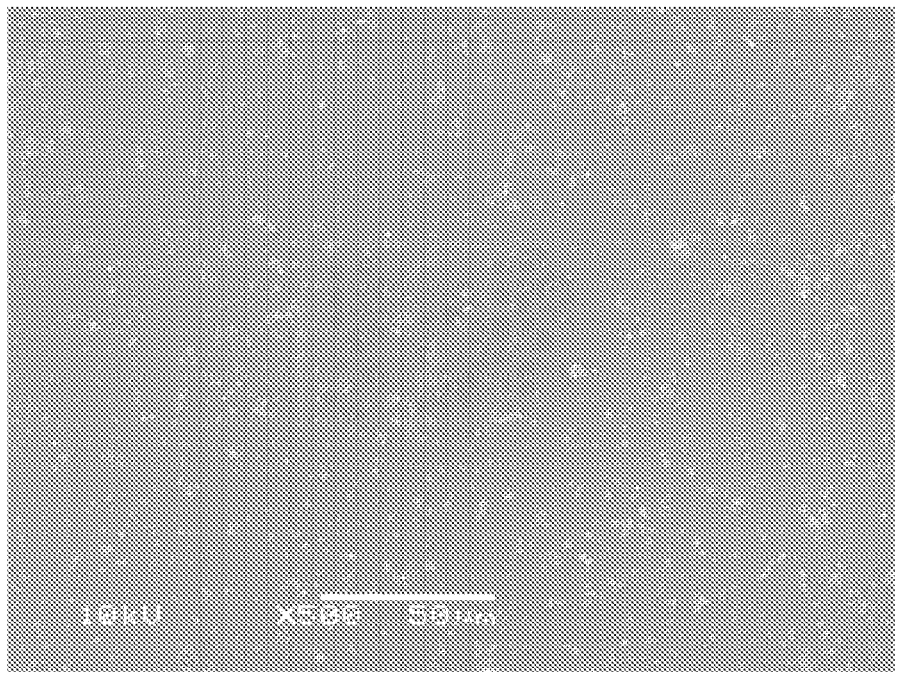
FIG. 16 is a low magnification of the top PLGA coating containing silver modified beta-TCP and Bupivacaine.
Figure 17:
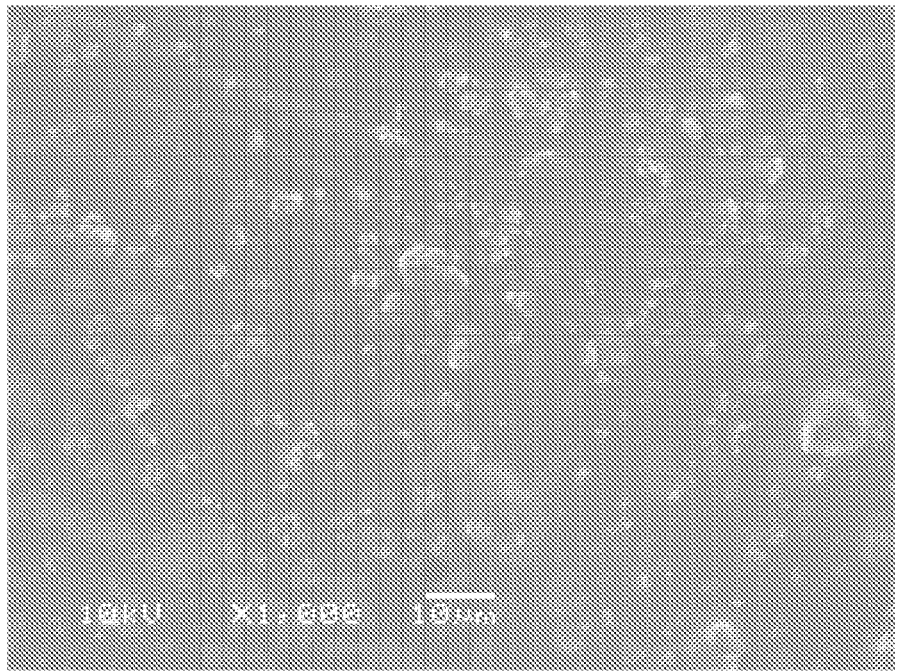
FIG. 17 is a high magnification of the top PLGA coating containing silver modified beta-TCP and Bupivacaine.

Results: The surface morphology of the top PLGA layer is shown in FIGS. 16 and 17. A quantitative analysis obtained from an EDXA spectrum is shown in Table 2.

TABLE 2

EDXA result of the top PLGA coating

| Element | Wt % |
|---|---|
| CK | 65.23 |
| OK | 26.17 |
| PK | 3.09 |
| AgL | 1.04 |
| CaK | 4.48 |

Example II

Figure 18:
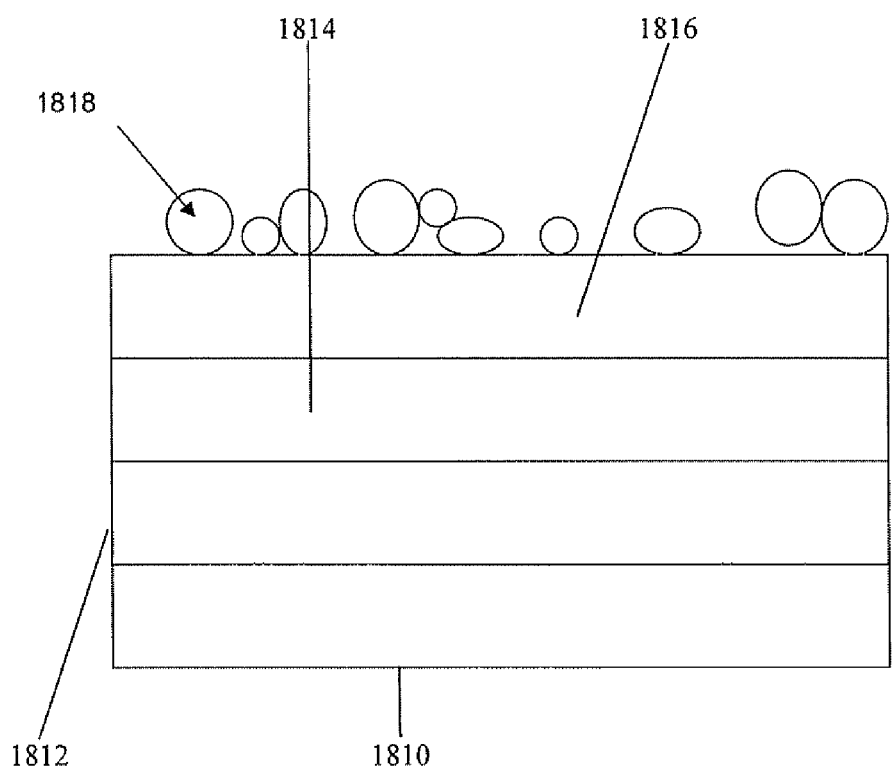
FIG. 18 is a schematic of another embodiment of the present invention.

FIG. 18 shows another embodiment of the present invention (an implant substrate (1810) [e.g. Ti6Al4V] with a gradient coating containing VPS HA (1812) and VPS AgHA (1814), and a layer of PLGA coating contains β-TCP, Ag, and Bupivacaine (1816), and a PLGA beads layer containing β-TCP, Ag, and Bupivacaine (1818)).

This is an example to demonstrate that the amount and release duration of Ag and Bupivacaine can be controlled by increasing the total coating surface area through adding PLGA beads on the top surface of the PLGA coating. Bupivacaine was known to have a quick release profile in the body environment. In order to have a continuous prolonged release, Bupivacaine was incorporated into the PLGA beads to slow down its degradation rate in the body environment.

Method

1. PLGA beads preparation:
   1) The silver modified β-TCP powder was prepared in the same way as in the Example 1.
   2) The 0.25 g silver modified β-TCP and 100 mg Bupivacaine powder were dissolved into the PLGA solution (0.75 g PLGA in 15 mL dichloromethane) and stirred overnight.
   3) 5 g Sodium Dodecyl Sulfate (SDS) was dissolved into 500 mL de-ionized and distilled water.
   4) The PLGA solution containing the silver modified β-TCP and Bupivacaine powder was added into the SDS solution drop by drop with a vigorous stir. The beads formed from the water-oil-water double emulsification were washed and collected after 24 hours stirring in the 1% SDS.
   5) The collected PLGA beads were applied onto the top PLGA coating which also contains silver modified β-TCP and Bupivacaine.
   6) The PLGA beads were sintered together and to the PLGA coating at 70° C. for 12 hours.

Figure 19:
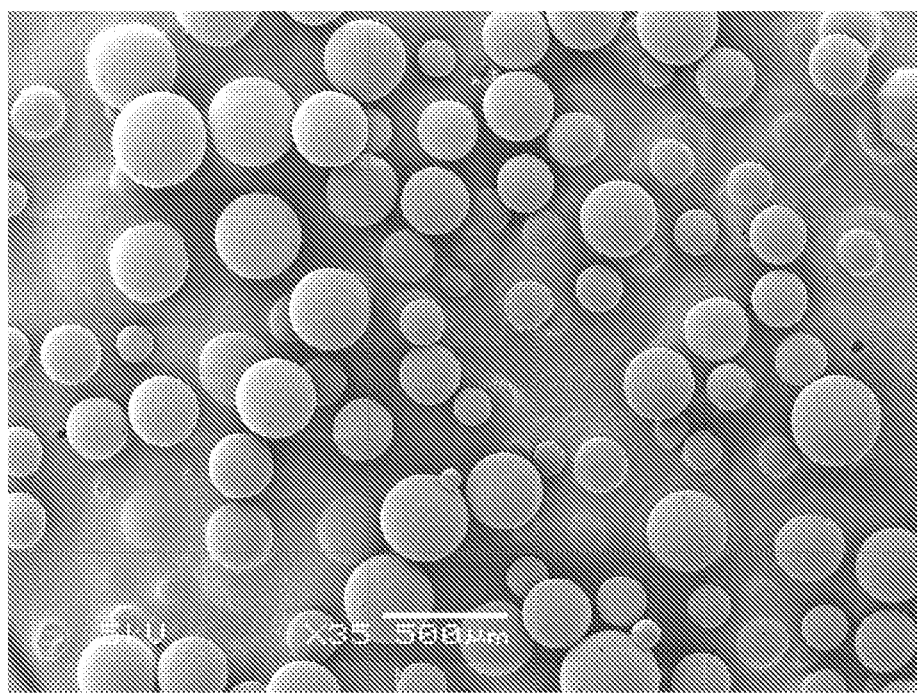
FIG. 19 is a low magnification of the top view of the PLGA beads on a PLGA coating.
Figure 20:
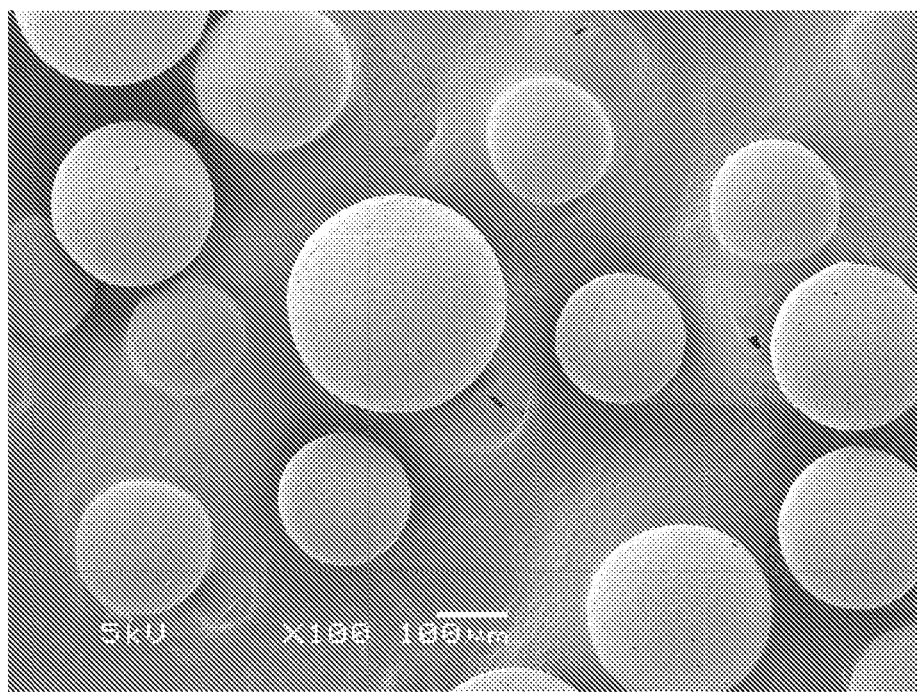
FIG. 20 is a high magnification of the top view of the PLGA beads on a PLGA coating.
Figure 21:
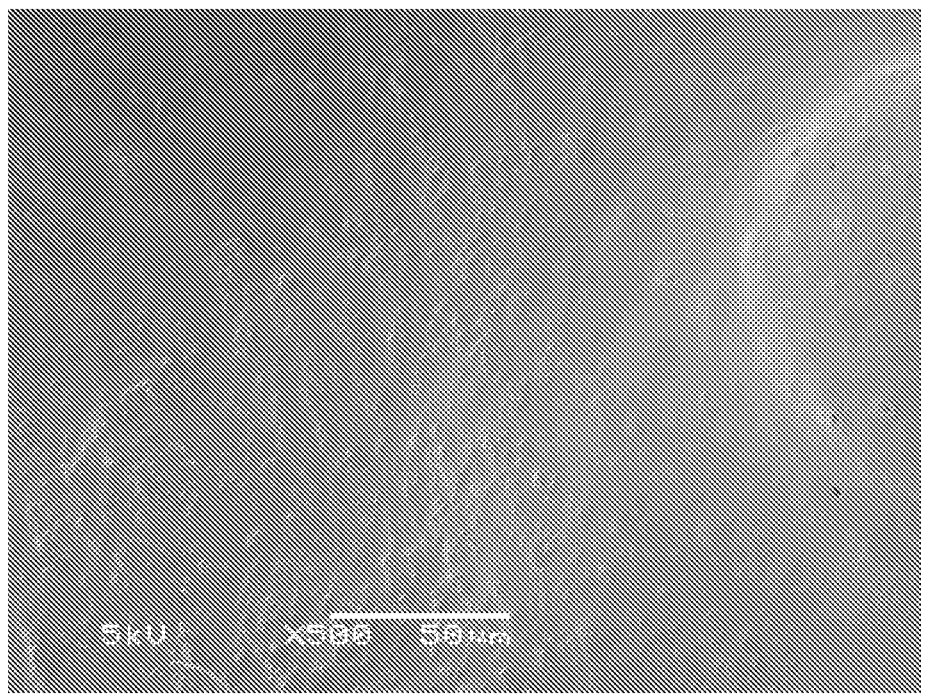
FIG. 21 is a high magnification of the PLGA coating.
Figure 22:
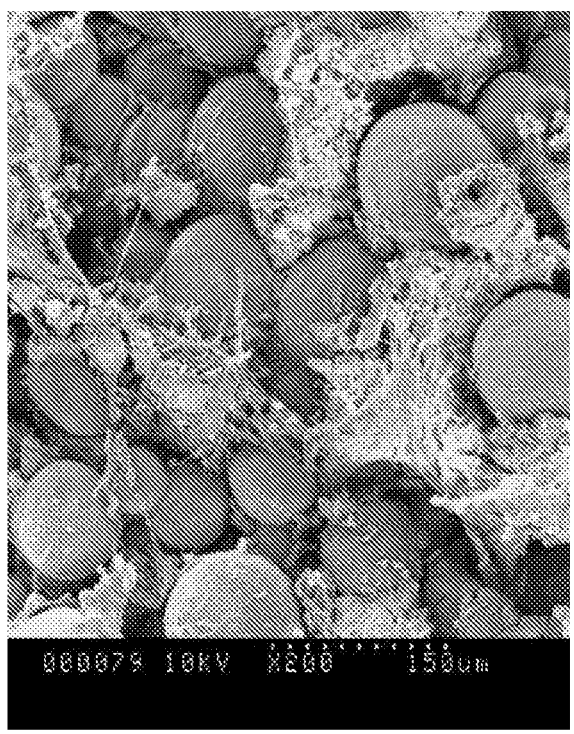
FIGS. 22 (a) and (b) are SEM images from 9-day pulled out implant: Low Ag-modified calcium phosphate-coated implant from Rabbit #1A.
Figure 22:
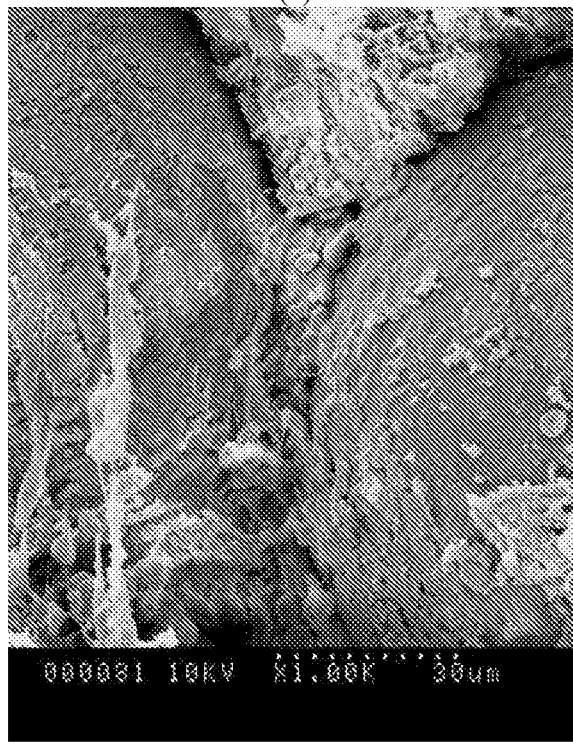
Figure 23:
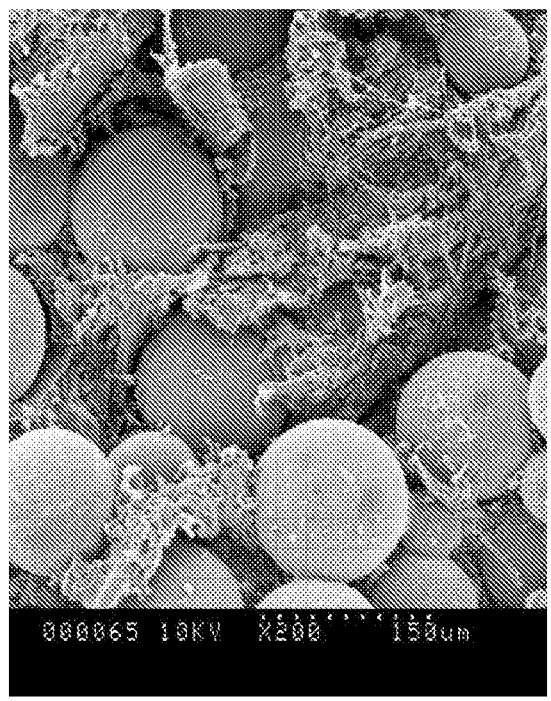
FIGS. 23 (a) and (b) are SEM images from 9-day pulled out implant: non-calcium phosphate-coated implant from Rabbit #1A.
Figure 23:
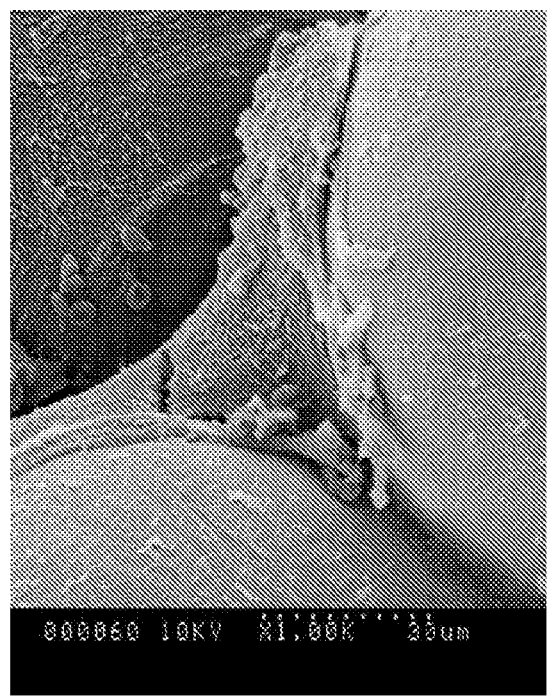
Figure 24:
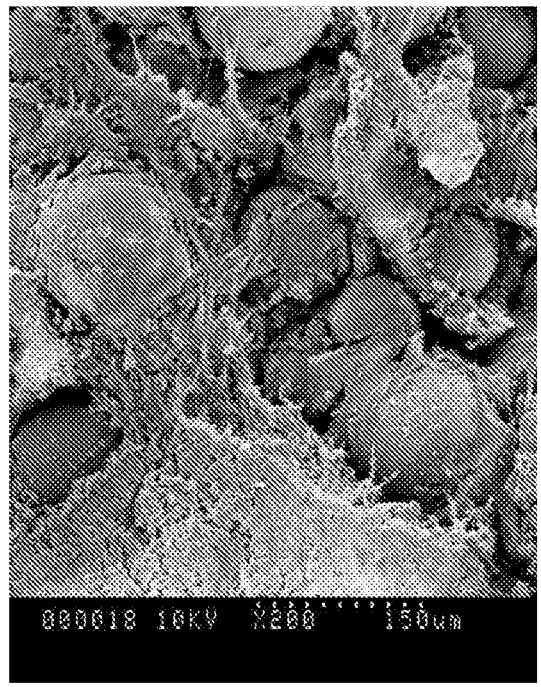
FIGS. 24 (a) and (b) are SEM images from 9-day pulled out implant: High Ag-modified calcium phosphate-coated implant from Rabbit #1B.
Figure 24:
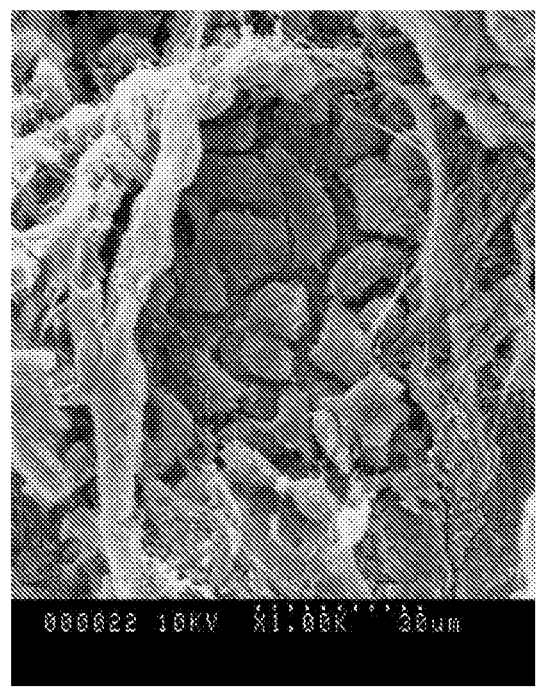
Figure 25:
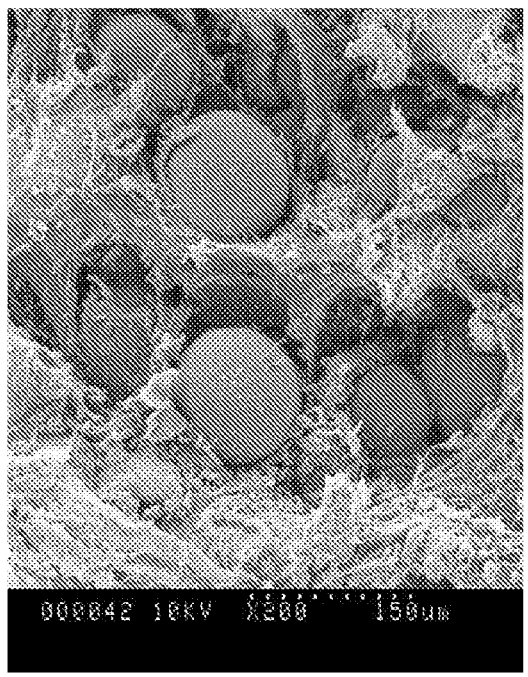
FIGS. 25 (a) and (b) are SEM images from 9-day pulled out implant: non-calcium phosphate-coated implant from Rabbit #1B.
Figure 25:
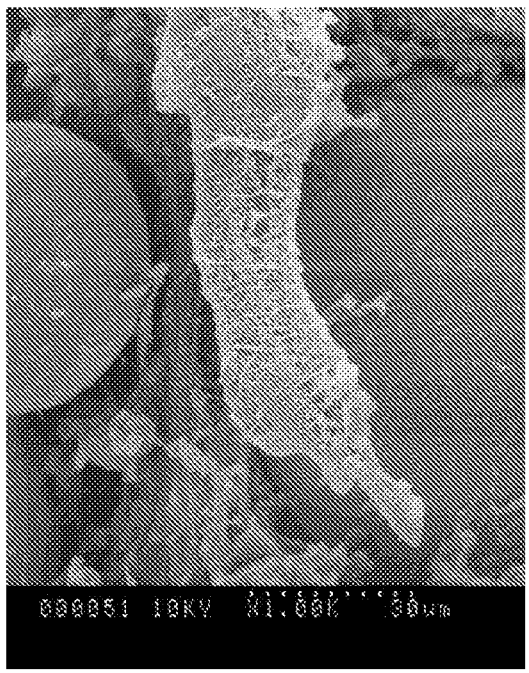
Figure 26:
FIG. 26 is a back-scattering SEM of a 'low' S-CP, 9 days. (Sample 4A Right). Small regions of mineralized tissue (bone) (arrows) within regions of the porous coat. Dashed lines shows the position of host bone after site drilling.
Figure 27:
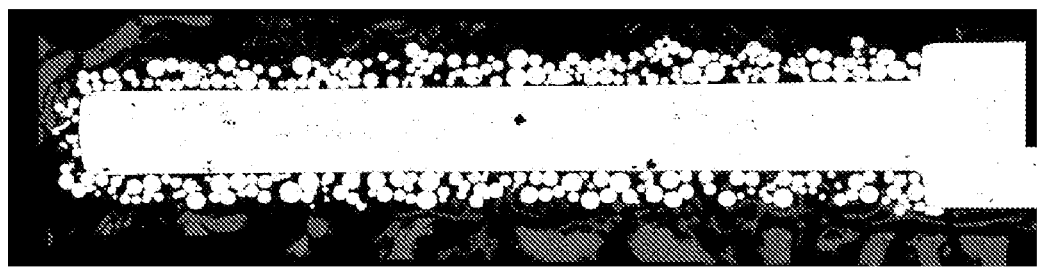
FIG. 27 is a back-scattering SEM of a 'high' S-CP, 9 days. (Sample 5B Left). Small regions of mineralized tissue (bone) (arrows) within regions of the porous coat. Dashed lines shows the position of host bone after site drilling.
Figure 28:
FIG. 28 is a back-scattering SEM of a 'control' (no CP), 9 days. (Sample 5B Right). Small regions of mineralized tissue (bone) (arrows) within regions of the porous coat.
Figure 29:
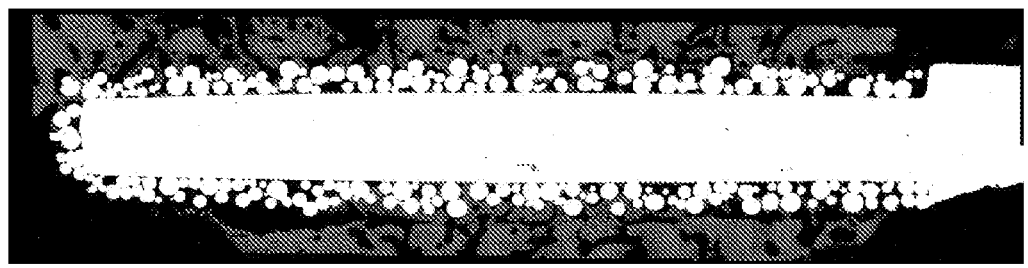
FIG. 29 is a back-scattering SEM of a 'low' S-CP, 16 days. (Sample 9C Right). Extensive bone ingrowth throughout full porous coat depth. Dashed lines shows initial drilled bone border.
Figure 30:
FIG. 30 is a back-scattering SEM of a 'high' S-CP, 16 days. (Sample 8D Right). Extensive bone ingrowth throughout full porous coat depth. Dashed lines show probable initial drilled bone border.
Figure 31:
FIG. 31 is a back-scattering SEM of a 'control' (no CP), 16 days. (Sample 2C Left). Bone ingrowth throughout depth of porous coating; difficult to identify initial drilled bone border.
Figure 32:
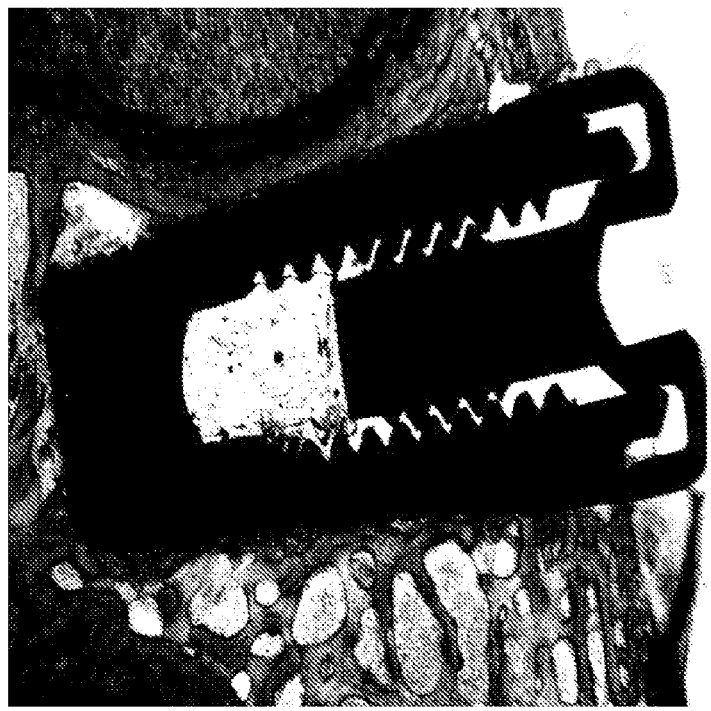
FIGS. 32 (a) and (b) show a 9-day sintered porous-coated Ti6Al4V 'control' implant—(a) and (b) Sample 5B Right—the blue-green stained areas are bone (old and newly-formed). Due to the section thickness, some bone does not show the staining effect and appears grey. A small amount of fibrous tissue is present near the interface in some regions (arrow).
Figure 32:
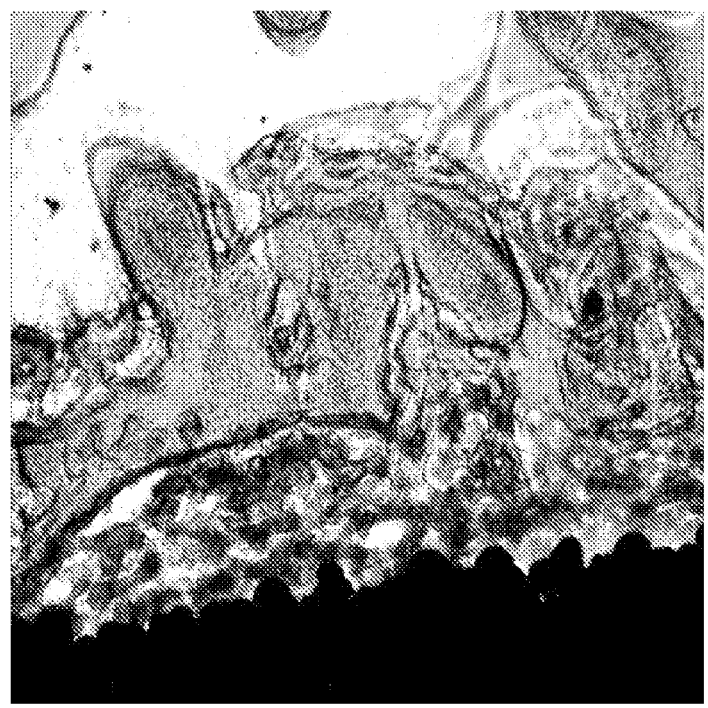
Figure 33:
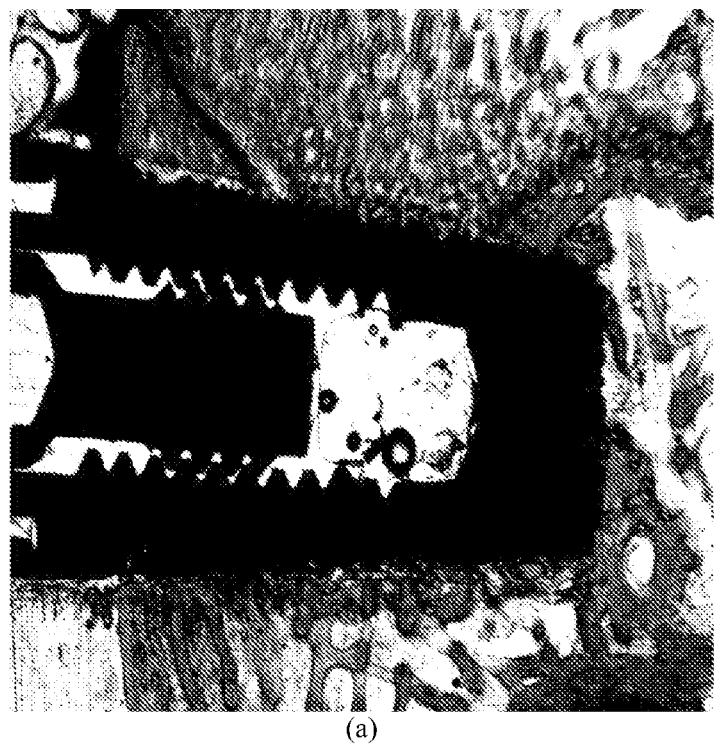
FIGS. 33 (a) and (b) show the 9-day sintered porous-coated Ti6Al4V implant with 'low' S-CP over-layer—(a) Sample 8A Left, (b) sample 4A Right—In (b), the extent of original bone loss due to drilling (and possibly some bone die-back) is evident by the truncated trabeculae.
Figure 33:
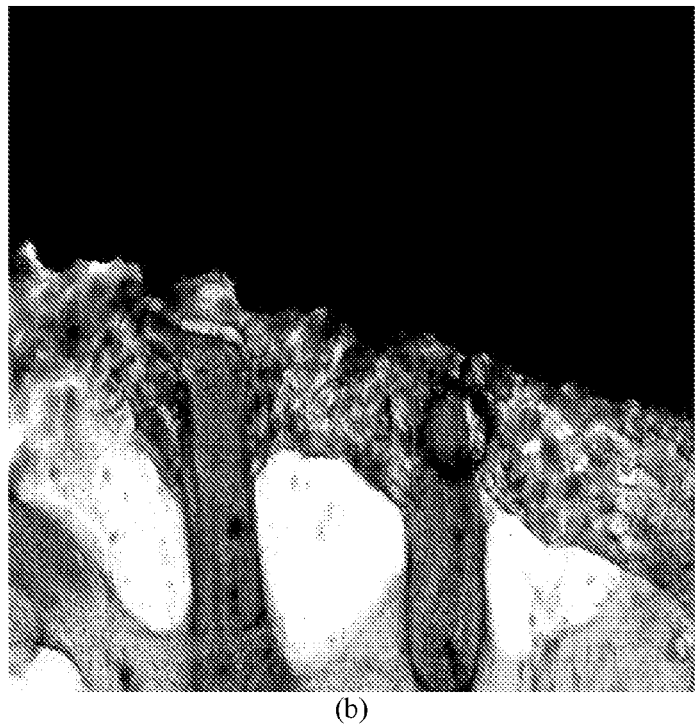
Figure 34:
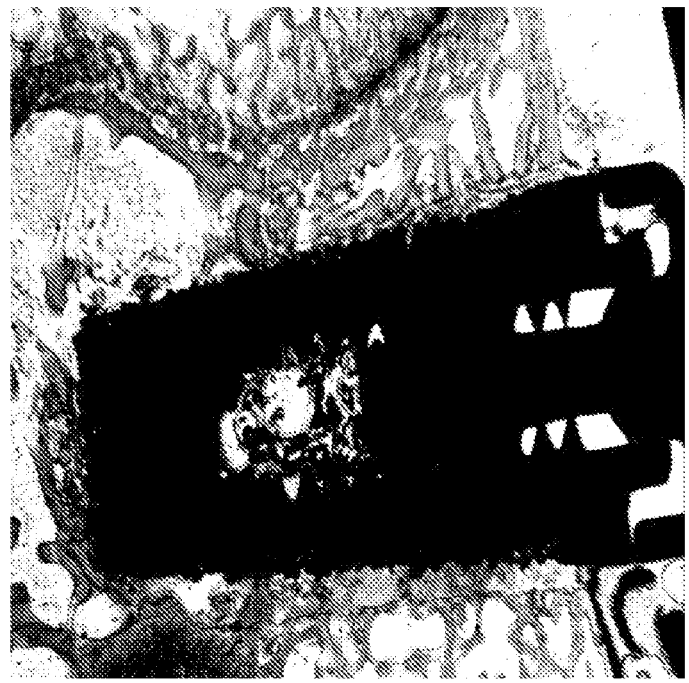
FIGS. 34 (a) and (b) show the 9-day sintered porous-coated Ti6Al4V implant with 'High' S-CP over-layer—(a) & (b) Sample 8B Left—Both the high and low magnification images show the extent of bone loss due to site preparation (drilling) and possibly subsequent bone die-back (dashed line in (b)). Nevertheless, a suitable press-fit was achieved allowing early bone formation within the interface zone and into the porous coat (arrow).
Figure 34:
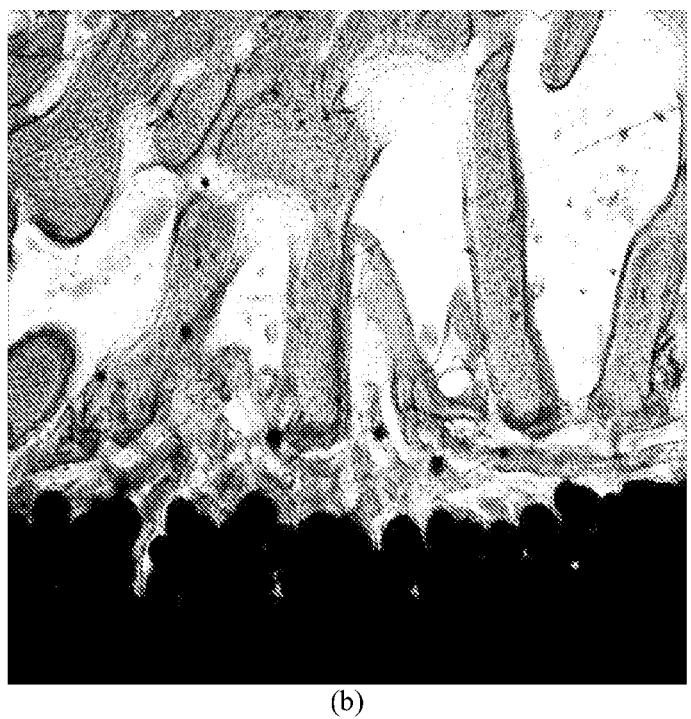
Figure 35:
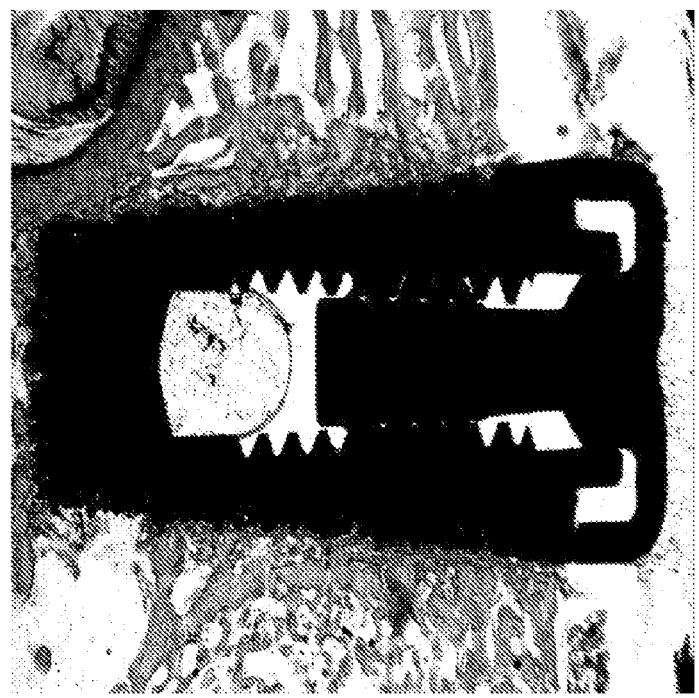
FIGS. 35 (a) and (b) show the 16-day sintered porous-coated Ti6Al4V implant 'control' implant—(a) & (b) Sample 2C Left—Extensive new bone formation and ingrowth throughout the porous coat (blue-green stained areas).
Figure 35:
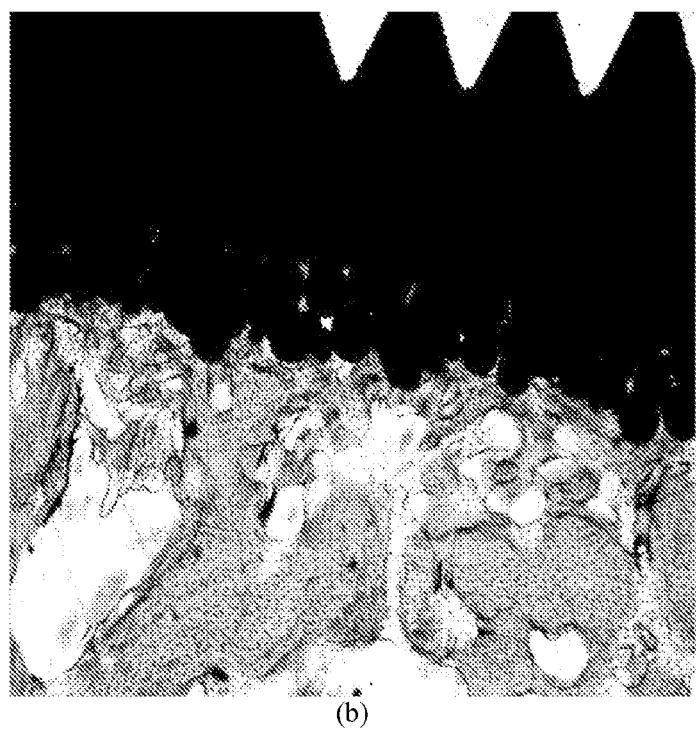
Figure 36:
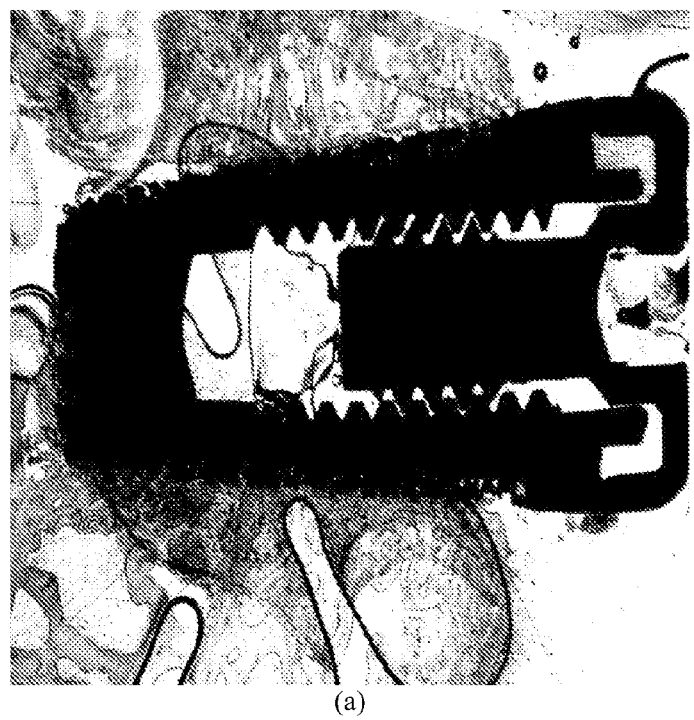
FIGS. 36 (a) and (b) show the 16-day sintered porous-coated Ti6Al4V implant with 'Low' S-CP over-layer—(a) & (b) Sample 9C Right—Extensive new bone formation and ingrowth. [Sample embedding artifacts (air bubbles) seen in (a)].
Figure 36:
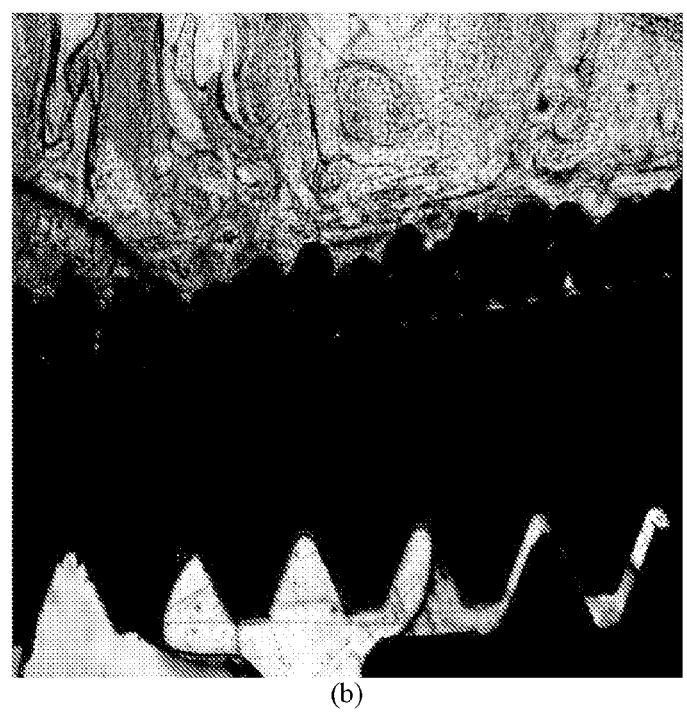
Figure 37:
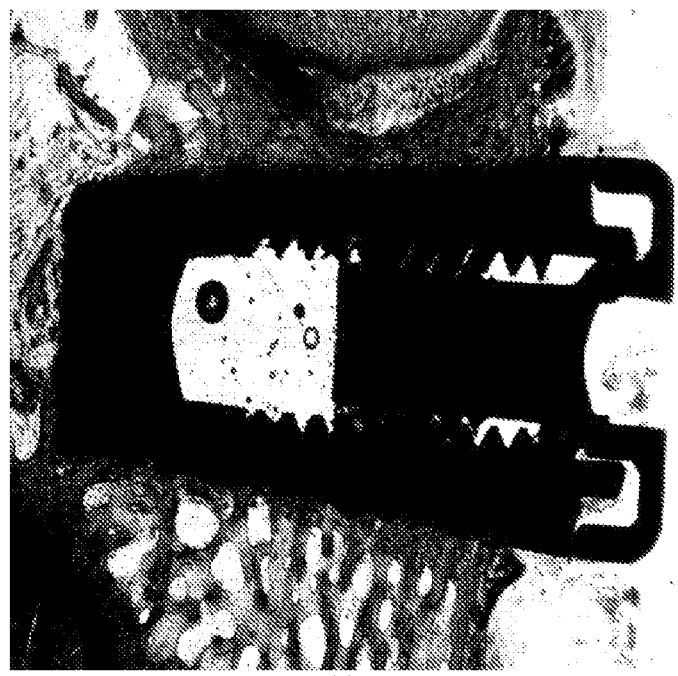
FIGS. 37 (a) and (b) show the 16-day sintered porous-coated Ti6Al4V implant with 'High' S-CP over-layer—(a) & (b) Sample 8D Right—Good bone ingrowth along implant length.
Figure 37:
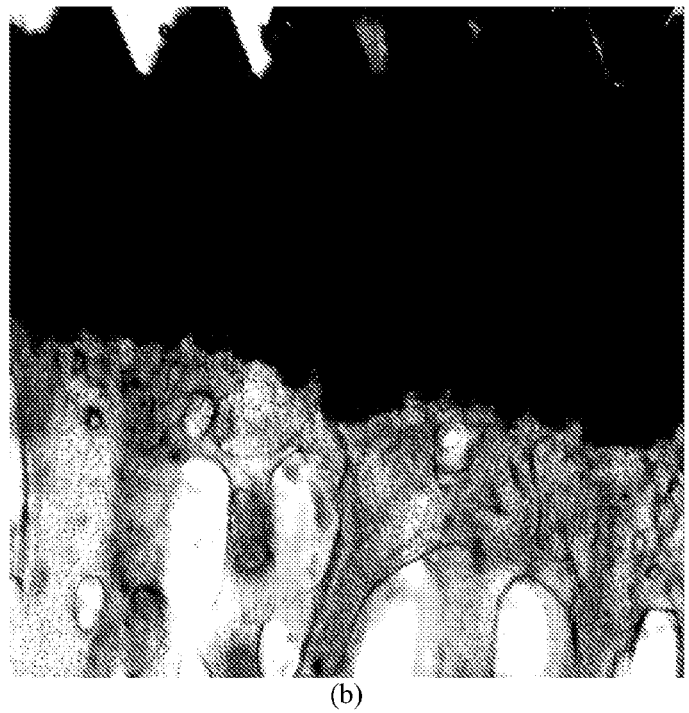

Results: The surface morphology is shown in FIGS. 19, 20, and 21. The surface composition was analyzed using EDXA and the result was shown in Table 3.

TABLE 3

EDXA result of the top PLGA coating

| Element | Wt % |
|---|---|
| CK | 63.76 |
| OK | 26.16 |
| PK | 3.53 |
| AgL | 1.54 |
| CaK | 5.01 |

Example III

Release Profiles

The release of Ag, Ca, and Bupivacaine from the prepared coating was confirmed by ICP analysis and UV spectrometry, respectively.

The coated samples were immersed in 3 mL PBS for 24 and 48 hours at 37° C. At each time point, the release of bupivacaine was measured spectrophotometrically (Nanodrop, Thermo) at 265 nm. The Bupivacaine standard was prepared by dissolving appropriate amounts of the drug in PBS. PBS was used as blank. The Bupivacaine concentration is shown in Table 4.

TABLE 4

The Bupivacaine concentration in PBS at 24 and 48 hours

| | Bupivacaine Concentration (ppm) |
|---|---|
| 24 Hours | 126 |
| 48 Hours | 141 |

The Ag, Ca, and P concentration in PBS at 24 and 48 hours were shown in Table 5.

TABLE 5

The silver and calcium concentration (ppm) in PBS at 24 and 48 hours

| | Ag | Ca |
|---|---|---|
| 24 Hours | 0.393 | 1.58 |
| 48 Hours | 0.392 | 1.35 |

The degradation study confirmed the coating was able to release Bupivacaine for analgesic effect, Ag ions for antimicrobial effect, and Ca for osteoconductive effect.

Example IV

Example of Method of Synthesis and Characterization

Synthesis
1). VPS gradient coating: Ti6Al4V substrate+pure VPS HA layer+3% VPS AgHA layer (This has been done)
2). Dissolve PLGA (85:15) pellets in dichloromethane and stir overnight
3). Soak and stir β-TCP in silver nitrate solution for 2 hours to allow ion-exchange reaction
3). Add Bupivacaine into the above TCP+silver nitrate solution
4). Dry the Bupivacaine+TCP+silver nitrate solution overnight
5). Add the dry powder of Bupivacaine+TCP+silver nitrate to the dissolved PLGA solution and stir overnight
6). Dip coat the VPS gradient coating using the above PLGA solution with Bupivacaine+TCP+silver nitrate Characterization
1). SEM top view and cross section
2). EDAX—elemental composition of top layer and cross section (Ca, P, Ag)
3). XRD-Phase composition of the top layer (mainly to detect bupivacaine)
4). Alternative to XRD: dissolution of top layer in PBS (3 days) and subsequent spectroscopic analysis of bupivacaine

Example V

Further Example of Method of Synthesis and Characterization

Synthesis
1). Sol-gel dip coating process to make a Ag graded coating, i.e. Ti6Al4V substrate+pure Ca—P layer+2% Ag—Ca—P layer
2). Dissolve PLGA (85:15) pellets in Chloroform
3). Add analgesic (e.g. over counter Tylenol) and Ag—CaP (2 wt % Ag) powders into the PLGA
4). Dip coat the sol-gel Ag—Ca—P sample using the prepared PLGA polymer solution.

Characterization
1). SEM top view before and after degradation in PBS and SBF
2). ToF-SIMS to obtain depth information
3). XRD-Phase composition (This has been done)
4). In vitro bioactivity evaluation in SBF (3 days)
5). Dissolution in PBS (24 h, 48 h, 72 h) to measure Ag concentration.

Example VI

Osseointegration of Porous-Surfaced Implants with Modified Anti-Microbial Calcium Phosphate Coatings The results of mechanical pull-out testing of Ti6Al4V alloy porous-surfaced implants prepared with or without sol-gel-formed Ag-modified calcium phosphate thin film overlayers (approximately 1 micron thick) are reported herein. Briefly summarizing, the study used 4 groups of 10 rabbits that had porous-surfaced implants (Endopore® dental implants acquired from Innova-Sybron Dental Products) implanted transversely in their medial femoral condyles, (porous region interfacing with cancellous bone). Implant positioning and implantation procedures were similar to those described in Tache et al (2004), Int J Oral Maxillofac Implants, 19:19-29; Gan et al (2004), Part II: Short-term in vivo studies, Biomaterials, 25:5313-5321; Simmons et al (1999), J Biomed Mater Res., 47:127-138, all of which are herein incorporated by reference. 'Test' implants (one per animal in either the right or left leg—random placement) were prepared with Ag-modified calcium phosphate coatings overlaying the sintered porous surface of the Ti alloy implants. The porous surface region consisted of approximately three layers of Ti6Al4V alloy powders (44 to 150 micron particle size) sintered so as to form a porous layer approximately 300 micron thick with 35 volume percent porosity (approximate) and with average pore size in the 75 to 100 microns range. The interconnected open-pored structure was suitable for achieving implant fixation by uninhibited bone ingrowth. It is noteworthy that this particle and pore size is somewhat smaller than that conventionally used with orthopedic implants but has proved acceptable and, in fact, is preferred for dental implant applications where dimensional constraints arise.

The sol-gel-formed calcium phosphate overlayer had been studied previously (but minus the Ag+ modification) and, in the unmodified form, was observed to promote faster bone ingrowth (i.e. enhanced osseointegration). Based on these earlier studies, Ag-modified calcium phosphate coatings were proposed and developed by Smith & Nephew as anti-microbial and osteoconductive coatings that would both increase bone ingrowth into porous-surfaced implants as well as reduce the possibility of infection at an implant site during the early post-implantation period. This increased infection resistance during the crucial early post-implantation healing period is desirable since microbial ingress resulting in local infection and inflammatory response would inhibit bone ingrowth and potentially result in implant failure. Therefore, reducing the probability of bacterial infections during this early period would be of considerable benefit in improving the reliability of orthopaedic implants designed for fixation through bone ingrowth.

Materials & Methods

Two different Ag+-containing calcium phosphate formulations were investigated. These are designated in this report as 'Low' and 'High' Ag levels. (In the results presented below LC=low Ag+(0.9 wt %) calcium phosphate and HC=high Ag+(2.5 wt %) calcium phosphate coatings). The animal study was designed such that the LC implants were placed in femoral condyles of 20 rabbits with 'control' implants (i.e. no calcium phosphate (NC) sol-gel coating) in the other femur while the HC implants were placed similarly against 'control' implants in the remaining 20 rabbits. Ten rabbits from each group were maintained for 9 days following implant placement and then euthanized while another ten rabbits were maintained for 16 days prior to sacrifice. This provided 10 LC implants after 9-day implantation for comparison against 10 NC 9-day implants and a similar number of LC implants for comparison with NC implants at 16 days. Similarly two groups of 10 HC implants were studied after 9- and 16-day implant residence periods and compared with NC implants.

Implant performance in terms of effective bone ingrowth leading to secure implant fixation was assessed by mechanical pull-out testing (as in the previously reported studies as discussed above) as well as histological examination and assessment of some of the implant-tissue samples after animal sacrifice. Additionally, some of the pulled out implants were examined by secondary electron imaging in the scanning electron microscope to characterize the implant-tissue interface region and to identify any bone-like or fibrous tissue features that might be present. The virtue of the mechanical pull-out testing is that this test provides information on the complete interface rather than the selected area that is observed through microscopic examination. All specimens for mechanical testing were stored in saline solution following animal euthanization and dissection of the femoral condyle region and tested within 2 hours of sacrifice.

Eight of the 10 samples per group as described above were mechanically tested with the remaining two specimens being used for histological sample preparation. Pull-out testing involved mounting the bone-implant samples in a custom-made fixture that ensured proper alignment of the implant and applying a pull-out force under displacement control at a rate of 1 mm/min. The tapered shape of the porous-surfaced implant and the careful sample alignment ensured that frictional forces acting at the bone-implant junction that might have contributed to measured pull-out force and interface stiffness were avoided. Maximum pull-out force and maximum tangential slope of the load-displacement curve were used to determine pull-out resistance and the interface zone stiffness.

Two of the 10 samples per group as described above were collected after rabbit sacrifice and fixed in 10% buffered formalin and processed for embedding in methyl methacrylate. The resulting blocks were sectioned using a diamond wafering blade to produce sections approximately 200 micrometers in thickness along the long axis of the implants at their mid-plane. These samples were then mounted on glass slides and carefully ground and polished to provide non-decalcified sections approximately 30 to 40 microns in thickness. The 'thin' sections were stained with a 1:1 mixture of 0.3% Toluidine blue and 2% sodium borate at 50° C. for 15 minutes, and then stained in 0.3% light green in 2% acetic acid at room temperature for 3 minutes. The sections were examined by light microscopy and appearance recorded as described below.

Statistical analyses (Analysis of Variance with implant design as the one variable parameter) of the maximum pull-out force and measured interface zone stiffness values for the calcium phosphate coated 'test' implants versus the non-coated 'control' implants for the different pairs of implants were undertaken. Thus, the 9-day LC implants were compared with the corresponding 9-day NC implants placed in the contralateral rabbit femoral condyle, the 9-day HC implants were compared with the corresponding 9-day NC implants and the 16-day paired implants were compared in the same way. In addition, the 9-day NC implants were compared with the 16-day NC implants and the 9-day HC implants and 16-day HC implants were compared similarly.

Results & Discussion

The mechanical test results from the current study are presented in Table 6

TABLE 6

Summary of Mechanical Pull-out Tests

| Sample Type | Implant Period (days) | Interface Stiffness (N/mm) (Mean ± SD) | Pull-out Force (N) (Mean ± SD) |
|---|---|---|---|
| Low Ag-CP | 9 | 311 ± 140 | 192 ± 116 † |
| High Ag-CP | 9 | 355 ± 158 | 193 ± 69 # |
| Control-No CP | 9 | 307 ± 99 * | 177 ± 66 ‡ |
| Low Ag-CP | 16 | 355 ± 89 | 402 ± 118 † |
| High Ag-CP | 16 | 432 ± 75 | 413 ± 147 # |
| Control-No CP | 16 | 371 ± 75 * | 469 ± 120 ‡ |

* Significant Difference (p = 0.048)
†, ‡, # Significant Difference between pairs (p < 0.01)

The statistical tests indicated that there were no significant differences for both maximum pull-out force and interface stiffness between the 'test' and 'control' implants for all pairs of samples (significant differences corresponding to p<0.05). However, there was a highly significant increase in pull-out force for the 16-day implants compared with the 9-day samples for both the LC and HC implants (p<0.01). The interface zone stiffness also showed an increase from 9 days to 16 days and while this increase was significant (p=0.048), the difference was not nearly as great as that observed for pull-out resistance. This interesting result suggests that the interface zone develops a stronger resistance to crack propagation and fracture as more extensive tissue and bone ingrowth develops (i.e. a 'tougher' interface zone develops) from 9 to 16 days. The increase from the 9- to 16-day implantation period is consistent with previously reported results with this rabbit femoral condyle implantation model.

Interestingly, the Ag+-modified calcium phosphate overlayer resulted in interface stiffness values after the 16-day implantation period that, while higher on average than the values for the 9-day implants, were not significantly different. The resistance to implant removal by 9 days for both the as-sintered, non-calcium phosphate-coated and the Ag+-modified calcium phosphate coating (Low and High Ag+) indicated that tissue (bone) ingrowth had occurred for the coated implants.

SEM Examination of Pulled Out Implants

Some of the 9-day implants that had been mechanically tested were examined by secondary electron emission scanning microscopy.

FIGS. 22 through 25 show eight of the collected images. FIGS. 22a&b show images of a calcium phosphate-coated, lower Ag+ implant (CL-9) extracted from the 9-day implanted rabbit #1A. While this implant exhibited lower interface stiffness and pull-out force, the secondary electron images nevertheless show extensive tissue attachment and ingrowth with areas displaying the characteristics of mineralized tissue. FIGS. 23a&b are images of the noncoated 'control' implant (NCL-9) extracted from the other knee of the same animal. This implant displayed higher stiffness and pull-out values compared to the coated implant (CL) from the contralateral limb and showed the expected extensive tissue attachment and mineralized tissue ingrowth by the 9-day implant period. FIGS. 24a&b and 25a&b are images of the extracted higher Ag+-containing calcium phosphate coated implant (FIGS. 24a&b) and the corresponding non-coated 'control' implant (FIGS. 25a&b); (Rabbit #1B i.e. containing implants CH-9 and NCH-9 respectively).

BS-SEM Examination of Non-Mechanical Testing Implants

BS-SEM was used to collect images of the tissue-implant interface zone with quantitative image analyses being performed on the examined sections. For the quantitative assessment (Quantimet Image Analysis program), an envelope approximately 220 micrometers wide from the implant substrate along the length of its porous-coated region was selected (i.e. an envelope width that approached the extremity of the porous coat along the implant length but excluded more peripheral regions; the implant ends were also excluded). This region was analyzed using the Quantimet image analysis software. The percent area of bone within the pores was determined (i.e. % [bone area/pore area]). The program also allowed a determination of the percent porosity of the porous coat that was nominally designed to be 35 to 40 volume percent.

FIGS. 26 to 31 show typical BS-SEM images for all sample types. The BS-SEM images clearly show mineralized tissue (bone) ingrowth (light grey regions) at the two time periods for implants with CP over-layers as well as 'control' implants. The results of the quantitative image analysis for percent bone within available porosity are presented in Table 7. For the sections analyzed, the implant length was divided into four sections for analysis thereby allowing higher magnification images for the analysis. The four measurements were then averaged to give a percent bone ingrowth (and percent porosity) for each implant. The data from all the sections is included in Table 7 and indicates the variation that was observed along the implant length. This is not surprising in view of the structure of the cancellous bone into which the implants were placed. For each implant, a mean and standard deviation was determined. A one-way ANOVA was undertaken to determine if there were statistical differences between implants in the contralateral limbs for each rabbit. Statistical significance was considered at p<0.05. The different regions (bone, Ti alloy particles and unfilled pores, or at least not filled with bone) were readily distinguished by the Quantimet imaging software allowing an objective determination of the percent bone fill within the available pores. Only intra-animal comparisons were made (i.e. left and right legs within each animal). This provided seven sets for comparison including all the different conditions (Low S-CP, High S-CP, control at 9 days and 16 days) with two animals assessed for each condition with one exception. Unfortunately, the one lost implant (Rabbit 2C) could not be included.

TABLE 7

Summary of quantitative image analysis of BS-SEM examination

| | 9-day implants | | | | | | | |
|---|---|---|---|---|---|---|---|---|
| % bone/pores | 4AL-9dc | 4AR-9dl | 8AR-9dc | 8AL-9dl | 5BR-9dc | 5BL-9dh | 8BR-9dc | 8BL-9dh |
| | 33.47 | 13.93 | 14.50 | 17.39 | 22.81 | 16.42 | 9.42 | 12.77 |
| | 18.45 | 12.02 | 8.78 | 27.09 | 27.59 | 35.50 | 7.24 | 15.10 |
| | 32.30 | 23.57 | 9.48 | 16.37 | 30.66 | 35.13 | 8.18 | 23.57 |
| | 27.65 | 30.56 | 13.75 | 26.87 | 36.42 | 38.41 | 10.20 | 25.16 |
| mean | 27.97 | 20.02 | 11.63 | 21.93 | 29.37 | 31.37 | 8.76 | 19.15 |
| SD | 6.82 | 8.66 | 2.91 | 5.85 | 5.70 | 10.07 | 1.31 | 6.13 |
| ANOVA-p | 0.20 | | 0.02 | | 0.74 | | 0.02 | |

| | 16-day implants | | | | | | |
|---|---|---|---|---|---|---|---|
| | 9CL-16dc | 9CR-16dl | 2CL-16dc | 1DL-16dc | 1DR-16dh | 8DL-16dc | 8DR-16dh |
| | 44.44 | 26.61 | 39.34 | 41.53 | 26.26 | 34.67 | 48.21 |
| | 53.18 | 48.12 | 46.77 | 31.68 | 33.39 | 52.08 | 53.03 |
| | 42.44 | 50.70 | 50.53 | 42.12 | 38.59 | 42.03 | 53.06 |
| | 30.45 | 29.56 | 53.47 | 44.49 | 43.16 | 46.51 | 55.14 |
| mean | 42.63 | 38.75 | 47.53 | 39.96 | 35.35 | 43.82 | 52.36 |
| SD | 9.36 | 12.42 | 6.11 | 5.66 | 7.26 | 7.36 | 2.94 |
| ANOVA-p | 0.64 | | | 0.36 | | 0.075 | |

Despite the small number of samples analyzed, the quantitative image analysis does suggest some interesting additional findings.

The 9-day data indicates that in two rabbits (8A and 8B), % bone ingrowth was significantly higher for the S-CP-modified implants (8A, low S-CP and 8B high S-CP) compared to their respective 'control' implants (no CP over-layer). The other two 9-day rabbits that were analyzed did not show significant differences.

There were no significant differences in bone ingrowth between the CP-modified and 'control' implants at 16 days.

As before, these findings indicate that the S-CP-over-layers do not inhibit bone ingrowth. In fact, the BS-SEM images and the quantitative image analysis suggest that the addition of the S-CP over-layer may promote faster rates of bone ingrowth.

Quantitative image analysis was also used to confirm the percent porosity of the implants. The percent porosity as determined using the Quantimet software for the 17 sections analyzed was equal to 43.1±2.7%.

Histological Assessment of Rabbit Implants

The sections examined were prepared from 16 tissue-implant blocks harvested from 8 rabbits selected from the 40 rabbits and used in the study. Of these 16 samples for histology section preparation, the implant was not present in one block. That implant (sample 2C, 16-day 'Low' Ag+), presumably, had not osseointegrated but had migrated from the implant site after placement. The remaining 64 implants were mechanically tested (pull-out tests) to determine the shear strength and interface stiffness of the implant-bone interface zone as discussed above.

There was no obvious difference between implants that have been treated either high or low and controls (non-treated). Maturation of bone ingrowth over time was the same in all animals. No reaction was observed to implants that have been treated and no obvious cell death in surrounding bone. FIGS. 32 to 37 show representative micrographs of each condition indicating regions of bone ingrowth for all implants. This finding is consistent with the mechanical pull-out test results reported above.

Summary & Conclusions

1. The pull-out test results and the SEM images of the pulled out implants confirm that tissue ingrowth resulting in secure implant fixation occurs by 9 days for porous-surfaced implants with an overlayer of Ag+-modified calcium phosphate sol-gel-formed coatings.

2. The pull-out tests suggest that the modified coatings with the lower or higher Ag+-additions perform similarly.

3. As expected, the pull-out force for implant removal increased with increasing implantation period with significantly higher pull-out forces being recorded for the 16-day implanted samples compared with the 9-day samples. However, the interface zone stiffness values were not significantly different for the 9- and 16-day implanted samples although the mean values were higher for the 16-day implants.

4. While the recorded pull-out forces for the modified calcium phosphate-coated implants from the present study were not significantly different from those reported in a previous study (Tache et al), significantly higher interface zone stiffness values were observed. The higher interface stiffness may have been due to the longer implants used in the previous study (9 mm versus 7 mm length).

5. The addition of Ag+ to a sol-gel calcium phosphate film deposited over a porous-coated Ti-6Al-4V implant does not inhibit bone ingrowth. The two concentrations of silver that were tested appeared to give similar results.

Example VIII

Antimicrobial Activity of HA-Ag Coatings

Method

Suspension of test organism *S. aureus* ATCC 25923 containing approximately $10^6$ cfu/ml, was prepared by harvesting an overnight slope culture according to SOP/MB/003. The test coupons were tested according to SOP/MB/251; five coupons were placed into each 24 well sterile tissue culture plate flat bottom with low evaporation lid, the coupons were placed in the middle of the plate to lower the risk of evaporation. Acticoat (an antimicrobial silver-nanocrystalline wound dressing) samples were cut at 12 mm diameter. Each well was then inoculated with 2 ml of the test organism suspension and sealed with parafilm again to decrease the chances of any evaporation. The plates were incubated at 37° C. with agitation at 150 rpm for the relevant time periods. The time points tested were 0, 4, 24, 72 and 168 hours, there were six replicates at each time point. After the appropriate time period had elapsed 200 µl of neat sample was plated out as "true neat" plates in duplicate with neutralising agar (0.4% Sodium Thioglycolate and 1% Tween80), a further 200 µl was added to 1.8 ml of STS, 200 µl of this was plated in duplicate with TSA, 1 ml of this was also taken for the dilution series, which went down to $10^{-5}$ cfu/ml for samples and $10^{-4}$ cfu/ml for controls at 0 and 4 hours and then down to $10^{-6}$ cfu/ml for control samples at 24, 72 and 168 hours, and down to $10^{-5}$ cfu/ml for the rest of the samples. All of these were plated in duplicate on petrifilm and incubated along with the plates for 48 hours at 32° C.

Results and Discussion

PS-HA Coupons

Figure 38:
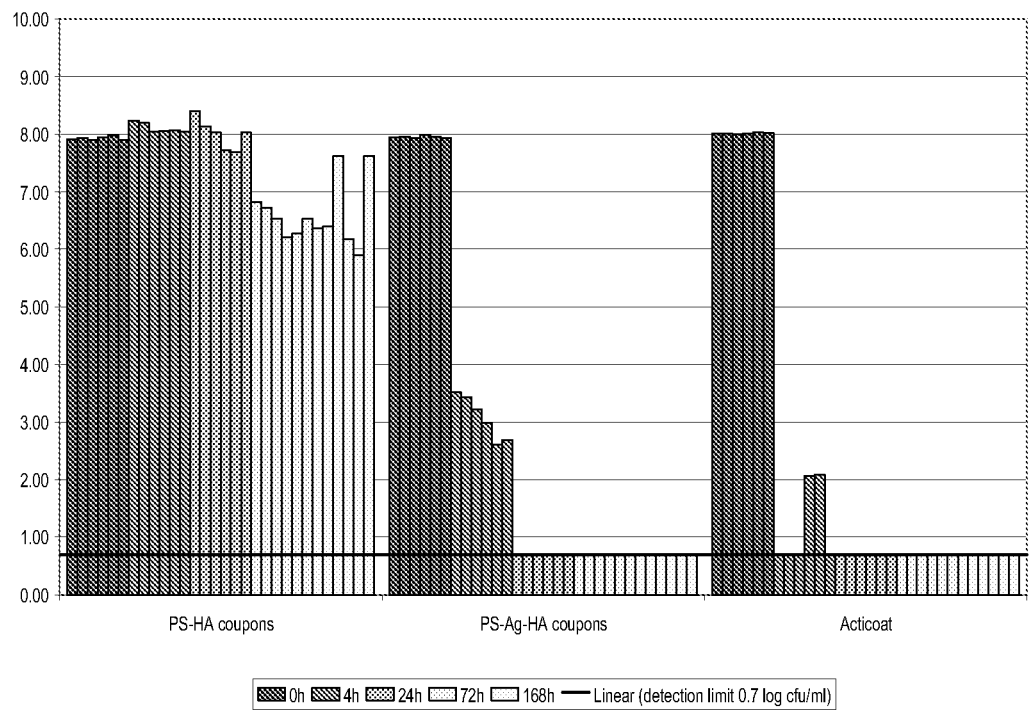
FIG. 38 shows antimicrobial activity measured by log reduction against *S. aureus*.

The results for the PS-HA control coupons can be seen in FIG. 38 and Table 8. The inoculum count was maintained through to 24 hours at 72 hours there was some natural die off, but no further die off occurred at 168 hours. This demonstrates the ability of S. aureus to grow in the presence of the PS-HA control coupons.

Acticoat

Acticoat was used as a positive control and demonstrated a decrease in counts of around 6 log/cfu sample at 4 hours with only two of the six replicate counts remaining above the detection limit. By 24 hours the counts from all replicates were below the detection limit, this continued to be the case at 72 hours and 168 hours.

PS-Ag-HA Coupons

PS-Ag-HA result can be seen in Table 8 and FIG. 38, a large decrease was seen at 4 hours of around 5 log/cfu ml with slight variability between replicates, this continued to decrease at 24 hours by a further mean 2 log/cfu sample taking all replicates below the detection limit. At 72 hours all replicates maintained this low level and this continued at 168 hours.

No grow back occurred with the PS-Ag-HA, this demonstrates that the PS-Ag HA coupons can kill S. aureus to a point that grow back will not occur before 168 hours, this point was reached at 24 hours. In previous investigations into other coating methods counts did not reach the detection limit and grow back was an issue. In this investigation the PS-Ag-HA coupons were completely successful at killing S. aureus for up to 168 hours.

It was noted that some of the PS-Ag-HA coupons had more surface area coverage of Ag than others, this occurred down the sides of the coupons. Also during this investigation it was also noted that some of the coating was dislodging from the coupons during the experiment.

TABLE 8

Mean log reductions achieved by test coupons against $10^6$ cfu/ml S. aureus.

| Coupons | Time Points | Mean log count (cfu/sample) | Mean log reduction (cfu/sample) |
|---|---|---|---|
| PS-HA coupon | 0 | 7.94 | N/A |
| | 4 | 8.13 | −0.19 |
| | 24 | 8.03 | −0.09 |
| | 72 | 6.49 | 1.45 |
| | 168 | 6.52 | 1.42 |

TABLE 8-continued

Mean log reductions achieved by test coupons against $10^6$ cfu/ml S. aureus.

| Coupons | Time Points | Mean log count (cfu/sample) | Mean log reduction (cfu/sample) |
|---|---|---|---|
| PS-Ag-HA | 0 | 7.95 | −0.02 |
| | 4 | 3.07 | 4.86 |
| | 24 | <0.70 | 7.24 |
| | 72 | <0.70 | 7.24 |
| | 168 | <0.70 | 7.24 |
| Acticoat | 0 | 8.01 | −0.07 |
| | 4 | 1.16 | 6.78 |
| | 24 | <0.70 | 7.24 |
| | 72 | <0.70 | 7.24 |
| | 168 | <0.70 | 7.24 |

CONCLUSION

Acticoat

By 4 hours Acticoat had shown a large decrease in S. aureus counts and by 24 hours had killed S. aureus to a level below the detection limit. No grow back had occurred by 168 hours.

PS-Ag-HA Coupons

The PS-Ag-HA coupons showed a large decrease in counts at 4 hours with slight variation between replicates. This could have been caused by the available surface area of silver variability. Counts continued to decrease and by 24 hours all replicates were below the detection limit where they stayed up to 168 hours.

The skilled person will realize that the breadth and scope of the present invention should not be limited by any of the above-described exemplary embodiments but should be defined only in accordance with any claims appended hereto and their equivalents.

The invention claimed is:

1. A medical implant comprising an implant surface having a surface coating comprising an active agent other than a bone conducting material and a functional gradient, the functional gradient comprising the distribution of the active agent in the surface coating, and wherein the active agent is in a concentration gradient within the surface coating, and the concentration of the active agent generally decreases through the surface coating as the distance of the active agent from the implant surface increases.

2. A medical implant comprising an implant surface having a surface coating comprising an active agent other than a bone conducting material and a functional gradient, the functional gradient comprising the distribution of the active agent in the surface coating, wherein the surface coating comprises two or more layers, and the concentration of the active agent in each layer is different and increases or decreases in each layer sequentially as the layers extend within the surface coating beyond the implant surface, and wherein the concentration of the active agent in the concentration gradient of the surface coating generally decreases as the distance from the implant surface increases.

3. A medical implant comprising an implant surface having a surface coating comprising an active agent other than a bone conducting material and a functional gradient, the functional gradient comprising the distribution of the active agent in the surface coating, and wherein the functional gradient further comprises the outer most portion of the surface coating, beyond the outer most end of the concentration gradient, wherein the concentration of the active agent in the outer most portion of the surface coating is higher than it would be in the outer most portion of the surface coating based on the concentration gradient alone.

4. The medical implant of claim 1, wherein the active agent is at least one of an antimicrobial agent, a bone stimulating agent, or an analgesic agent.

5. A medical implant comprising an implant surface having a surface coating comprising an active agent other than a bone conducting material and a functional gradient, the functional gradient comprising a concentration gradient of the active agent in the surface coating, wherein at least one active agent is a metal antimicrobial agent in the form of elemental metal, metal salts, metal ions, or metal containing compounds.

6. A medical implant comprising an implant surface having a surface coating comprising an active agent other than a bone conducting material and a functional gradient, the functional gradient comprising a concentration gradient of the active agent in the surface coating, wherein at least one active agent is a metal antimicrobial agent comprising an antimicrobially effective form of metal selected from the group consisting of silver, copper, or zinc.

7. The medical implant of claim 6, wherein the metal is silver.

8. The medical implant of claim 7, wherein the silver concentration in the surface coating ranges from about 0.1 to about 10 weight percent.

9. A medical implant comprising an implant surface having a surface coating comprising an active agent other than a bone conducting material and a functional gradient, the functional gradient comprising a concentration gradient of the active agent in the surface coating, wherein at least one active agent is a bone stimulating agent selected from the group consisting of carbonate, fluoride, silicon, magnesium, strontium, vanadium, lithium, a growth factor, a biomimetic peptide and combinations thereof.

10. The medical implant of claim 4, wherein the surface coating further comprises a bone conducting material capable of promoting osseointegration or osseoconductivity, comprising at least one of hydroxyapatite, tricalcium phosphate, or β-tricalcium phosphate.

11. A medical implant comprising an implant surface having a surface coating comprising an active agent other than a bone conducting material and a functional gradient, the functional gradient comprising a concentration gradient of the active agent in the surface coating, wherein the active agent comprises at least one of silver-containing hydroxyapatite, silver-containing tricalcium phosphate, or silver-containing β-tricalcium phosphate.

12. The medical implant of claim 4, wherein at least one active agent is an analgesic agent comprising at least one of bupivacaine, morphine, codeine, oxycodone, levorphanol, propoxyphene, acetylsalicylic acid, pentazocine, indomethacin, acetaminophen or phenacetin.

13. A medical implant comprising an implant surface having a surface coating comprising an active agent other than a bone conducting material and a functional gradient, the functional gradient comprising a concentration gradient of the active agent in the surface coating, wherein at least one active agent is an analgesic agent comprising at least one of bupivacaine, morphine, or codeine.

14. The medical implant of claim 4, wherein the active agent is at least one of an antimicrobial agent and at least one of a bone stimulating agent.

15. A medical implant comprising an implant surface having a surface coating comprising an active agent other than a bone conducting material and a functional gradient, the functional gradient comprising a concentration gradient of the active agent in the surface coating, wherein the active agent is at least one of an antimicrobial agent and at least one of a bone stimulating agent, and wherein the at least one antimicrobial agent comprises an antimicrobially effective form of a metal selected from the group consisting of silver, copper, or zinc.

16. The medical implant of claim 15, wherein at least one antimicrobial agent comprises an antimicrobially effective form of silver.

17. A medical implant comprising an implant surface having a surface coating comprising an active agent other than a bone conducting material and a functional gradient, the functional gradient comprising a concentration gradient of the active agent in the surface coating, and wherein the active agent comprises at least one of hydroxyapatite, calcium phosphate, tricalcium phosphate, β-tricalcium phosphate, silver-containing hydroxyapatite, silver-containing calcium phosphate, silver-containing tricalcium phosphate, or silver-containing β-tricalcium phosphate.

18. A medical implant comprising an implant surface having a surface coating comprising an active agent and a functional gradient, the functional gradient comprising the distribution of the active agent in the surface coating, wherein the active agent is at least one of an antimicrobial agent, a bone stimulating agent, or an analgesic agent, and wherein the active agent is at least one of an antimicrobial agent and at least one of an analgesic agent.

19. The medical implant of claim 18, wherein at least one antimicrobial agent comprises an antimicrobially effective form of a metal selected from the group consisting of silver, copper, or zinc.

20. The medical implant of claim 18, wherein at least one antimicrobial agent comprises an antimicrobially effective form of silver.

21. The medical implant of claim 18, wherein at least one analgesic agent comprises at least one of bupivacaine, morphine, codeine or oxycodone.

22. The medical implant of claim 4, wherein the active agent is at least one of a bone stimulating agent and at least one of an analgesic agent.

23. The medical implant of claim 22, wherein the surface coating further comprises at least one of hydroxyapatite, calcium phosphate, tricalcium phosphate, β-tricalcium phosphate, silver-containing hydroxyapatite, silver-containing calcium phosphate, silver-containing tricalcium phosphate, or silver-containing β-tricalcium phosphate.

24. The medical implant of claim 22, wherein at least one analgesic agent comprising at least one of bupivacaine, morphine, codeine or oxycodone.

25. A medical implant comprising an implant surface having a surface coating comprising an active agent and a functional gradient, the functional gradient comprising the distribution of the active agent in the surface coating, wherein the active agent is at least one of an antimicrobial agent, a bone stimulating agent, or an analgesic agent, and wherein the active agent is at least one of an antimicrobial agent, at least one of a bone stimulating agent, and at least one of an analgesic agent.

26. The medical implant of claim 25, wherein the surface coating further comprises at least one of hydroxyapatite, calcium phosphate, tricalcium phosphate, β-tricalcium phosphate, silver-containing hydroxyapatite, silver-containing calcium phosphate, silver-containing tricalcium phosphate, or silver-containing β-tricalcium phosphate the at least one antimicrobial agent comprises an antimicrobially effective form of silver, and the at least one analgesic agent comprises at least one of bupivacaine, morphine, codeine or oxycodone.

27. A method of treating a patient in need of a medical implant comprising surgically placing the medical implant of claim 1 into said patient.

28. A method of treating a patient in need of a medical implant comprising surgically placing the medical implant of claim 4 into said patient.

29. A method of treating a patient in need of a medical implant comprising surgically placing the medical implant of claim 14 into said patient.

30. A method of treating a patient in need of a medical implant comprising surgically placing the medical implant of claim 18 into said patient.

31. A method of treating a patient in need of a medical implant comprising surgically placing the medical implant of claim 22 into said patient.

32. A method of treating a patient in need of a medical implant comprising surgically placing the medical implant of claim 25 into said patient.

33. A method of treating a patient in need of a medical implant comprising surgically placing the medical implant of claim 26 into said patient.

34. A medical implant comprising an implant surface having a surface coating comprising an active agent other than a bone conducting material and a functional gradient, the functional gradient comprising a concentration gradient of the active agent in the surface coating, and wherein the active agent comprises a member selected from the group consisting of an antimicrobial agent, an antibacterial agent, an antibiotic, a steroid, an anti-inflammatory, and antispasmodic, a hemostat, a dissolution-controlling element, a bonding strength increasing element, a protein, a BMP and an analgesic.

35. A medical implant comprising an implant surface having a surface coating comprising an active agent other than a bone conducting material and a functional gradient, the functional gradient comprising a concentration gradient of the active agent in the surface coating, and where the active agent comprises a bone stimulating agent selected from the group consisting of carbonate, fluoride, silicon, magnesium, strontium, vanadium, lithium, a growth factor, a biomimetic peptide, and any combination thereof.

36. The medical implant of claim 1, wherein the surface coating further comprises a bone conducting material capable of promoting osseointegration or osseoconductivity.

37. The medical implant of claim 36, wherein the bone conducting material comprises at least one of hydroxyapatite, calcium phosphate, calcium orthophosphate, tricalcium phosphate, ceramic bioglass, fluoride, fluorine, calcium nitrate, silver-containing hydroxyapatite, silver-containing calcium phosphate, silver-containing tricalcium phosphate, β-tricalcium phosphate, silver-containing β-tricalcium phosphate, calcium carbonate, silver-containing calcium carbonate, calcium-deficient hydroxyapatite, silver-containing calcium-deficient hydroxyapatite, resorbable polymers, bioglass, silicon, magnesium, strontium, vanadium, or lithium.

38. The medical implant of claim 36, wherein the bone conducting material comprises at least one of hydroxyapatite, tricalcium phosphate, or β-tricalcium phosphate.

\* \* \* \* \*